(12) United States Patent
Puskas

(10) Patent No.: US 7,004,016 B1
(45) Date of Patent: Feb. 28, 2006

(54) PROBE SYSTEM FOR ULTRASONIC PROCESSING TANK

(76) Inventor: William L. Puskas, P.O. Box 1676, New London, NH (US) 03257

( * ) Notice: Subject to any disclaimer, the term of this patent is extended or adjusted under 35 U.S.C. 154(b) by 0 days.

(21) Appl. No.: 09/370,302

(22) Filed: Aug. 9, 1999

(51) Int. Cl.
*G01N 29/00* (2006.01)
*B08B 3/00* (2006.01)

(52) U.S. Cl. ................. 73/64.53; 134/57 R; 134/184; 134/902

(58) Field of Classification Search ............. 73/64.53, 73/64.56, 866.5, 649, 60.11; 134/113, 902, 134/57 R, 184, 58 R, 200
See application file for complete search history.

(56) References Cited

U.S. PATENT DOCUMENTS

| | | | |
|---|---|---|---|
| 2,585,103 A | 2/1952 | Fitzgerald | 99/451 |
| 2,891,176 A | 6/1959 | Branson | 310/317 |
| 2,985,003 A | 5/1961 | Gelfand | 68/3 R |
| 3,066,232 A | 11/1962 | Branson | 310/325 |
| 3,094,314 A | 6/1963 | Kearney et al. | 366/115 |
| 3,113,761 A | 12/1963 | Platzman | 366/115 |
| 3,152,295 A | 10/1964 | Schebler | 318/118 |
| 3,187,207 A | 6/1965 | Tomes | 310/325 |
| 3,230,403 A | 1/1966 | Lewis et al. | 310/334 |
| 3,293,456 A | 12/1966 | Shoh | 310/316.01 |
| 3,315,102 A | 4/1967 | Quint et al. | 310/317 |
| 3,318,578 A | 5/1967 | Branson | 366/118 |
| 3,371,233 A | 2/1968 | Cook | 310/317 |
| 3,433,462 A | 3/1969 | Cook | 366/127 |
| 3,629,726 A | 12/1971 | Popescu | 331/116 M |
| 3,638,087 A | 1/1972 | Ratcliff | 318/118 |
| 3,648,188 A | 3/1972 | Ratcliff | 330/291 |

(Continued)

FOREIGN PATENT DOCUMENTS

DE   29 50 893   12/1979

(Continued)

*Primary Examiner*—Hezron Williams
*Assistant Examiner*—Tamiko Bellamy
(74) *Attorney, Agent, or Firm*—McDermott Will & Emery LLP

(57) ABSTRACT

The invention provides systems, methods and apparatus for processing delicate parts within a process tank such as an ultrasonic tank. Typically, one or more transducers connect to the tank and respond to drive signals from a generator to produce ultrasound within process liquid within the tank. Specific features of the invention include: (1) a power up-sweep ultrasonic system for moving contaminants upwards within the tank by sweeping transducer drive signals from an upper frequency to a lower frequency without sweeping from the lower frequency to the upper frequency; (2) a multi-generator system for producing ultrasound at selected different frequencies within the tank by switching a common transducer bank to one of the generators in response to remote relays initiated by the user; (3) a probe sensing system for sensing process conditions within the tank including an enclosure for housing a sample liquid and one or more sensing transducers within the sample liquid, the transducers generating signals indicative of characteristics of the sample liquid, a subsystem analyzing the signals in feedback with the generator to modify process conditions; (4) variable voltage ultrasonic generator systems to accommodate varying world-wide voltage supplies; (5) a laminar process tank for efficiently pushing contaminants upwards in a tank; (6) a quick dump rinse tank including a pressure cavity to accelerate dumping processes; (7) an ultrasonic generating unit formed of a printed circuit board (PCB) and multiple transducers within the PCB; (8) an AC power system to produce an AC voltage at frequency f that is impressed across a capacitive element; and (9) various configurations of transducers, including acid-safe transducers, double-compression transducers, and transducers with increased reliability.

34 Claims, 45 Drawing Sheets

U.S. PATENT DOCUMENTS

| | | | |
|---|---|---|---|
| 3,651,352 A | 3/1972 | Puskas | 310/316.01 |
| 3,690,333 A | 9/1972 | Kierner | 134/95.1 |
| 3,727,112 A | 4/1973 | Popescu | 361/203 |
| 3,735,159 A | 5/1973 | Murry | 310/325 |
| 3,746,897 A | 7/1973 | Karatjas | 310/8.1 |
| 3,778,758 A | 12/1973 | Carson | 310/322 |
| 3,804,329 A | 4/1974 | Martner | 239/4 |
| 3,842,340 A | 10/1974 | Brandquist | 363/96 |
| 3,893,869 A | 7/1975 | Mayer et al. | 134/86 |
| 3,939,401 A * | 2/1976 | Van Lenten et al. | 324/450 |
| 3,975,650 A | 8/1976 | Payne | 310/316.01 |
| 4,044,297 A | 8/1977 | Nobue et al. | 323/271 |
| 4,054,848 A | 10/1977 | Akita | 331/116 R |
| 4,069,444 A | 1/1978 | Heim | 318/114 |
| 4,081,706 A | 3/1978 | Edelson | 310/316.01 |
| 4,109,174 A | 8/1978 | Hodgson | 310/316.03 |
| 4,118,649 A | 10/1978 | Shwartzman et al. | 310/337 |
| 4,120,699 A | 10/1978 | Kennedy, Jr. et al. | 134/1 |
| 4,141,608 A | 2/1979 | Breining et al. | 310/316.01 |
| 4,156,157 A | 5/1979 | Mabille | 310/316.01 |
| 4,175,242 A | 11/1979 | Kleinschmidt | 310/316.01 |
| 4,275,363 A | 6/1981 | Mishiro et al. | 331/4 |
| 4,326,553 A | 4/1982 | Hall | 134/153 |
| 4,391,672 A | 7/1983 | Lehtinen | 162/192 |
| 4,398,925 A | 8/1983 | Trinh et al. | 95/30 |
| 4,409,999 A | 10/1983 | Pedziwiatr | 134/95.2 |
| 4,418,297 A | 11/1983 | Marshall | 310/316.01 |
| 4,431,975 A | 2/1984 | Podlesny | 331/117 R |
| 4,527,901 A | 7/1985 | Cook | 366/127 |
| 4,543,130 A | 9/1985 | Shwartzman | 134/1 |
| 4,554,477 A | 11/1985 | Ratcliff | 310/316.01 |
| 4,559,826 A | 12/1985 | Nelson | 73/632 |
| 4,633,119 A | 12/1986 | Thompson | 310/325 |
| 4,736,130 A | 4/1988 | Puskas | 310/316.01 |
| 4,743,789 A | 5/1988 | Puskas | 310/316.01 |
| 4,788,992 A | 12/1988 | Swainbank et al. | 134/64 R |
| 4,804,007 A | 2/1989 | Bran | 134/184 |
| 4,836,684 A | 6/1989 | Javorik et al. | 366/114 |
| 4,854,337 A | 8/1989 | Bunkenburg et al. | 134/184 |
| 4,864,547 A | 9/1989 | Krsna | 367/137 |
| 4,869,278 A | 9/1989 | Bran | 134/184 |
| 4,890,481 A * | 1/1990 | Ezawa et al. | 73/61.71 |
| 4,979,994 A | 12/1990 | Dussault et al. | 134/1 |
| 4,998,549 A | 3/1991 | Bran | 134/184 |
| 5,037,208 A | 8/1991 | Dussault et al. | 366/127 |
| 5,037,481 A | 8/1991 | Bran | 134/1 |
| 5,090,432 A | 2/1992 | Bran | 134/139 |
| 5,119,840 A | 6/1992 | Shibata | 134/184 |
| 5,143,103 A | 9/1992 | Basso et al. | 134/98.1 |
| 5,148,823 A | 9/1992 | Bran | 134/184 |
| 5,201,958 A | 4/1993 | Breunsbach et al. | 134/1 |
| 5,218,980 A | 6/1993 | Evans | 134/68 |
| 5,247,954 A | 9/1993 | Grant et al. | 134/184 |
| 5,276,376 A | 1/1994 | Puskas | 310/317 |
| 5,286,657 A | 2/1994 | Bran | 134/1.3 |
| 5,305,737 A | 4/1994 | Vago | 601/4 |
| 5,355,048 A | 10/1994 | Estes | 310/334 |
| 5,365,960 A | 11/1994 | Bran | 134/184 |
| 5,433,102 A * | 7/1995 | Pedziwiatr | 73/1.83 |
| 5,496,411 A | 3/1996 | Candy | 134/1 |
| 5,534,076 A | 7/1996 | Bran | 134/1 |
| 5,931,173 A * | 8/1999 | Schiele | 134/57 R |
| 6,295,873 B1 * | 10/2001 | Condreva | 73/597 |
| 6,394,111 B1 * | 5/2002 | Jacobs et al. | 134/113 |

FOREIGN PATENT DOCUMENTS

| | | | |
|---|---|---|---|
| EP | 0 123 277 | | 10/1984 |
| GB | 1 256 188 | | 12/1971 |
| GB | 1 323 196 | | 7/1973 |
| GB | 1 331 100 | | 9/1973 |
| GB | 1 488 252 | | 10/1977 |
| GB | 2 060 220 | | 4/1981 |
| GB | 2 097 890 | | 11/1982 |
| GB | 2 161 037 | | 1/1986 |
| GB | 2 170 663 | | 8/1986 |
| JP | 07163954 A | * | 6/1995 |
| WO | 97/42790 | | 11/1997 |

* cited by examiner

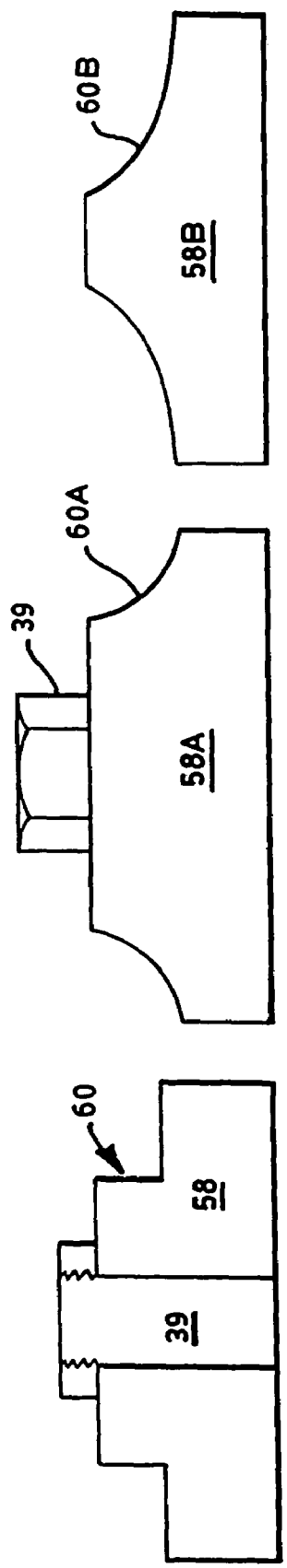

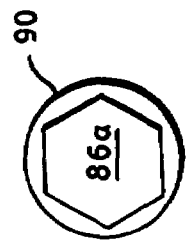
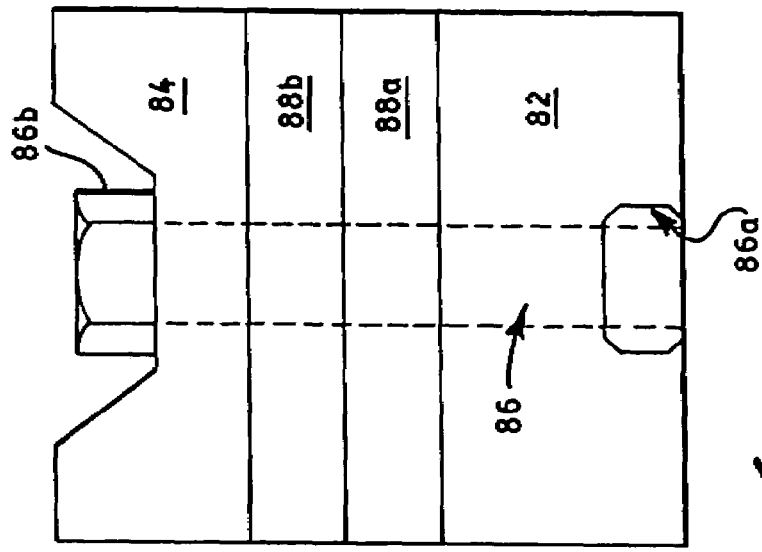
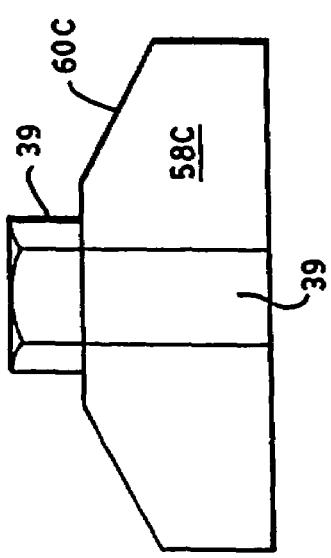
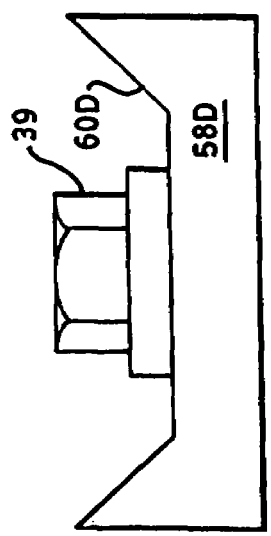

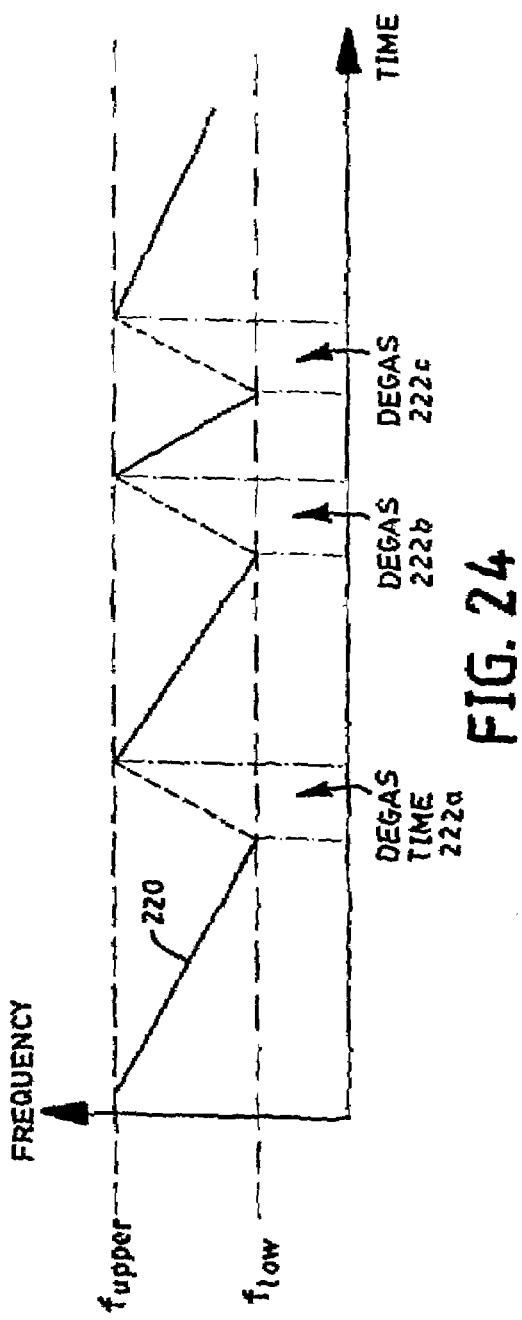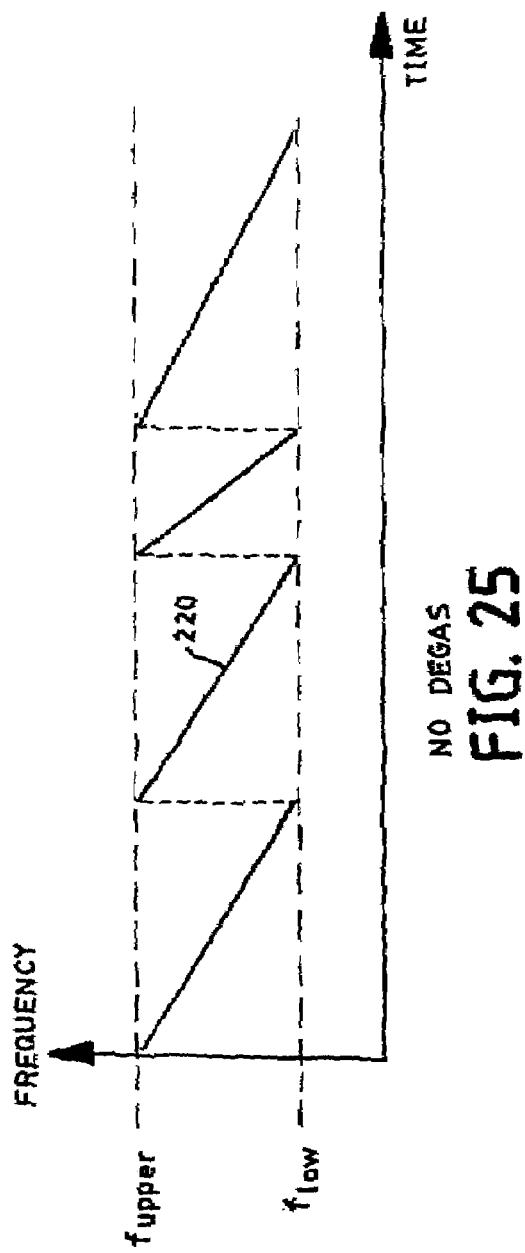

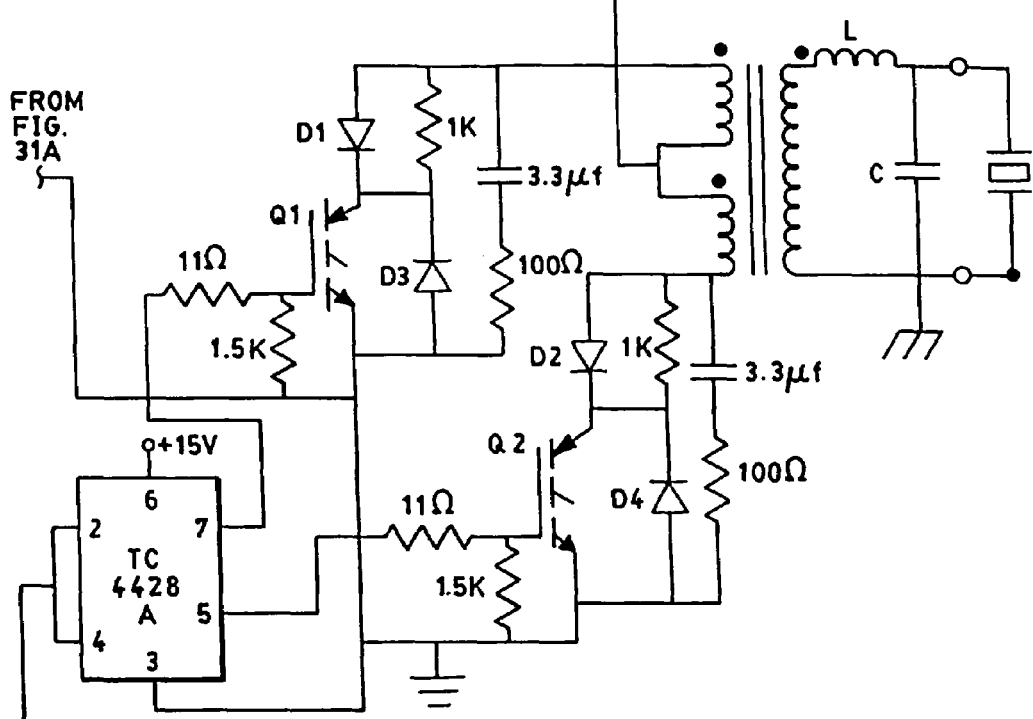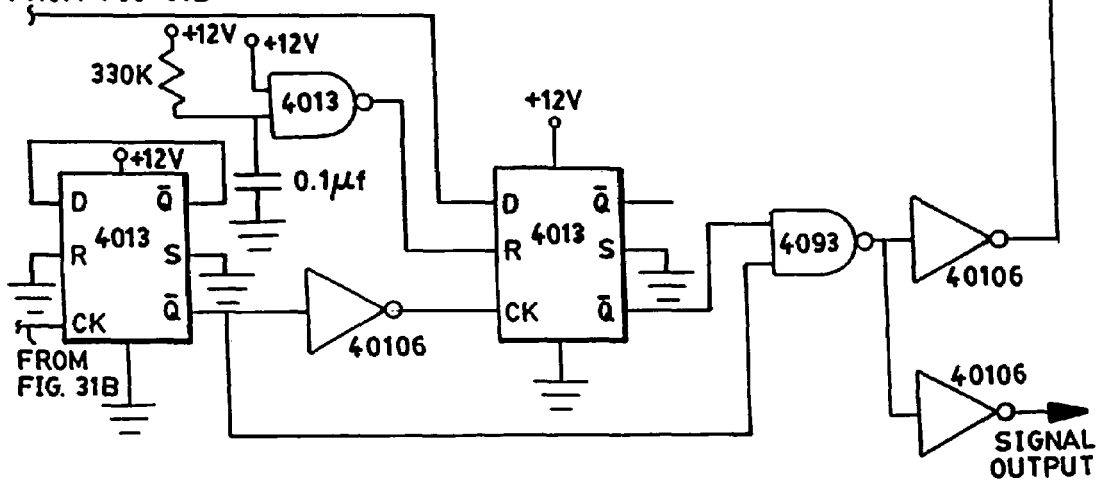
FIG. 31C

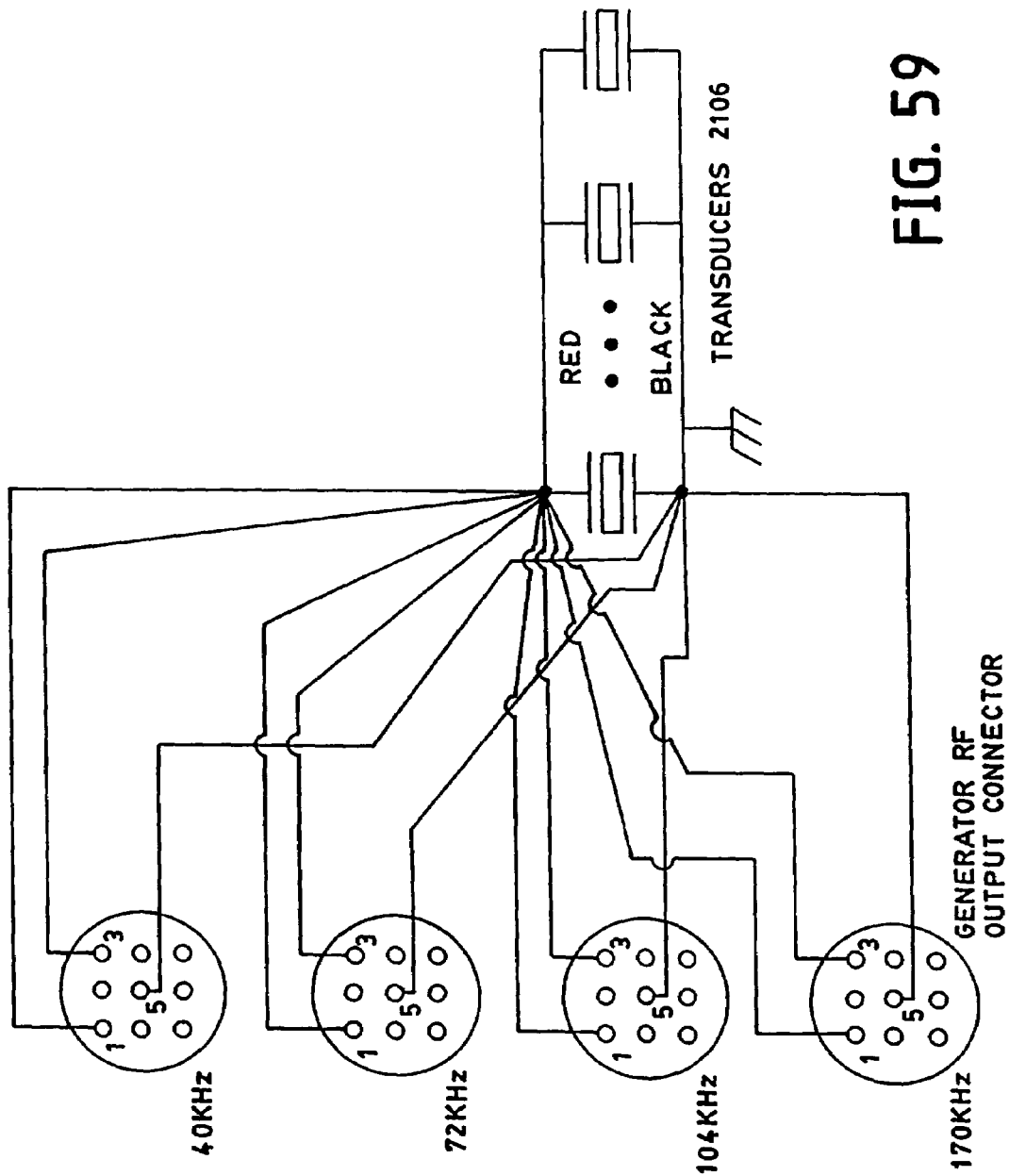

PROBE SYSTEM FOR ULTRASONIC PROCESSING TANK

RELATED APPLICATIONS

This application is a divisional application of U.S. patent application Ser. No. 09/097,374, filed Jun. 15, 1998, which is a continuation in part of U.S. patent application Ser. No. 08/718,945, filed Sep. 24, 1996, and which claims the benefit of U.S. Provisional Patent Application Ser. No. 60/049,717, filed Jun. 16, 1997, each of which is hereby incorporated by reference.

BACKGROUND OF THE INVENTION

Ultrasonic systems for processing and cleaning parts are widely used by industry. Such systems typically include (a) a tank to hold the process chemistry such as cleaning solution, (b) an ultrasound generator, and (c) one or more transducers connected to the tank and the generator to deliver ultrasound energy to the process chemistry. These systems are generally adequate for low frequency operation, i.e., where the energy applied to the chemistry is around 20 khz. However, prior art ultrasound processing equipment has important technology limitations when operating at high frequencies and high power; and delicate parts such as disk drives for the computer industry require high frequency, high power ultrasound in order to effectively process components without damage. In one failure mode, for example, prior art transducers are known to fail when subjected to extended periods of operation, especially at high frequency and high power. In addition, prior art transducers are generally non-linear with respect to power output as a function of drive frequency. Therefore, prior art ultrasonic processing systems sometimes include costly electronics to compensate for such non-linearities.

There are other problems. For example, certain manufacturers require that a particular generator be matched to a particular tank since that combination is measured and known to provide particular process characteristics. However, this is cumbersome to an end user who cannot swap one generator for another in the event of a failure. More importantly, though, end users are not able to effectively monitor whether the system has degraded. Typically, for example, end users become aware of failure modes only after parts are damaged or destroyed within the process. There is a need, therefore, of monitoring systems which monitor processes in real-time.

It is, accordingly, one object of the invention to provide systems, apparatus and methods for delivering high frequency, high power ultrasound energy to process chemistries. Another object of the invention is to provide generators and systems which enable multi-frequency operation, selectively and without undue difficulty. Still another object of the invention is to provide improved transducer designs which increase system reliability and which improve power delivery. Yet another object of the invention is to provide systems, apparatus and methods for monitoring ultrasound processes in real-time or as a quality control ("QC") step.

SUMMARY OF THE INVENTION

As used herein, "ultrasound" and "ultrasonic" generally refer to acoustic disturbances in a frequency range above about eighteen kilohertz and which extend upwards to over two megahertz. "Lower frequency" ultrasound, or "low frequency" ultrasound mean ultrasound between about 18 khz and 90 khz. "Megasonics" or "megasonic" refer to acoustic disturbances between 600 khz and 2 Mhz. As discussed above, the prior art has manufactured "low frequency" and "megasonic" ultrasound systems. Typical prior art low frequency systems, for example, operate at 25 khz, 40 khz, and as high as 90 khz. Typical prior art megasonic systems operate between 600 khz and 1 Mhz. Certain aspects of the invention apply to low frequency ultrasound and to megasonics. However, certain aspects of the invention apply to ultrasound in the 100 khz to 350 khz region, a frequency range which is sometimes denoted herein as "microsonics."

As used herein, "resonant transducer" means a transducer operated at a frequency or in a range of frequencies that correspond to a one-half wavelentgh ($\lambda$) of sound in the transducer stack. "Harmonic transducer" means a transducer operated at a frequency or in a range of frequencies that correspond to $1\lambda$, $1.5\lambda$, $2\lambda$ or $2.5\lambda$ of sound, and so on, in the transducer stack. "Bandwidth" means the range of frequencies in a resonant or harmonic region of a transducer over which the acoustic power output of a transducer remains between 50% and 100% of the maximum value.

As used herein, a "delicate part" refers to those parts which are undergoing a manufacture, process, or cleaning operation within liquid subjected to ultrasonic energy. By way of example, one delicate part is a semiconductor wafer which has extremely small features and which is easily damaged by cavitation implosion. A delicate part often defines components in the computer industry, including disk drives, semiconductor components, and the like.

As used herein, "khz" refers to kilohertz and a frequency magnitude of one thousand hertz. "MHz" refers to megahertz and a frequency magnitude of one million hertz.

As used herein, "sweep rate" or "sweep frequency" refer to the rate or frequency at which a generator and transducer's frequency is varied. That is, it is generally undesirable to operate an ultrasonic transducer at a fixed, single frequency because of the resonances created at that frequency. Therefore, an ultrasonic generator can sweep (i.e., linearly change) the operational frequency through some or all of the available frequencies within the transducer's bandwidth at a "sweep rate." Accordingly, particular frequencies have only short duration during the sweep cycle (i.e., the time period for sweeping the ultrasound frequency through a range of frequencies within the bandwidth). "Sweep the sweep rate" or "double sweeping" or "dual sweep" refer to an operation of changing the sweep rate as a function of time. In accord with the invention, "sweeping the sweep rate" generally refers to the operation of sweeping (i.e., linearly changing) the sweep rate so as to reduce or eliminate resonances generated at the sweep frequency.

In one aspect, the invention provides ultrasound transducer apparatus. In the apparatus, at least one ceramic drive element is sandwiched between a front driver and a backplate. The drive element has electrical contacts or electrodes mounted on either face and is responsive to voltages applied to the contacts or electrodes so as to produce ultrasound energy. A connecting element—e.g., a bolt—connects the back plate to the front driver and compresses the drive element therebetween. In accord with the invention, the front driver and/or the backplate are shaped so that the apparatus produces substantially uniform power as a function of frequency over a range of frequencies. In another aspect, the shape of the driver and/or backplate are selected so as to provide a varying power function as a function of frequency.

In another aspect, a multi-frequency ultrasound generator is provided. In one aspect, the generator includes a constant power output circuit with means for switching the center frequency of the output signal selectively. The switching means operates such that little or no intermediate frequencies are output during transition between one center frequency and another.

Another multi-frequency generator of the invention includes two or more circuits which independently create ultrasound frequencies. By way of example, one circuit can generate 40 khz ultrasound energy; while another circuit can generate 104 khz energy. A switching network connects the plurality of circuits such that the generator is shut down and relay switching takes place in a zero voltage condition. As above, therefore, the switching occurs such that little or no intermediate frequencies are output during transition between one center frequency and another.

In still another aspect, a two stage ultrasonic processing system is provided. The system includes (a) one or more transducers with a defined ultrasound bandwidth defined by an upper frequency and a lower frequency. The system further includes (b) a frequency generator for driving the transducers from the upper frequency to the lower frequency over a selected or variable time period and (c) a process tank connected with the transducers so as to generate ultrasound energy within the tank at frequencies defined by the generator. During a given cycle, the generator drives the transducers from the upper frequency to the lower frequency. Once the lower frequency is reached, a frequency control subsystem controls the generator so as to drive the transducers again from upper to lower frequency and without driving the transducers from lower to upper frequencies. In this manner, only decreasing frequencies—per cycle—are imparted to process chemistries. The system thus provides for removing contamination as the downward cycling frequencies cause the acoustic energy to migrate in an upwards motion inside the tank which in turn pushes contamination upwards and out of the tank.

In another aspect of the invention, the two stage ultrasonic processing system includes means for cycling from upper-to-lower frequencies every half cycle. That is, once the transducers are driven from upper to lower frequencies over a first half cycle, the generator recycles such that the next half cycle again drives the transducers from upper to lower frequencies. Alternatively, after driving the transducers from upper to lower frequencies for a first half cycle, the system inhibits the flow of energy into the tank over a second half cycle.

The two stage ultrasonic processing systems of the invention can be continuous or intermittent. That is, in one preferred aspect, the system cycles from upper to lower frequencies and then from lower to upper frequencies in a normal mode; and then only cycles from upper to lower frequencies in a contamination removing mode.

In still another aspect, the invention provides a process control probe which monitors certain process characteristics within an ultrasonic process tank. The probe includes an enclosure, e.g., made from polypropylene, that transmits ultrasound energy therethrough. The enclosure houses a liquid that is responsive to the ultrasonic energy in some manner such as to create free radicals and ions from which conductivity can be measured. This conductivity provides an indication as to the number of cavitation implosions per unit volume being imparted to the process chemistry within the tank. A conduit from the enclosure to a location external to the process chemistry is used to measure the characteristics of the liquid in response to the energy. In other aspects, a thermocouple is included within the enclosure and/or on an external surface of the enclosure (i.e., in contact with the process chemistry) so as to monitor temperature changes within the enclosure and/or within the process chemistry. Other characteristics within the tank and/or enclosure can be monitored over time so as to create time-varying functions that provide other useful information about the characteristics of the processes within the tank.

In one aspect, the invention provides an ultrasonic system for moving contaminants upwards within a processing tank, which holds process liquid. An ultrasonic generator produces ultrasonic drive signals through a range of frequencies as defined by an upper frequency and a lower frequency. A transducer connected to the tank and the generator responds to the drive signals to impart ultrasonic energy to the liquid. A controller subsystem controls the generator such that the drive signals monitonically change from the upper frequency to the lower frequency to drive contaminants upwards through the liquid.

In one aspect, the controller subsystem cyclically produces the drive signals such that the generator sweeps the drive signals from the upper frequency to the lower frequency over a first half cycle, and from the lower frequency to the higher frequency over a second one half cycle. The subsystem of this aspect inhibits the drive signals over the second half cycle to provide a quiet period to the liquid.

In other aspects, the first and second one-half cycles can have different time periods. Each successive one-half cycle can have a different time period such that a repetition rate of the first and second half cycles is non-constant. Or, the first one-half cycle can have a fixed period and the second one-half cycle can be non-constant.

In one aspect, the first half cycle corresponds to a first time period and the second one half cycle corresponds to a second time period, and the subsystem varies the first or second time periods between adjacent cycles.

Preferably, the subsystem includes means for shutting the generator off during the second one half cycle.

In another aspect, the subsystem includes an AM modulator for amplitude modulating the drive signals at an AM frequency. In one aspect, the AM modulator sweeps the AM frequency. In another aspect, the AM modulator sweeps the AM frequency from a high frequency to a low frequency and without sweeping the AM frequency from the low frequency to the high frequency. The subsystem can further inject a quiet or degas period before each monotonic AM frequency sweep.

In another aspect, there is provided an ultrasonic system for moving contaminants upwards within a processing tank, including: a processing tank for holding process liquid, an ultrasonic generator for generating ultrasonic drive signals through a range of frequencies defined between an upper frequency and a lower frequency, at least one transducer connected to the tank and the generator, the transducer being responsive to the drive signals to impart ultrasonic energy to the liquid, and a controller subsystem for controlling the generator through one or more cycles, each cycle including monotonically sweeping the drive signals from the upper frequency to the lower frequency, during a sweep period, and recycling the generator from the lower frequency to the upper frequency, during a recovery period, the sweep period being at least nine times longer than the recovery period.

In one aspect, the controller subsystem varies a time period for each cycle wherein the time period is non-constant.

In still another aspect, an ultrasonic system is provided for moving contaminants upwards within a processing tank, including: a processing tank for holding process liquid; an ultrasonic generator for generating ultrasonic drive signals; at least one transducer connected to the tank and the generator, the transducer being responsive to the drive signals to impart ultrasonic energy to the liquid; and an amplitude modulation subsystem for amplitude modulating the drive signals through a range of AM frequencies characterized by an upper frequency and a lower frequency, the subsystem monotonically changing the AM frequency from the upper frequency to the lower frequency to drive contaminants upwards through the liquid.

In one aspect, the generator sweeps the drive signals from upper to lower frequencies to provide additional upwards motion of contaminants within the liquid.

In another aspect, the AM frequencies are between about 1.2 khz and a lower frequency of 1 Hz. The AM frequencies can also cover a different range, such as between about 800 Hz and a lower frequency of 200 Hz.

In another aspect, the invention provides a multi-generator system for producing ultrasound at selected different frequencies within a processing tank of the type including one or more transducers. A generator section has a first generator circuit for producing first ultrasonic drive signals over a first range of frequencies and a second generator circuit for producing second ultrasonic drive signals over a second range of frequencies. The generator section has an output unit connecting the drive signals to the transducers. Each generator circuit has a first relay initiated by a user-selected command wherein either the first or the second drive signals are connected to the output unit selectively.

In one aspect, a 24 VDC supply provides power for relay coils.

In another aspect, each generator circuit has a second relay for energizing the circuit. Two time delay circuits can also be included for delay purposes: the first time delay circuit delaying generator circuit operation over a first delay period from when the second relay is energized, the second time delay circuit delaying discontinuence of the first relay over a second delay period after the generator circuit is commanded to stop. The first delay period is preferably longer than the second delay period such that no two generators circuits operate simultaneously and such that all generator circuits are inactive during switching of the first relay.

Each relay can include a 24 VDC coil. A selecting device, e.g., a PLC, computer, or selector switch, can be used to select the operating generator circuit. At selection, 24 VDC connects to the two relays of this operating generator circuit. Preferably, each relay coil operates at a common voltage level.

In one aspect, a variable voltage ultrasonic generator system is provided, including: an ultrasonic generator; a switching regulator for regulating a 300 VDC signal to +12V and +15V lines, the generator being connected to the +12V and +15V lines; and a power factor correction circuit connected to AC power. The power factor correction circuit provides 300 VDC output to the generator and to the regulator. The generator thus being automatically operable from world voltage sources between 86 VAC and 264 VAC.

In another aspect, a variable voltage ultrasonic generator system is provided, including: an ultrasonic generator; and a universal switching regulator (known to those skilled in the art), connected to AC power, for regulating a set of DC voltages to the generator. The generator thus being automatically operable from world voltage sources between 86 VAC and 264 VAC.

In another aspect, a double compression transducer is provided for producing ultrasound within an ultrasound tank. The transducer has a front plate and a backplate. At least one piezoceramic is sandwiched between the front plate and backplate. A bias bolt with an elongated bias bolt body between a bias bolt head and a threaded portion extends through the front plate and the piezoceramic and is connected with the backplate (either by screwing into the backplate or by a nut screwed onto the bias bolt adjacent the backplate). The bias bolt also forms a through-hole interior that axially extends between the head and the threaded portion. A second bolt with an elongated body between a second bolt head and a threaded tip is disposed within the bias bolt. The second bolt head is rigidly attached to the tank and a nut is screwed onto the threaded tip and adjacent to the backplate. The bias bolt thus provides a first level of compression of the piezoceramic. The second bolt provides a second level of compression of the front plate and the tank, particularly when epoxy is used to bond between the front plate and the tank.

In still another aspect, a variable voltage ultrasonic generator system is provided. The system includes an ultrasonic generator and a constant peak amplitude triac circuit connected to AC power. The triac circuit converts the AC power to a 121.6 voltage peak, or less, AC signal. A bridge rectifier and filter connects to the AC signal to rectify and filter the AC signal and to generate a DC voltage less than $(86)(\sqrt{2})$ volts. A switching regulator regulates the DC voltage to 12 VDC and 15 VDC; and the generator connects to the DC voltage, the 12 VDC and the 15 VDC. In this manner, the generator is thus automatically operable from world voltage sources between 86 VAC and 264 VAC.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which:

FIGS. 6–16 show transducer and backplate embodiments for systems, methods and transducers of the invention.

FIGS. 24 and 25 show alternative timing cycles through which the system of FIG. 23 applies ultrasound from upper to lower frequencies;

FIG. 59 shows a wiring schematic to couple the generators to a single processing tank with transducers.

DETAILED DESCRIPTION OF THE DRAWINGS

Figure 1:
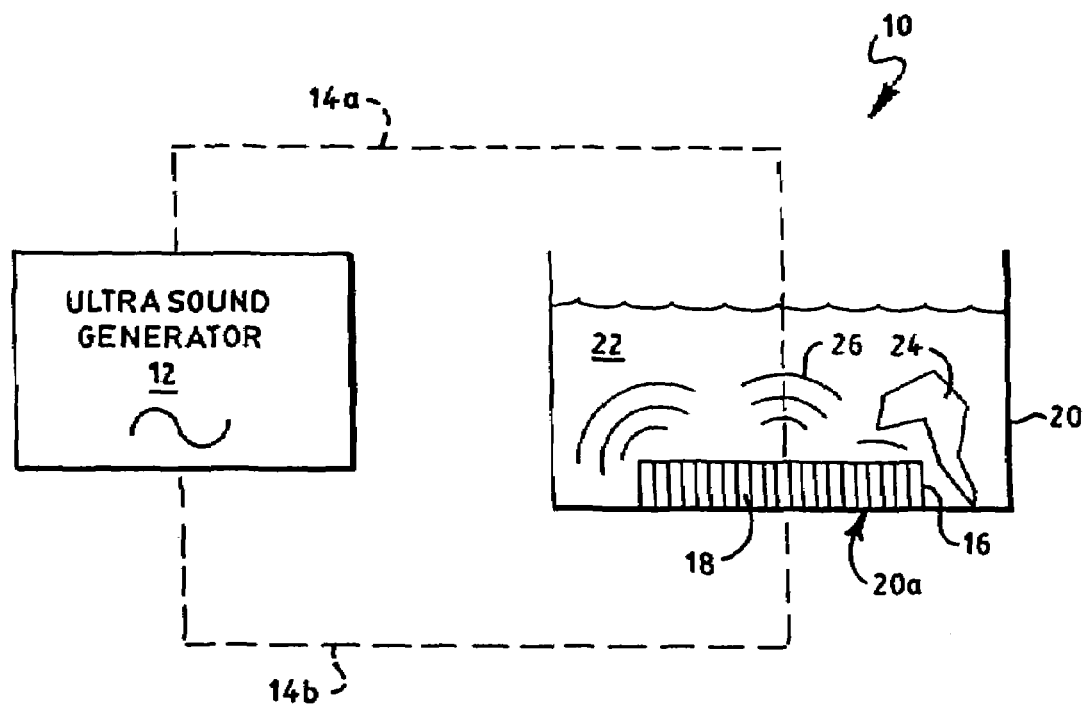
FIG. 1 shows a cut-away side view schematic of an ultrasound processing system constructed according to the invention.
Figure 2:
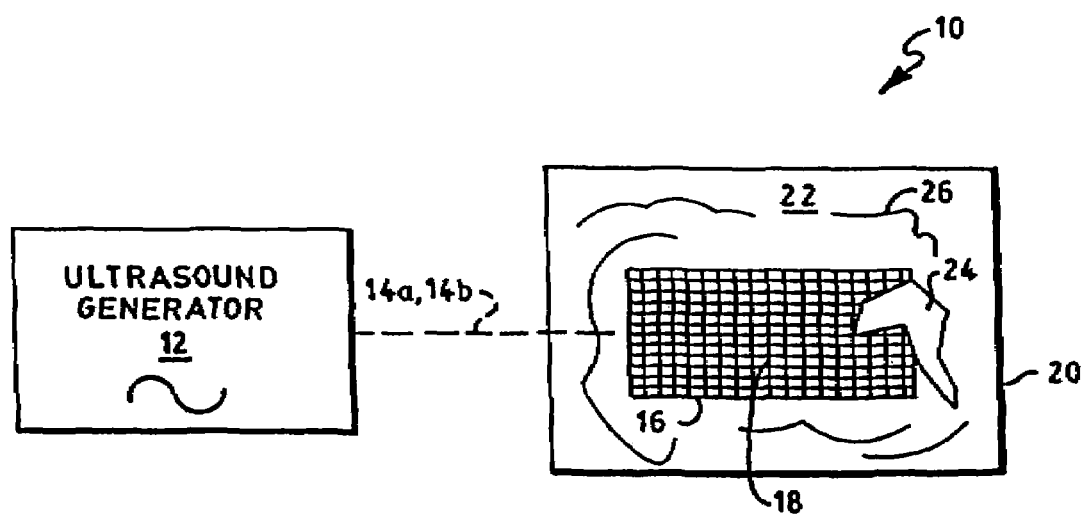
FIG. 2 shows a top view schematic of the system of FIG. 1.

FIGS. 1 and 2 show schematic side and top views, respectively, of an ultrasound processing system 10 constructed according to the invention. An ultrasonic generator 12 electrically connects, via electrical paths 14a, 14b, to an ultrasound transducer 16 to drive the transducer 16 at ultrasound frequencies above about 18 khz, and usually below 4 MHz. Though not required, the transducer 16 is shown in FIG. 1 as an array of transducer elements 18. Typically, such elements 18 are made from ceramic, piezoelectric, or magnetostrictive materials which expand and contract with applied voltages or current to create ultrasound. The transducer 16 is mounted to the bottom, to the sides, or within the ultrasound treatment tank 20 through conventional methods, such as known to those skilled in the art. A liquid ("process chemistry") 22 fills the tank to a level sufficient to cover the delicate part 24 to be processed and/or cleaned. In operation, the generator 12 drives the transducer 16 to create acoustic energy 26 that couples into the liquid 22.

Although the transducer 16 of FIGS. 1 and 2 is shown mounted inside the tank 20, those skilled in the art will appreciate that other mounting configurations are possible and envisioned. For example, an alternative configuration is to mount the transducer 16 to an outside surface of the tank 20, typically at the bottom 20a of the tank 20. The transducer elements 18 of the transducer 16 are of conventional design, and are preferably "clamped" so as to compress the piezoelectric transducer material.

Figure 3:
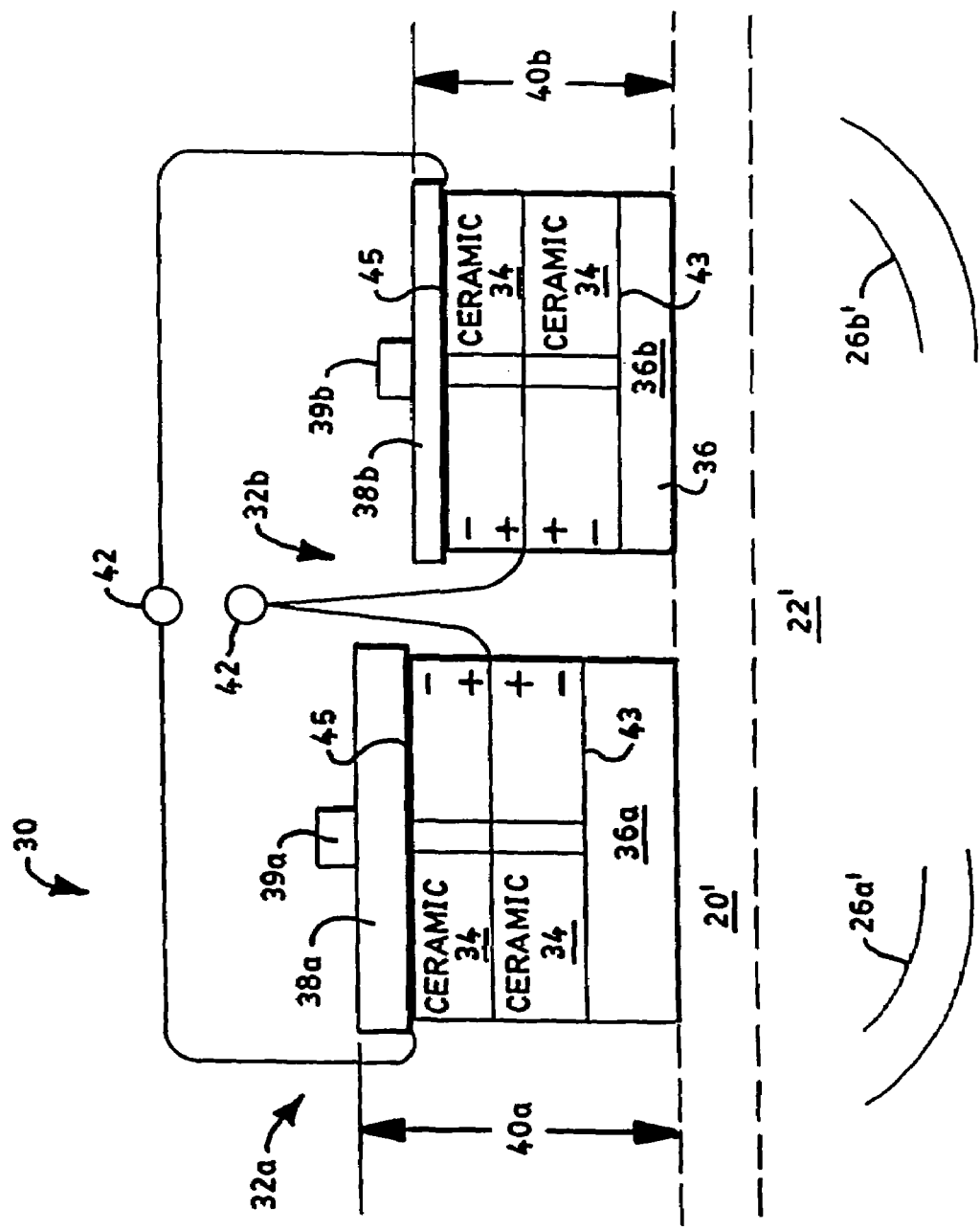
FIG. 3 shows a schematic illustration of a multi-transducer system constructed according to the invention and used to generate broadband ultrasound in a combined bandwidth.

FIG. 3 illustrates a two transducer system 30. Transducer 32a, 32b are similar to one of the elements 18, FIG. 1. Transducer 32a includes two ceramic sandwiched elements 34, a steel back plate 38a, and a front drive plate 36a that is mounted to the tank 20'. Transducer 32b includes two ceramic sandwiched elements 34, a steel back plate 38b, and a front drive plate 36b that is mounted to the tank 20'. Bolts 39a, 39b pass through the plates 38a, 38b and screw into the drive plates 36a, 36b, respectively, to compresses the ceramics 34. The transducers 32 are illustratively shown mounted to a tank surface 20'.

The transducers 32a, 32b are driven by a common generator such as generator 12 of FIG. 1. Alternatively, multiple generators can be used. The ceramics 34 are oriented with positive "+" orientations together or minus "−" orientations together to obtain cooperative expansion and contraction within each transducer 32. Lead-outs 42 illustrate the electrical connections which connect between the generator and the transducers 32 so as to apply a differential voltage there-across. The bolts 39a, 39b provide a conduction path between the bottoms 43 and tops 45 of the transducers 32 to connect the similar electrodes (here shown as "−" and "−") of the elements 34.

The length 40a, 40b of transducers 32a, 32b, respectively, determine the transducer's fundamental resonant frequency. For purposes of illustration, transducer 32a has a fundamental frequency of 40 khz, and transducer 32b has a fundamental frequency of 44 khz. Transducers 32a, 32b each have a finite ultrasound bandwidth which can be adjusted, slightly, by those skilled in the art. Typically, however, the bandwidths are about 4 khz. By choosing the correct fundamental frequencies, therefore, an overlap between the bandwidths of the two transducers 32a, 32b can occur, thereby adding additional range within which to apply ultrasound 26a', 26b' to liquid 22'.

Figure 4:
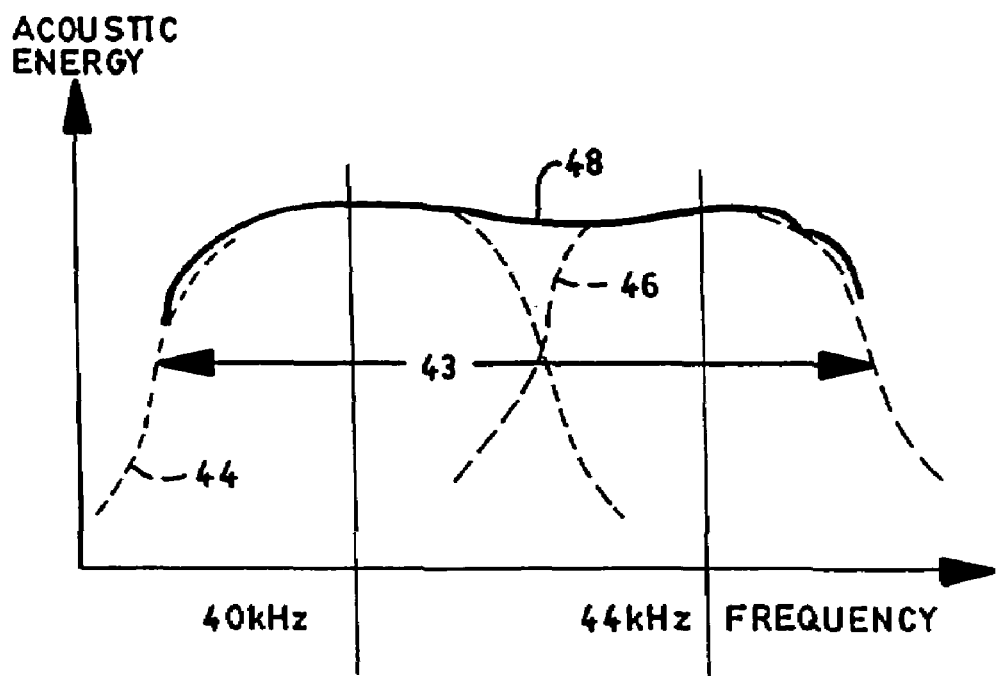
FIG. 4 graphically illustrates the acoustic disturbances produced by the two transducers of FIG. 3.

The acoustic energy 26' applied to the liquid 22' by the combination of transducers 32a, 32b is illustrated graphically in FIG. 4. In FIG. 4, the "x" axis represents frequency, and the "y" axis represents acoustical power. The outline 44 represents the bandwidth of transducer 32a, and outline 46 represents the bandwidth of transducer 32b. Together, they produce a combined bandwidth 43 which produces a relatively flat acoustical energy profile to the liquid 22', such as illustrated by profile 48. The flatness of the acoustic profile 48 within the bandwidth 43 is preferably within a factor of two of any other acoustic strength within the bandwidth 43. That is, if the FWHM (full width, half maximum) defines the bandwidth 43; the non-uniformity in the profile 48 across the bandwidth 43 is typically better than this amount. In certain cases, the profile 48 between the two bandwidths 44 and 46 is substantially flat, such as illustrated in FIG. 4.

The generator connected to lead-outs 42 drives the transducers 32a, 32b at frequencies within the bandwidth 43 to obtain broadband acoustical disturbances within the liquid 22'. As described herein, the manner in which these frequencies are varied to obtain the overall disturbance is important. Most preferably, the generator sweeps the frequencies through the overall bandwidth, and at the same time sweeps the rate at which those frequencies are changed. That is, one preferred generator of the invention has a "sweep rate" that sweeps through the frequencies within the bandwidth 43; and that sweep rate is itself varied as a function of time (a phenomenon denoted herein as "sweep the sweep rate"). In alternative embodiments of the invention, the sweep rate is varied linearly, randomly, and as some other function of time to optimize the process conditions within the tank 20'.

With further reference to FIGS. 1 and 2, each of the elements 18 can have a representative bandwidth such as illustrated in FIG. 4. Accordingly, an even larger bandwidth 43 can be created with three or more transducers such as illustrated by transducers 32a, 32b. In particular, any number of combined transducers can be used. Preferably, the bandwidths of all the combined transducers overlap provide an integrated bandwidth such as profile 48 of FIG. 4. As such, each transducer making up the combined bandwidth should have a unique resonant frequency.

Figure 5:
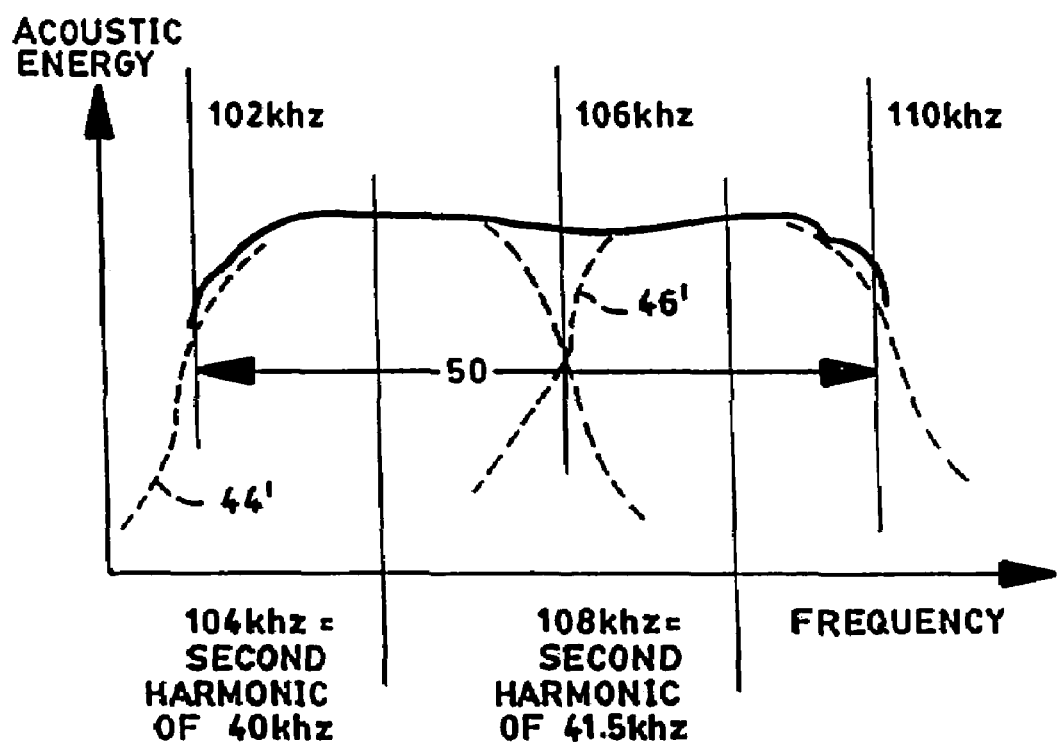
FIG. 5 graphically illustrates the broadband acoustic disturbances produced by harmonics of a multi-transducer system constructed according to the invention.

Those skilled in the art understand that each of the transducers 18 and 32a, 32b, FIGS. 1 and 3, respectively, have harmonic frequencies which occur at higher mechanical resonances of a primary resonant frequency. It is one preferred embodiment of the invention that such transducers operate at one of these harmonics, i.e., typically the first, second, third or fourth harmonic, so as to function in the frequency range of 100 khz to 350 khz (see, e.g., FIG. 5, which illustrates an applied ultrasonic bandwidth of 102 khz to 110 khz in a manner similar as in FIG. 4). This frequency range provides a more favorable environment for acoustic processes within the liquid 22, 22' as compared to low frequency disturbances less than 100 khz. For example, ultrasound frequencies around the 40 khz frequency can easily cause cavitation damage in the part 24. Further, such frequencies tend to create standing waves and other hot spots of spatial cavitation within the liquid.

FIGS. 6–10 illustrate alternative backplate configurations according to the invention. Unlike the configuration of FIG. 3, the backplates of FIGS. 6–10 are shaped to flatten or modify the power output from the entire transducer when driven over a range of frequencies such as shown in FIG. 4. Specifically, FIG. 6 includes a backplate 58 that, for example, replaces the backplate 38 of FIG. 3. A portion of the bolt 39 is also shown. As illustrated, the backplate 58 has a cut-away section 60 that changes the overall acoustic resonance of the transducer over frequency. Similarly, the backplate 58a of FIG. 7 has a curved section 60a that also changes the overall acoustic resonance of the transducer over frequency. FIGS. 8, 9 and 10 similarly have other sloped or curved sections 60b, 60c, and 60d, within backplates 58b, 58c and 58d, respectively, that also change the overall acoustic resonance of the transducer.

The exact configuration of the backplate depends upon the processing needs of the ultrasound being delivered to a tank. For example, it is typically desirable to have a flat or constant power over frequency, such as shown in FIG. 4. Accordingly, for example, the backplate and/or front driver can be cut or shaped so as to help maintain a constant power output such that the energy generated by the transducer at any given frequency is relatively flat over that bandwidth. Alternatively, the backplate can be cut or shaped so as to provide a varying power output, over frequency, such as to compensate for other non-linearities within a given ultrasound system.

Figure 17:
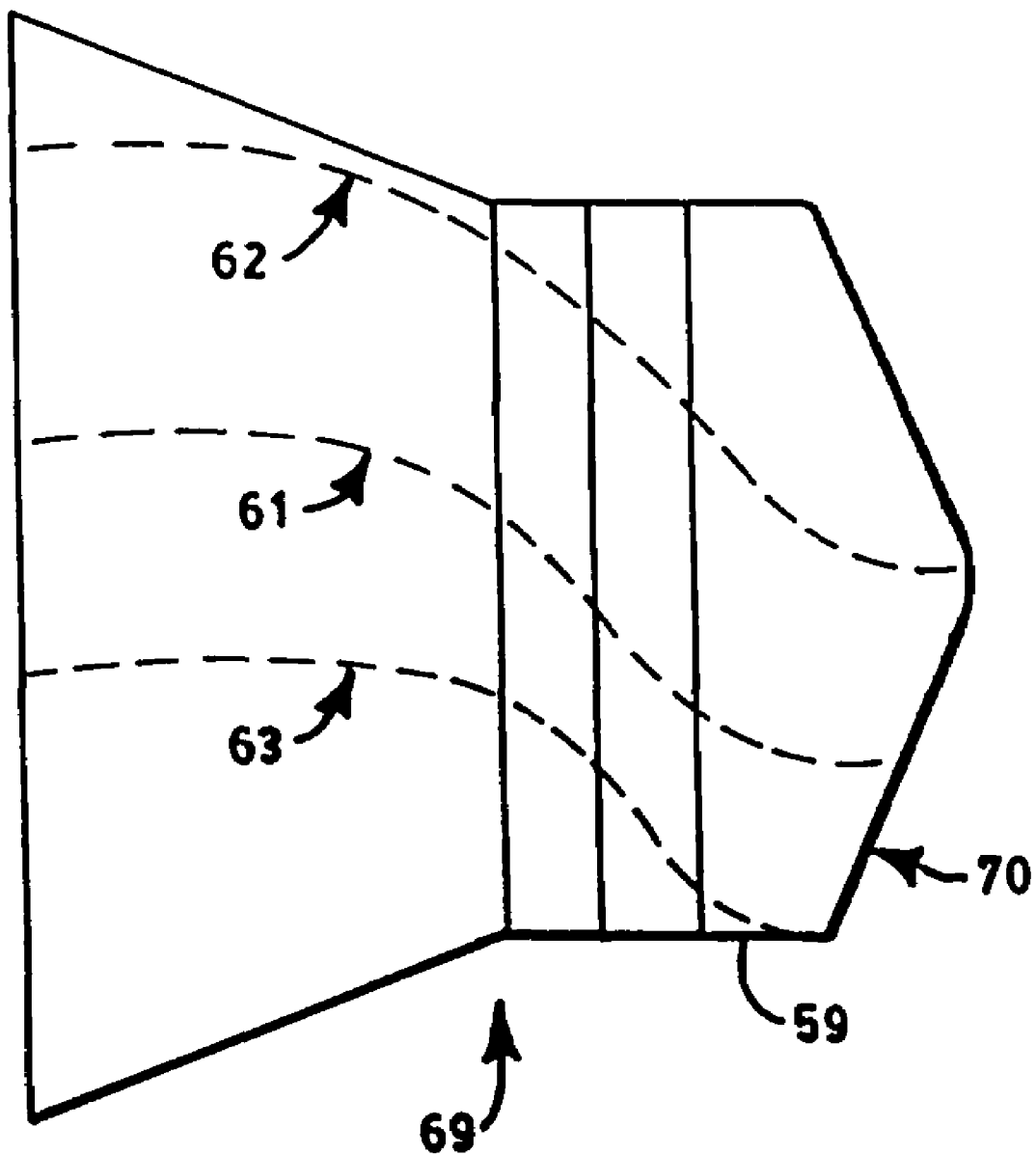
FIG. 17 shows representative standing waves within one transducer of the invention.

FIG. 17 illustratively shows how standing waves are formed within one transducer 69 of the invention over various frequencies 61, 62, 63. Because of the shaped surface 70 of the backplate 59,there are no preferred resonant frequencies of the transducer 69 as standing waves can form relative to various transverse dimensions of the transducer 69. By way of example, frequency 62 can represent 38 khz and frequency 63 can represent 42 khz.

FIG. 11 illustrates still another transducer 80 of the invention that provides for changing the power output as a function of frequency. The front driver 82 and the backplate 84 are connected together by a bolt 86 that, in combination with the driver 82 and backplate 84, compress the ceramics 88a, 88b. The configuration of FIG. 11 saves cost since the front driver 82 has a form fit aperture-sink 90 (the bolt head 86a within the sink 90 are shown in a top view in FIG. 12) that accommodates the bolt head 86a. A nut 86b is then screwed onto the other end of the bolt 86 and adjacent to the backplate 84 such that a user can easily access and remove separate elements of the transducer 80.

The front driver 82 and/or backplate 84 (the "backplate" also known as "back mass" herein) are preferably made from steel. The front driver 82 is however often made from aluminum. Other materials for the front driver 82 and/or the backplate 84 can be used to acquire desired performance characteristics and/or transducer integrity.

Figure 13:
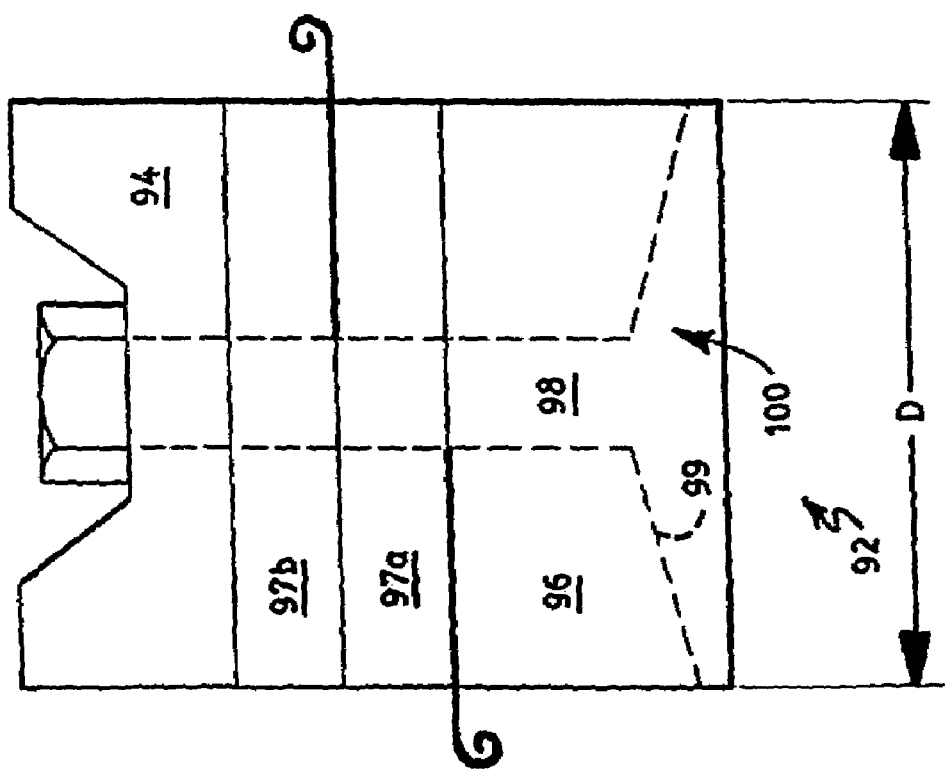

FIG. 13 shows another transducer 92 that includes a backplate 94 and a front driver 96. A bolt 98 clamps two ceramic elements 97a, 97b together and between the backplate 94 and driver 96; and that bolt 98 has a bolt head 100 that is approximately the same size as the diameter "D" of the transducer 92. The bolt head 100 assists the overall operation of the transducer 92 since there is no composite interface of the bolt 98 and the driver 96 connected to the tank. That is, the bond between the tank and the transducer 92 is made entirely with the bolt head 100. By way of comparison, the bond between the tank and the transducer 80, FIG. 11, occurs between both the bolt 86 and the driver 82. A sloped region 99 provides for varying the power output over frequency such as described herein.

Figure 14:
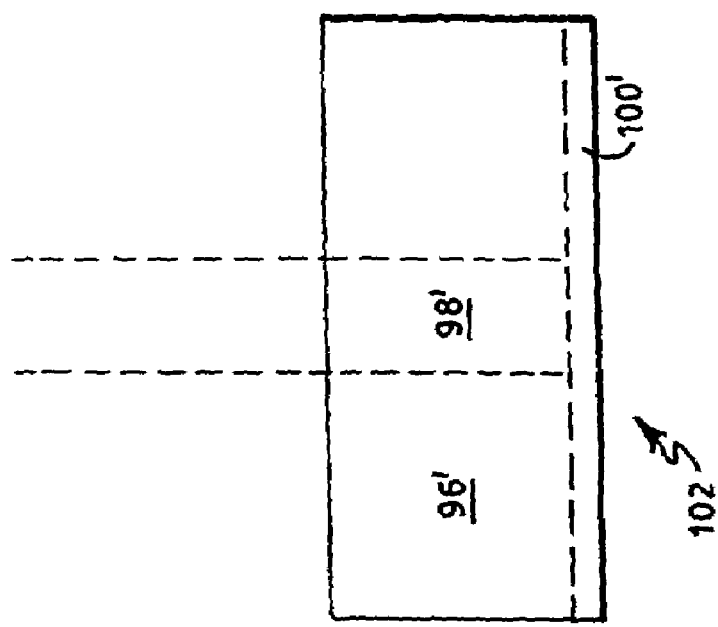

FIG. 14 illustrates one end 102 of a transducer of the invention that is similar to FIG. 13 except that there is no slope region 99; and therefore there is little or no modification of the power output from the transducer (at least from the transducer end 102).

Figure 16:
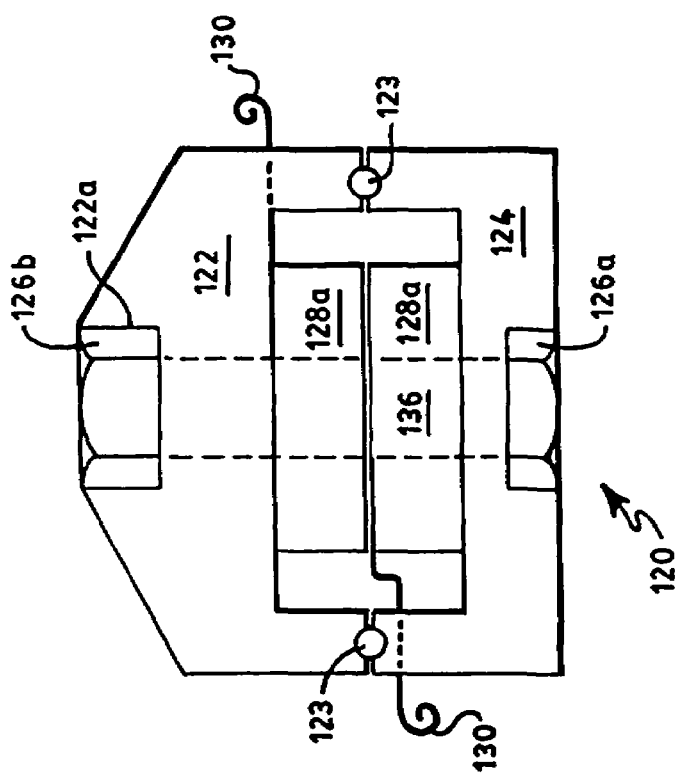
Figure 15:
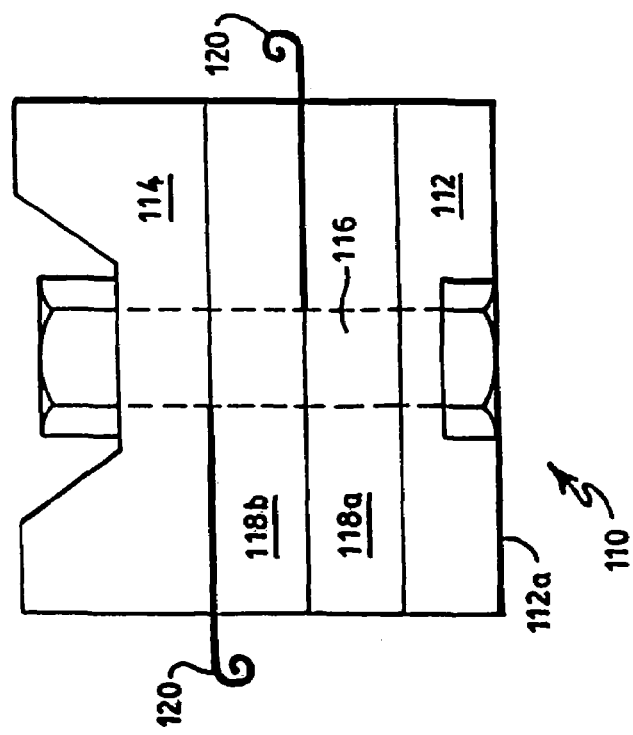

FIGS. 15 and 16 show further transducer embodiments of the invention. FIG. 15 shows a transducer 110 that includes a driver 112, backplate 114, bolt 116, ceramic elements 118a, 118b, and electrical lead-outs 120. The backplate is shaped so as to modify the transducer power output as a function of frequency. The driver 112 is preferably made from aluminum.

FIG. 16 illustrates an alternative transducer 120 that includes a backplate 122, driver 124, bolt 126, ceramic elements 128a, 128b, and lead outs 130. One or both of the backplate and driver 122, 124 are made from steel. However, the front driver 124 is preferably made from aluminum. The bolt head 126a is fixed within the driver 124; and a nut 126b is screwed onto the bolt 126 to reside within a cut-out 122a of the backplate 122. The backplate 122 and front driver 129 are sealed at the displacement node by an O-ring 123 to protect the electrical sections (i.e., the piezoelectric ceramics and electrodes) of the transducer 120 under adverse environmental conditions.

The designs of FIGS. 13–14 have advantages over prior art transducers in that the front plate in each design is substantially flush with the tank when mounted to the tank. That is, the front plates have a substantially continuous front face (e.g., the face 112a of FIG. 15) that mounts firmly with the tank surface. Accordingly, such designs support the tank surface, without gap, to reduce the chance of creating cavitation implosions that might otherwise eat away the tank surface and create unwanted contaminants.

Figure 18:
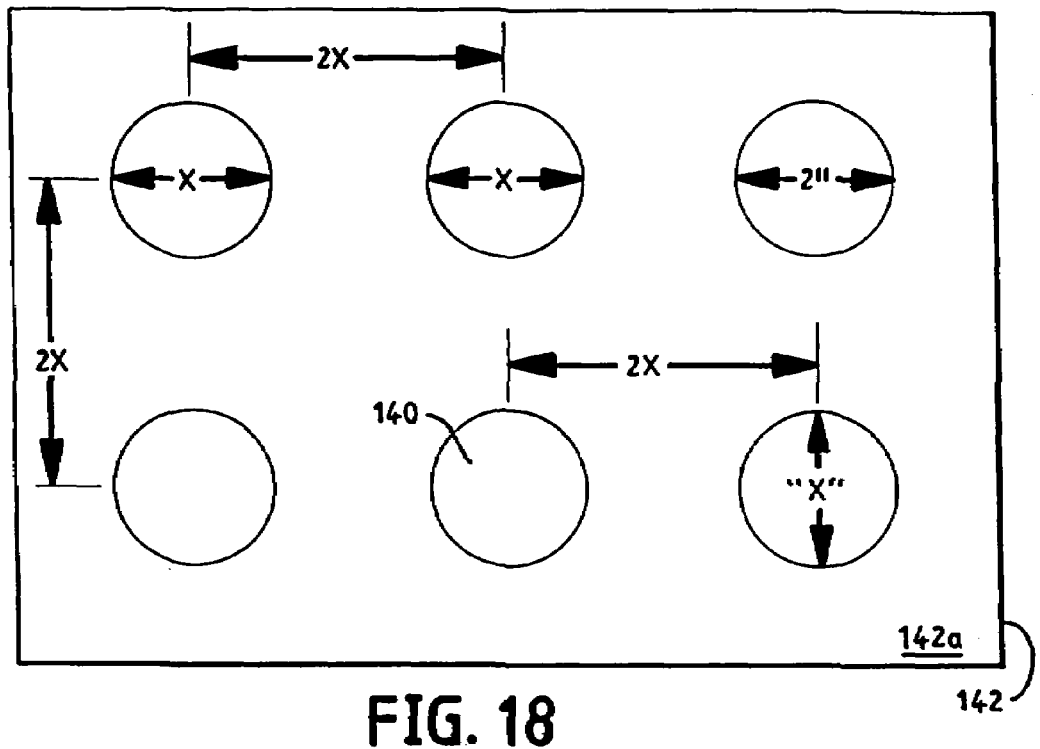
FIG. 18 illustrates preferential placement and mounting of multiple transducers relative to a process tank, in accord with the invention.
Figure 19:
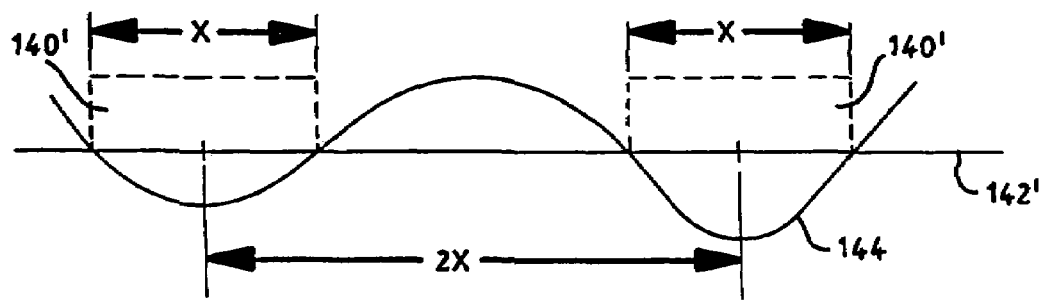
FIG. 19 illustrates a representative standing wave relative to the process tank as formed by the arrangement of FIG. 18.

FIG. 18 shows one preferred arrangement (in a bottom view) for mounting multiple transducers 140 to the bottom 142a of a process tank 142. Specifically, the lateral spacing between transducers 140—each with a diameter X—is set to 2X to reduce the cavitation implosions around the transduces 140 (which might erode the generally expensive tank surface 142a). By way of example, if the transducer 140 has a two inch diameter (i.e., X=2"), then the spacing between adjacent transducers 140 is four inches. Other sizes can of course be used and scaled to user needs and requirements. FIG. 9(d) illustrates, in a cross sectional schematic view, a standing wave 144 that is preferentially created between adjacent transducers 140' with diameters X and a center to center spacing of 2X. The standing wave 144 tends to reduce cavitation and erosion of the tank 142' surface.

Surface cavitation is intense cavitation that occurs at the interface between the solution within the tank and the radiating surface upon which the ultrasonic transducers are mounted. There are several problems associated with surface cavitation damage. First, it is often intense enough to erode the material of the radiating surface. This can eventually create a hole in the radiation surface, destroying the tank. The erosion is also undesirable because it introduces foreign materials into the cleaning solution. Surface cavitation further generates cavitation implosions with higher energy in each cavitation implosion than exists in the cavitation implosions in the process chemistry. If the cavitation implosions in the process chemistry are at the proper energy level, than there is the possibility that the higher energy cavitation implosions at the surface cavitation will cause pitting or craters in the parts under process. In addition, the energy that goes into creating the surface cavitation is wasted energy that is better used in creating bulk cavitation.

Figure 20:
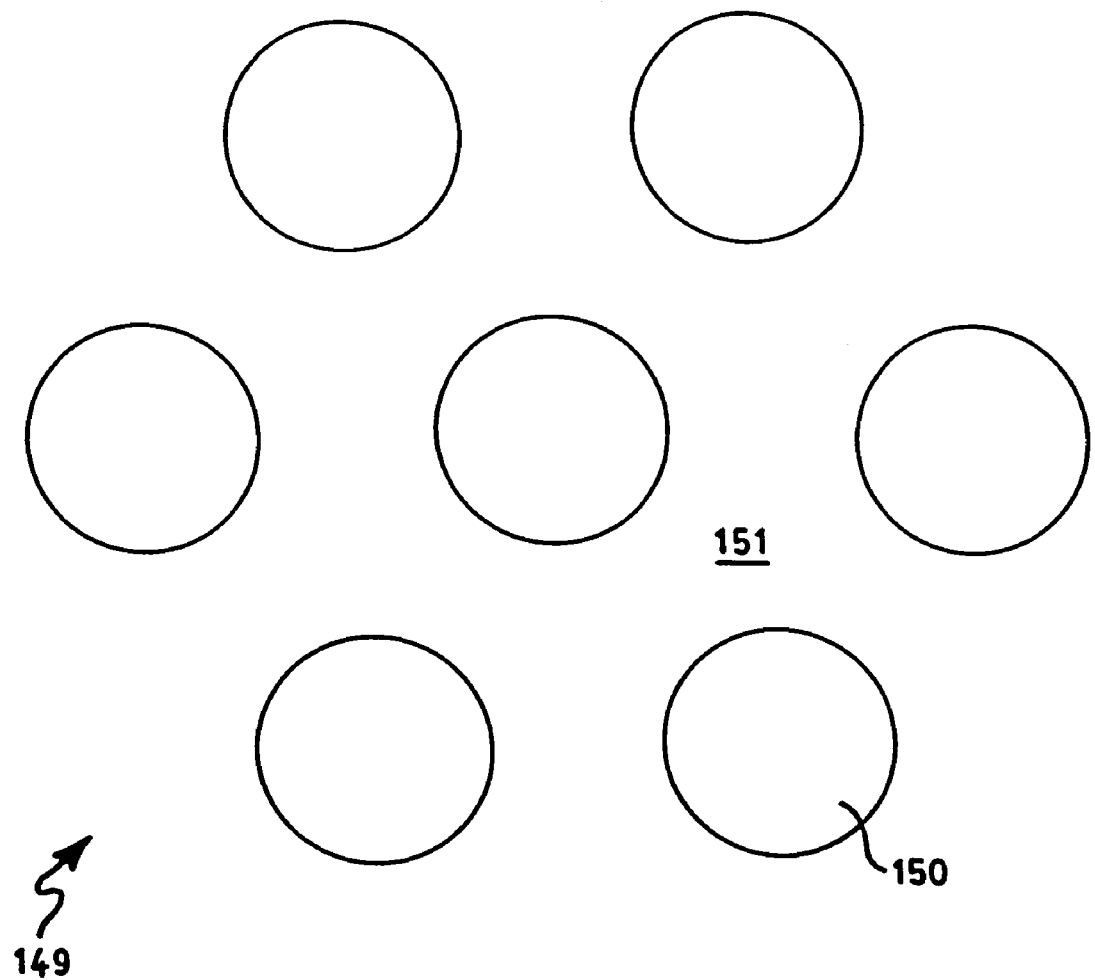
FIG. 20 illustrates another preferential pattern of placing transducers onto a mounting surface such as an ultrasound tank, in accord with the invention.
Figure 21:
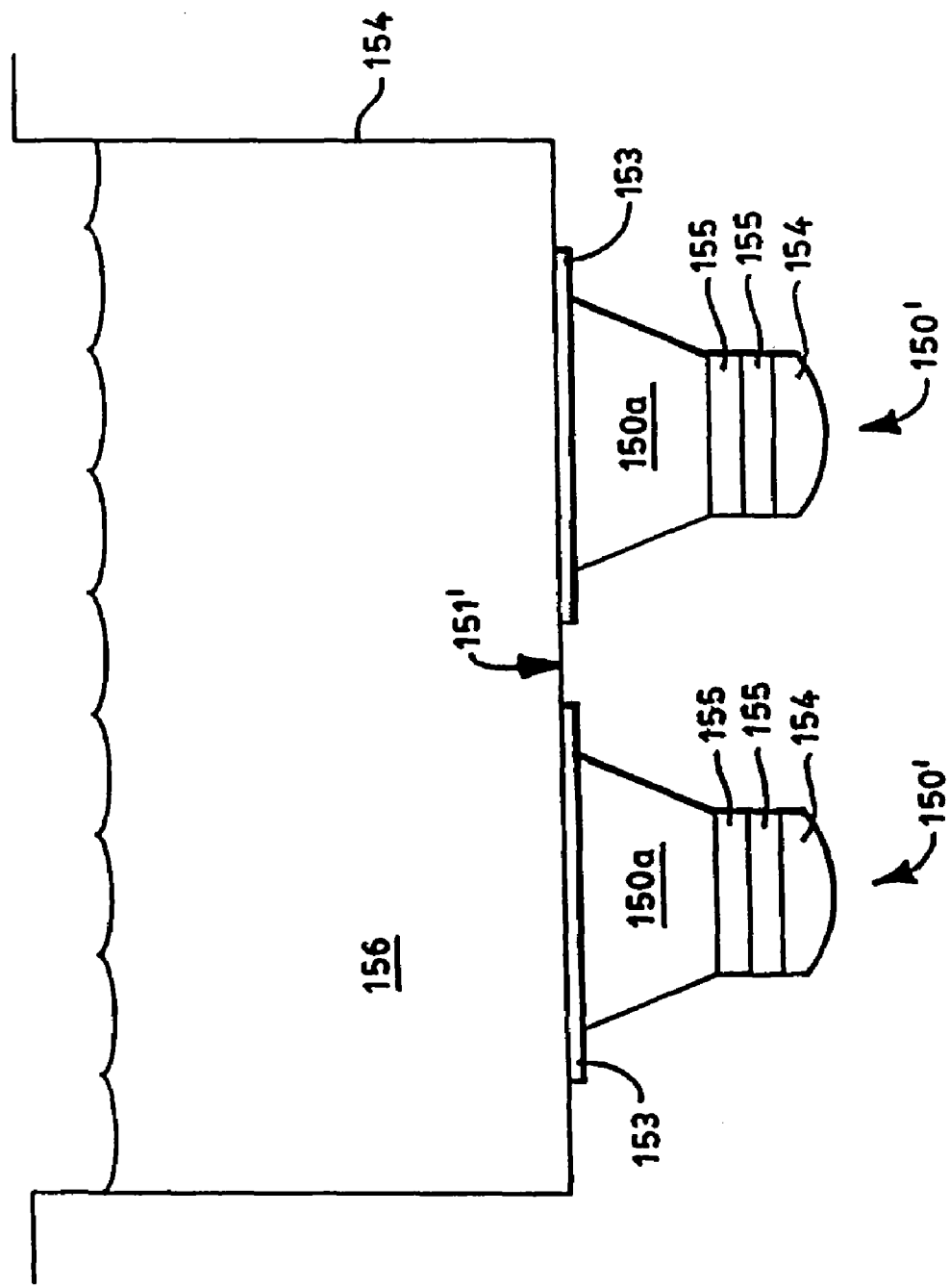
FIG. 21 illustrates, in a side view, the mounting of two transducers (such as the transducers of FIG. 20) to a tank, in accord with the invention.
Figure 22:
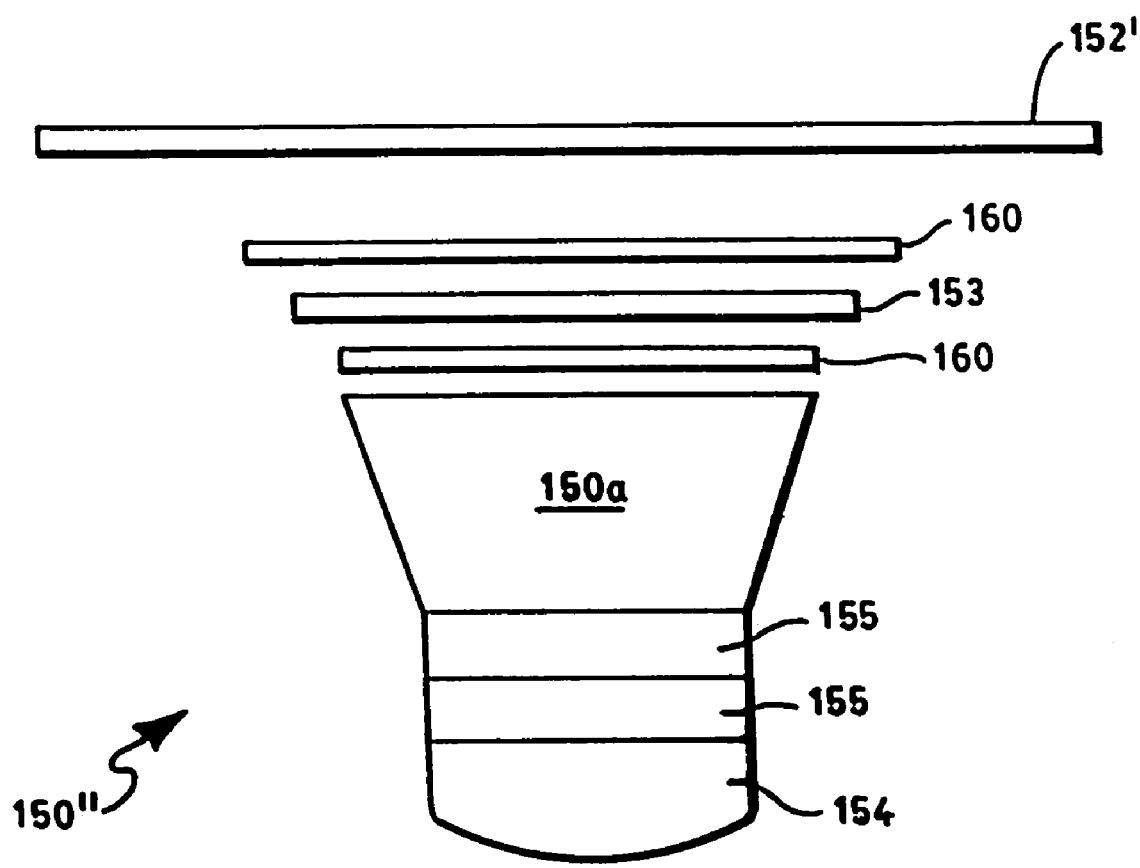
FIG. 22 shows an exploded side view of further features of one transducer such as shown in FIG. 21.

FIG. 20 illustrates a closed hex spacing pattern 149 of transducer elements 150 that causes the radiating membrane 151 (i.e., the surface of the tank to which the elements are bonded to) to vibrate in a sinusoidal pattern such that surface cavitation is prevented or reduced. In a side view, FIG. 21 illustrates a G-10 isolator 153 bonded between two of the transducers 150' (and specifically the front driver 150a) and the radiating surface 151', i.e., the wall of the tank 154 holding the process chemistry 156. The G-10 153 operates to further reduce unwanted surface cavitation, often times even when the closed hex spacing pattern of FIG. 20 is not possible. Piezoelectric elements 155 are sandwiched between the front plate 150a and backplate 154. FIG. 22 shows an exploded side view of one of the G-10 mounted transducer 150" of FIG. 21. Layers of epoxy 160 preferably separate the G-10 isolator 153 from the transducer 150' and from the surface 152'.

Most ultrasonic processes, including cleaning, have two distinct stages. The first stage is usually preparation of the liquid and the second stage is the actual process. The system 200 of FIGS. 23–25 reduces the time for liquid preparation and accomplishes the task to a degree where shorter process times are possible.

Figure 23:
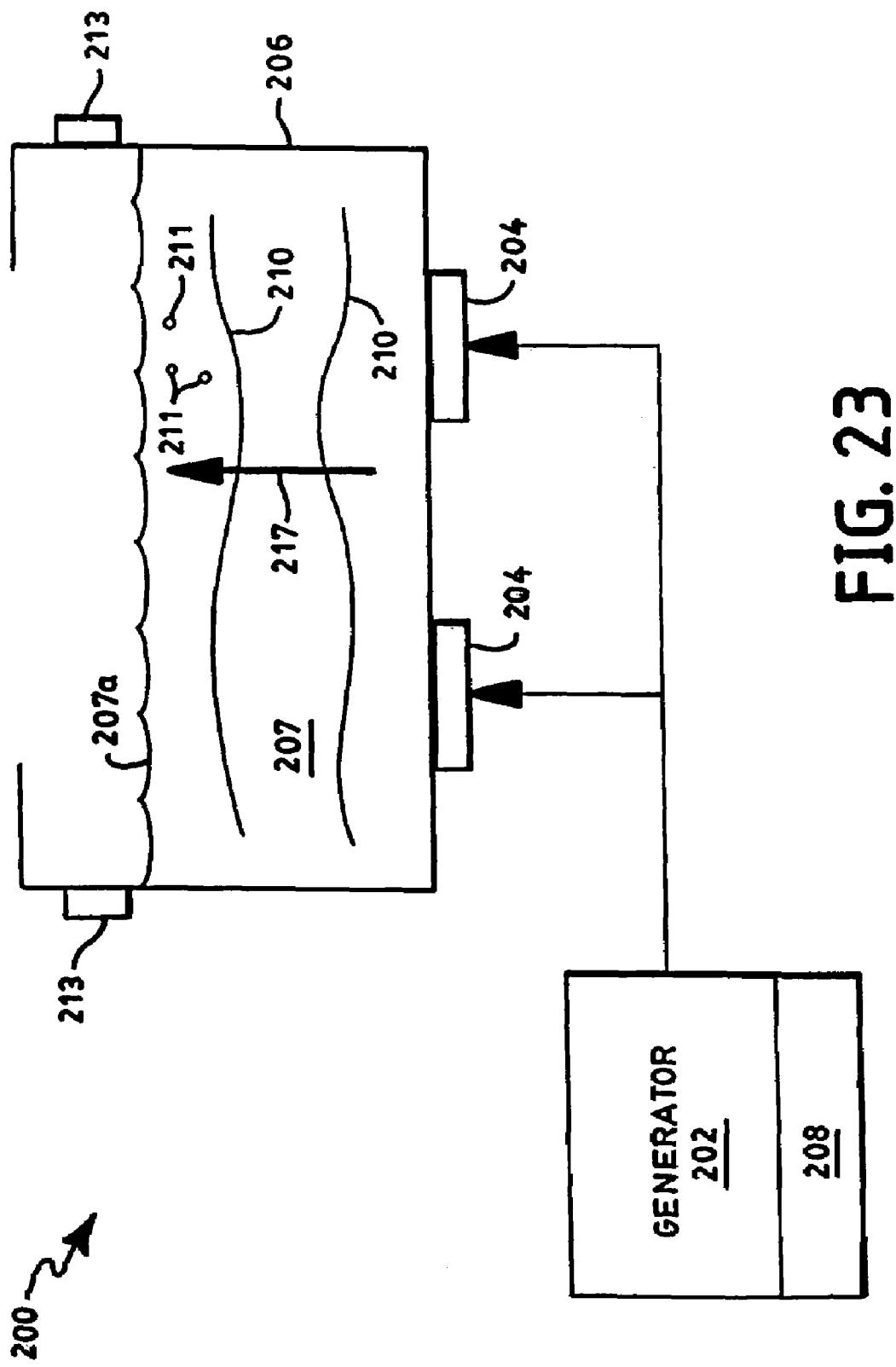
FIG. 23 illustrates a two stage ultrasound delivery system constructed according to the invention.
Figure 26:
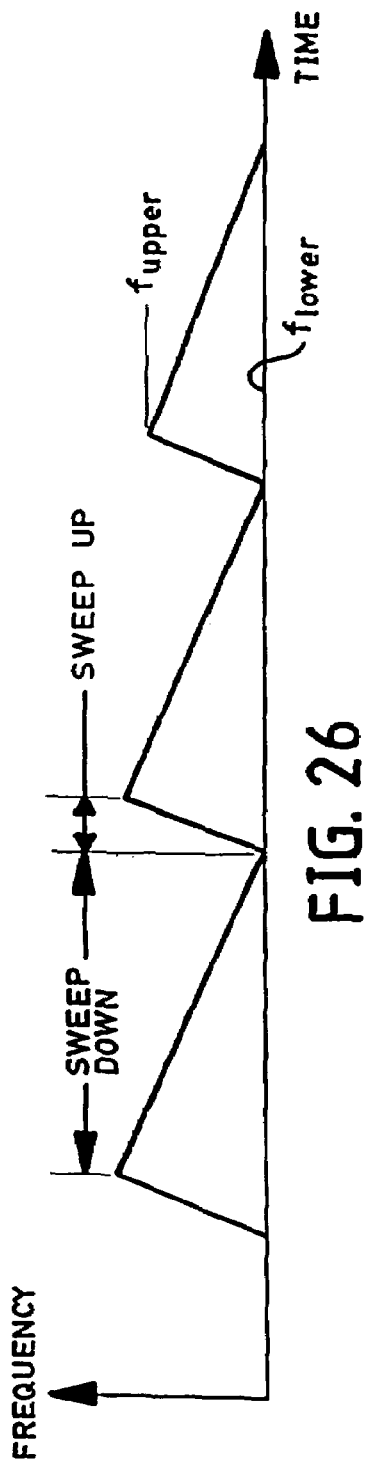
FIGS. 26–30 show alternate sweep down cyclical patterns for applying a power-up sweep pattern in accord with the invention.
Figure 27:
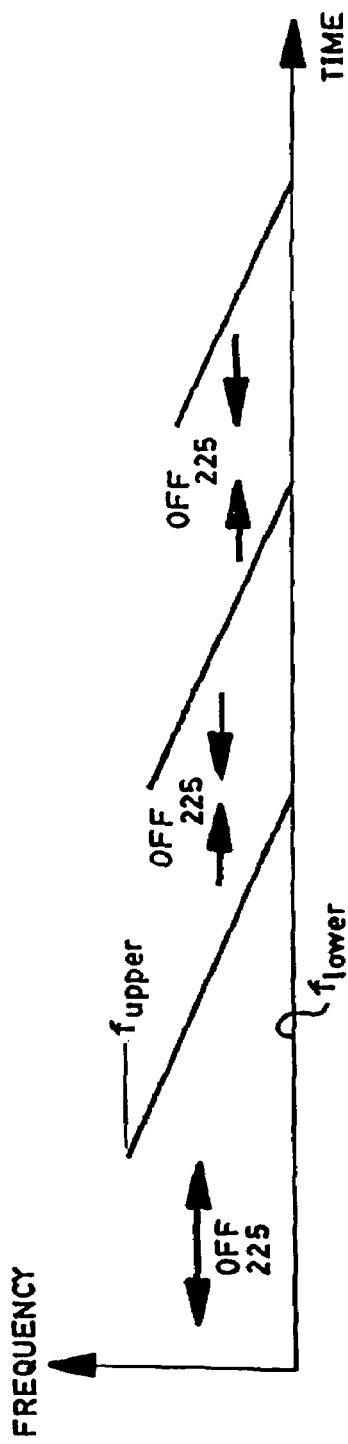

The invention of FIG. 23 utilizes the sound fields as an upward driving force to quickly move contaminants to the surface 207a of the liquid 207. This phenomenon is referred to herein as "power up-sweep" and generally cleans the liquid more quickly and thoroughly so that part processing can be done with less residual contamination.

More particularly, FIG. 23 shows a system 200 constructed according to the invention. A generator 202 drives a plurality of transducers 204 connected to a process tank 206, which holds a process chemistry 207. The generator 202 drives the transducers 204 from an upper frequency ($f_{upper}$) to a lower frequency ($f_{lower}$), a shown in FIG. 25. Once $f_{lower}$ is reached, a frequency control subsystem 208 controls the generator 202 so as to drive the transducers 204 again from $f_{upper}$ to $f_{lower}$ and without driving the transducers from $f_{lower}$ to $f_{upper}$. In this manner, only decreasing frequencies are imparted to the process chemistry 207; and acoustic energy 210 migrates upwards (along direction 217), pushing contamination 211 upwards and out of the tank 206.

As shown in FIG. 24, the two stage ultrasonic processing system 200 can alternatively cycle the transducers 204 from $f_{upper}$ to $f_{lower}$ every other half cycle, with a degas, quiet or off half cycle 222 between each power burst. The control subsystem 208 of this embodiment thus includes means for inhibiting the flow of energy into the tank 206 over a second half cycle so that the quiet period 222 is realized. It is not necessary that the time periods of the first and second one-half cycles 222a, 222b, respectively, be equal.

FIGS. 24 and 25 also show that the rate at which the frequencies are swept from $f_{upper}$ to $f_{lower}$ can vary, as shown by the shorter or longer periods and slope of the power bursts, defined by the frequency function 220.

The generator 202 preferably produces frequencies throughout the bandwidth of the transducers 204. The generator 202 is thus preferably a sweep frequency generator (described in U.S. Pat. Nos. 4,736,130 and 4,743,789) or a dual sweep generator (described in International Patent Application PCT/US97/12853) that will linearly or non-linearly change frequency from the lowest frequency in the bandwidth to the highest frequency in the bandwidth; and that will thereafter reverse direction and sweep down in frequency through the bandwidth. The invention of FIG. 25 has an initial stage where the sweeping frequency only moves from the highest bandwidth frequency to the lowest bandwidth frequency. Once the lowest frequency is reached, the next half cycle is the highest frequency and the sweep starts again toward the lowest frequency. An alternative (FIG. 24) is to shut the ultrasonics off when the lowest frequency is reached and reset the sweep to the highest frequency. After an ultrasonics quiet period 222, another sweep cycle from high frequency to low frequency occurs. This "off" period followed by one directional sweep is repeated until contamination removal is complete; and then the processing can start in a normal way. Alternatively, a power up-sweep mode can be utilized for improved contamination removal during processing.

The reason that contamination is forced to the surface 207a of the process chemistry 207 in the system of FIG. 23 is because the nodal regions move upward as frequency is swept downward. Contamination trapped in nodal regions are forced upward toward the surface as nodes move upward. Generally, the system of FIG. 23 incorporates a type of frequency modulation (FM) where frequency changes are monotonic from higher to lower frequencies. Transducers 204 mounted to the bottom of the process tank 206 generate an ever expanding acoustic wavelength in the upward direction 217 (i.e., toward the surface 207a of the process chemistry 207). This produces an acoustic force 210 which pushes contamination 211 to the surface 207a where the contamination 211 overflows the weirs 213 for removal from the tank 206.

Those skilled in the art should appreciate that methods and systems exist for sweeping the applied ultrasound energy through a range of frequencies so as to reduce resonances which might adversely affect parts within the process chemistry. See, e.g., U.S. Pat. Nos. 4,736,130 and 4,743,789 by the inventor hereof and incorporated by reference. It is further known in ultrasonic generators to "sweep the sweep rate" so that the sweep frequency rate is changed (intermittently, randomly, with a ramp function, or by another function) to reduce other resonances which might occur at the sweep rate. By way of example, the inventor of this application describes such systems and methods in connection with FIGS. 3, 4, 5A, 5B, 12A, 12B and 12C of International Application No. PCT/US97/12853, which is herein incorporated by reference.

Figure 28:
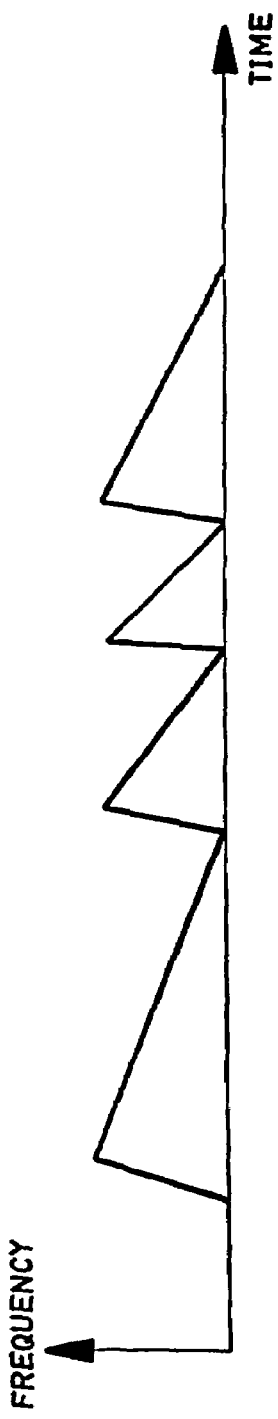

The variable slope of the frequency function 220 of FIGS. 24 and 25 illustrates that the time period between successive power up sweeps, from $f_{upper}$ to $f_{lower}$, preferably changes so as to "sweep the sweep rate" of the power up sweep. Accordingly, the power up-sweep preferably has a non-constant sweep rate. There are several ways to produce a non-constant power up-sweep rate, including:

(a) As illustrated in FIG. 28, sweep down in frequency (i.e., from $f_{upper}$ to $f_{lower}$) at a relatively slow rate, typically in the range of 1 Hz to 1.2 khz, and sweep up in frequency (i.e., from $f_{lower}$ to $f_{upper}$) during the recovery time at a rate about ten times higher than the sweep down frequency rate. Vary the rate for each cycle. This cycle is repeated during processing.

Figure 29:
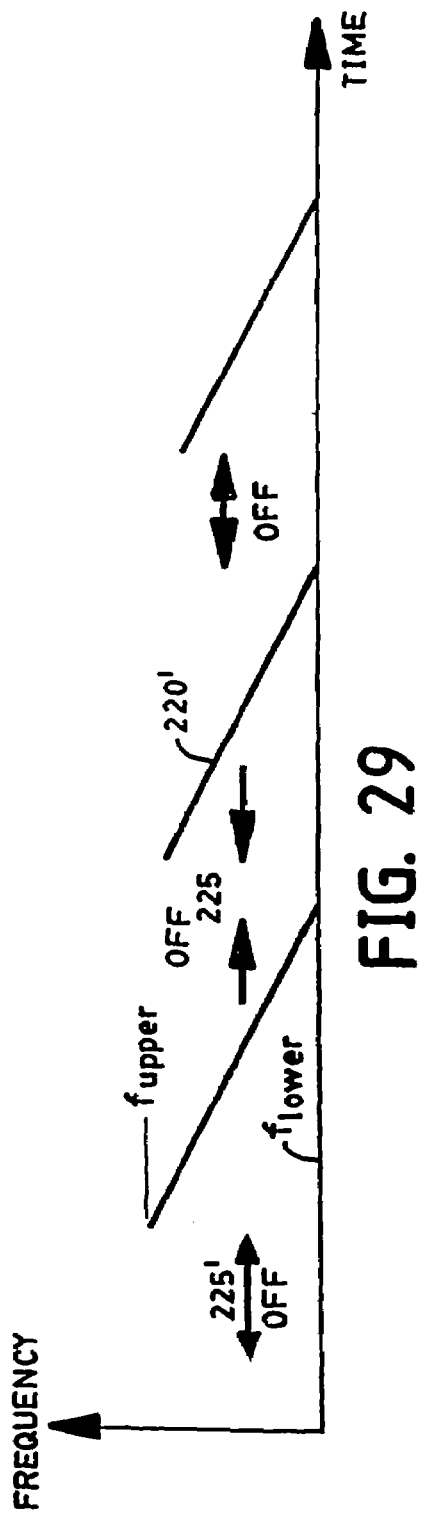

(b) As illustrated in FIG. 29, sweep down in frequency at a relatively slow rate and shut the generator 202 off (such as through the control subsystem 208) at periods 225' when the lowest frequency $f_{lower}$ in the bandwidth (bandwidth=$f_{upper}-f_{lower}$) is reached. During the off time 225', a degassing period 222 can occur as in FIG. 24 due to buoyancy of the gas bubbles; and the subsystem 208 resets the generator 202 to the highest frequency for another relatively slow rate of sweeping from $f_{upper}$ to $f_{lower}$, each time reducing contaminants. Vary the time of the degas period. Repeat this cycle during processing.

(c) As a function of time, change or "sweep" the power up-sweep rate at optimum values (1 Hz to 1.2 khz) of the rate, as shown in FIG. 28. The change in the upward sweep rate and the change in the downward sweep rate can be synchronized or they can be random with respect to one another.

(d) For the case where there is a degas period, as in FIGS. 24 and 29 (i.e. the recovery period when the generator is off or unconnected while resetting from low frequency to high frequency), vary the length of the degas period 222 (FIG. 24), 225' (FIG. 29) randomly or as a function of time such as through a linear sweep rate time function. This technique has an advantage for cases where there is one optimum power up-sweep rate (i.e., the rate of frequency change between $f_{upper}$ and $f_{lower}$) and, accordingly, low frequency resonances are eliminated by changing the overall rate. In such a technique, the slope of the frequency function 220' in FIG. 29, is constant, though the period of each degas period 225' changes according to some predefined function.

Figure 30:
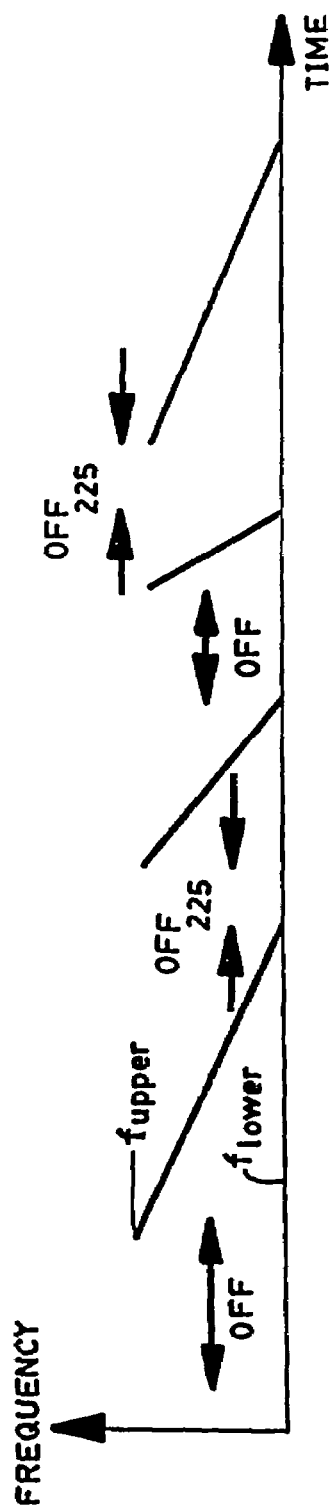

(e) As shown in FIG. 30, sweep the rate with a combination of (c) and (d) techniques above.

Note that in each of FIGS. 24–30, the x axis represents time (t) and the y axis represents frequency f.

Figure 31A:
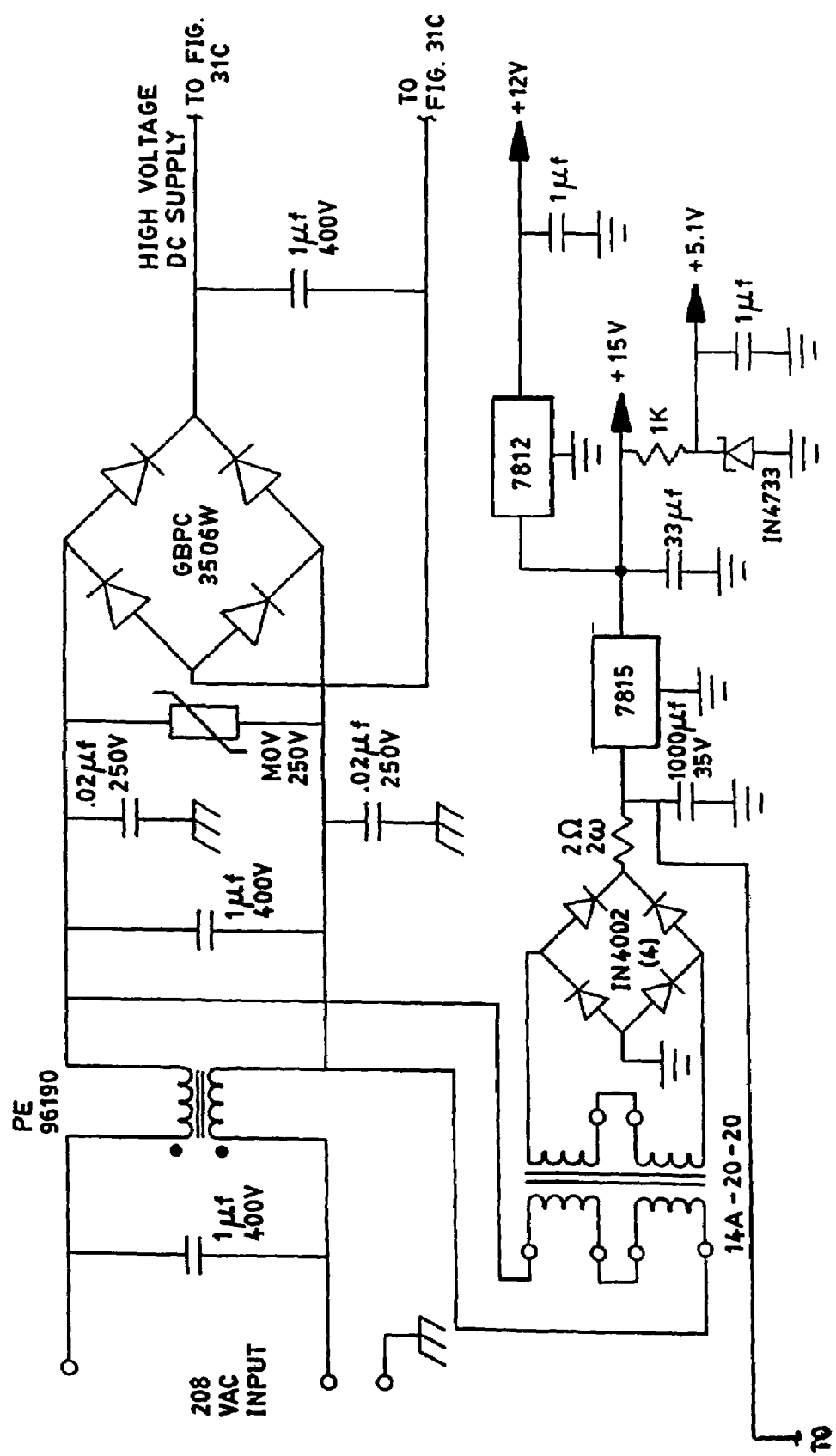
FIG. 31 schematically illustrates ultrasound generator circuitry for providing dual sweeping power-up sweep and variable degas periods, in accord with the invention.
Figure 31B:
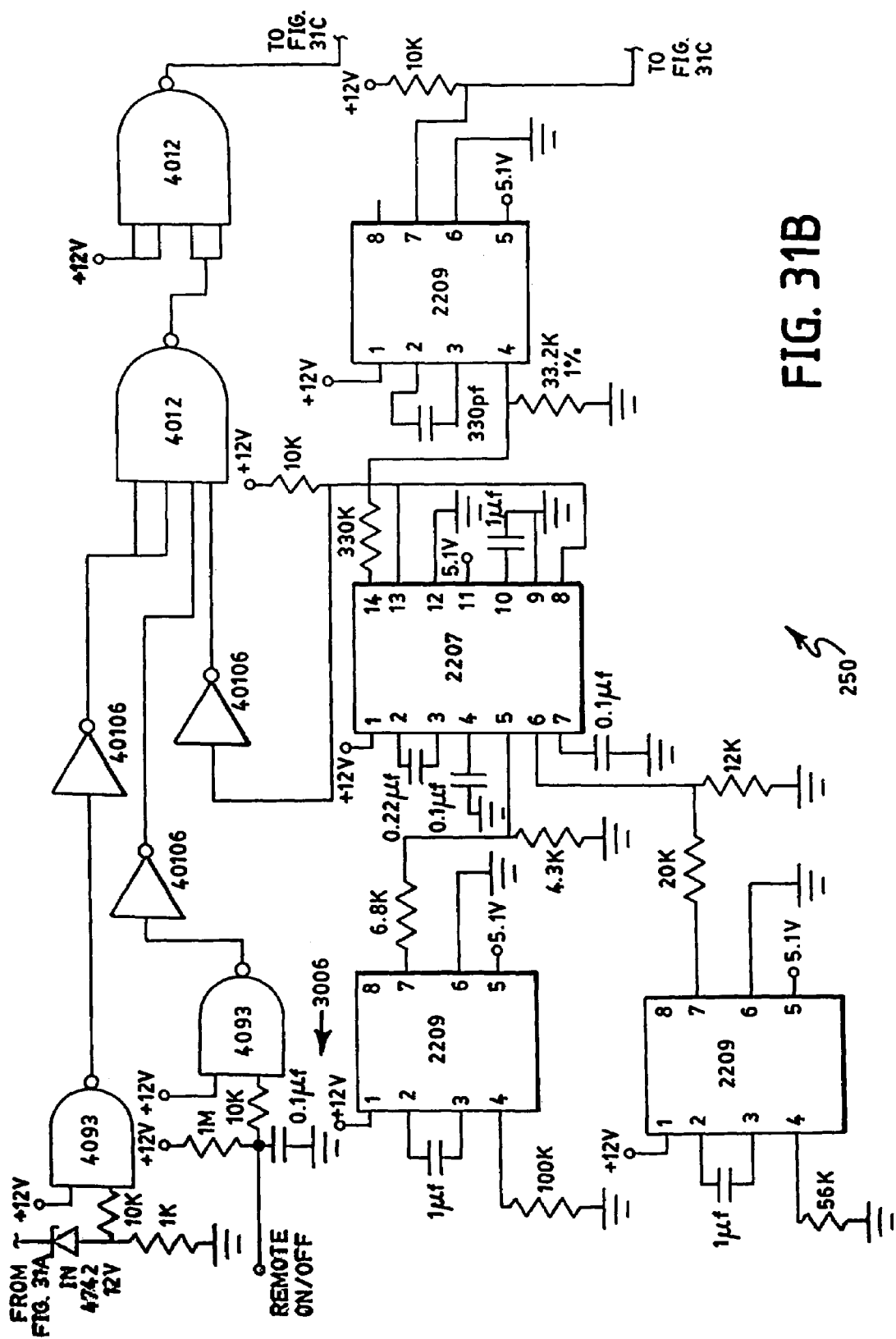

FIG. 31 shows a schematic 250 illustrating the most general form of generator circuitry providing both non-constant power up-sweep rate and non-constant degas period, as described above.

Extraction Tool Analysis

When evaluating one ultrasonic cleaner versus another as to its usefulness as an extraction tool, the slope between the first two points and the magnitude of the initial point are meaningful if the parts being extracted start out with identical contamination. If not, the results can be misleading. For example, consider two cleaners (e.g., tanks) that each remove 90% of the contamination on each trial. If cleaner A is tested with a part starting with 10,000 particles of contamination, point #1 will be 9,000 and point #2 will be 900. The slope is 8,100. Now if cleaner B is tested with a part starting with 1,000 particles, point #1 will be 900 and point #2 will be 90. Cleaner B thus has a slope of 810, which is ten times less than for cleaner A in removing the same percentage of contamination per run.

A preferred technique of the invention is to measure the slopes when the points are plotted on semi-log paper or to calculate log (count #1)—log (count #2) and compare figures between tanks. Since log (count #1)—log (count #2) equals log (count #1/count #2), a similar result is obtained if you compare the quotient of count #1 divided by count #2 for each cleaner.

The magnitude of the initial point does not provide significant information. However, the semi-log slope permits determining initial contamination count as long as the extraction time for each trial is short enough so the first three points are in a straight line. This line is extended back to the y-axis where x=0 to get the initial contamination count.

To evaluate two extraction tools, experimentation leads to a trail time that provides three points with each tool on a straight line when plotted on semi-log paper. For each tool, E for extraction is then calculated as log (count #1)—log (count #2). The tool with the largest E is the best.

The procedure for evaluating part cleanliness may be different than for evaluating tools, such that the magnitude of point #1 is now significant. However, the technique can be similar: choose a trial time to give three points in a straight line on semi-log paper; extrapolate back to the y-axis to get the initial number of particles on the part; continue trials until the count levels off or becomes zero (minus infinity on a semi-log plot); if the count became zero, there is no erosion, therefore, add together all the particles removed and subtract this from the extrapolated initial number of particles, indicating the remaining contamination count on the part; if the count leveled off to an erosion level, calculate the remaining contamination on the part by the formula:

$$C = (y\text{-}axis_{intercept}) - \sum_{i=1}^{n} trialcount_i + nx$$

where x=the erosion count per trial and n=the number of trials

The above analysis now provides the amount of contamination initially on the part (y-axis intercept), the contamination generated by erosion (nx), and the remaining contamination (C) on the part after all the extractions.

The energy in each cavitation implosion is the single most important characteristic of a high intensity ultrasonic field in a liquid used for cleaning or processing delicate parts. This energy value changes with chemistry characteristics, liquid temperature, and pressure and frequency of the ultrasound. Setting the center frequency of the ultrasonic generator to specific values over a wide range is the most practical way to choose the appropriate energy in each cavitation implosion for a given process. The invention of FIG. 32 provides this function with a single generator.

Figure 32:
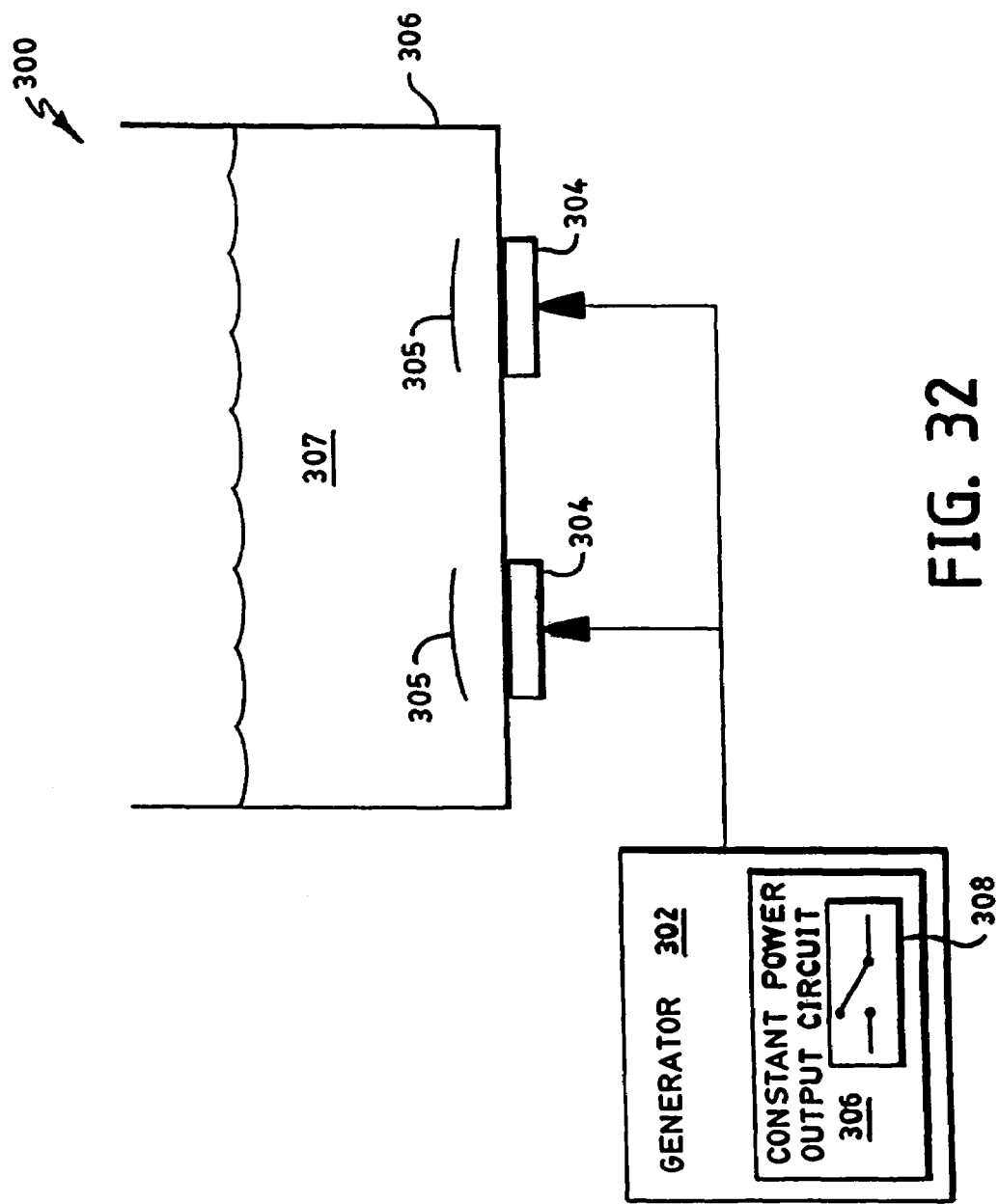
FIGS. 32 and 33 show multi-frequency ultrasound systems constructed according to the invention.

Specifically, FIG. 32 shows a system 300 including a generator 302 and transducers 304 that can be switched, for example, to either 72 khz or 104 khz operation. The transducers 304 operate to inject sonic energy 305 to the process chemistry 307 within the tank 306. Because of the impedance characteristics at these frequencies, the generator 302 includes a constant power output circuit 306 that changes the center frequency output from the generator 302 while maintaining constant output power. The circuit 306 includes a switch section 308 that switches the output frequency from one frequency to the next with no intermediate frequencies generated at the output (i.e., to the transducers 304).

Figure 33:
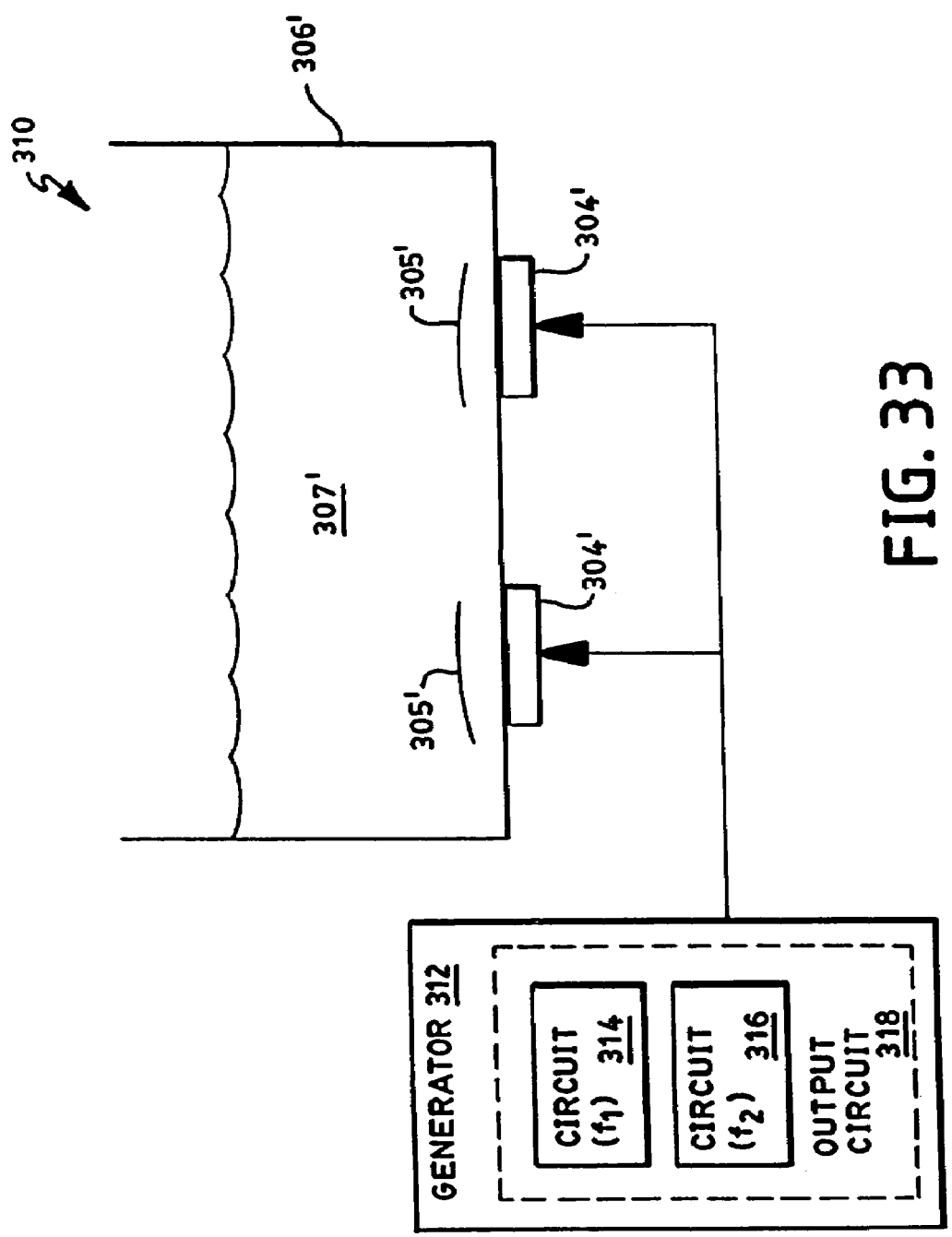

A similar system 310 is shown in FIG. 33, where switching between frequencies does not utilize the same power circuit. In FIG. 33, the generator 312 includes at least two drive circuits for producing selected frequencies $f_1$ and $f_2$ (these circuits are illustratively shown as circuit ($f_1$), item 314, and circuit ($f_2$), item 316). Before the reactive components in either of the circuits 314, 316 can be switched to different values, the output circuit 318 shuts down the generator 312 so that stored energy is used up and the relay switching occurs in a zero voltage condition.

From the above, one skilled in the art should appreciate that the system 310 can be made for more than two frequencies, such as for 40 khz, 72 khz and 104 khz. Such a system is advantageous in that a single transducer (element or array) can be used for each of the multiple frequencies, where, for example, its fundamental frequency is 40 khz, and its first two harmonics are 72 khz and 104 khz.

An alternative system is described in connection with FIG. 61.

Figure 34:
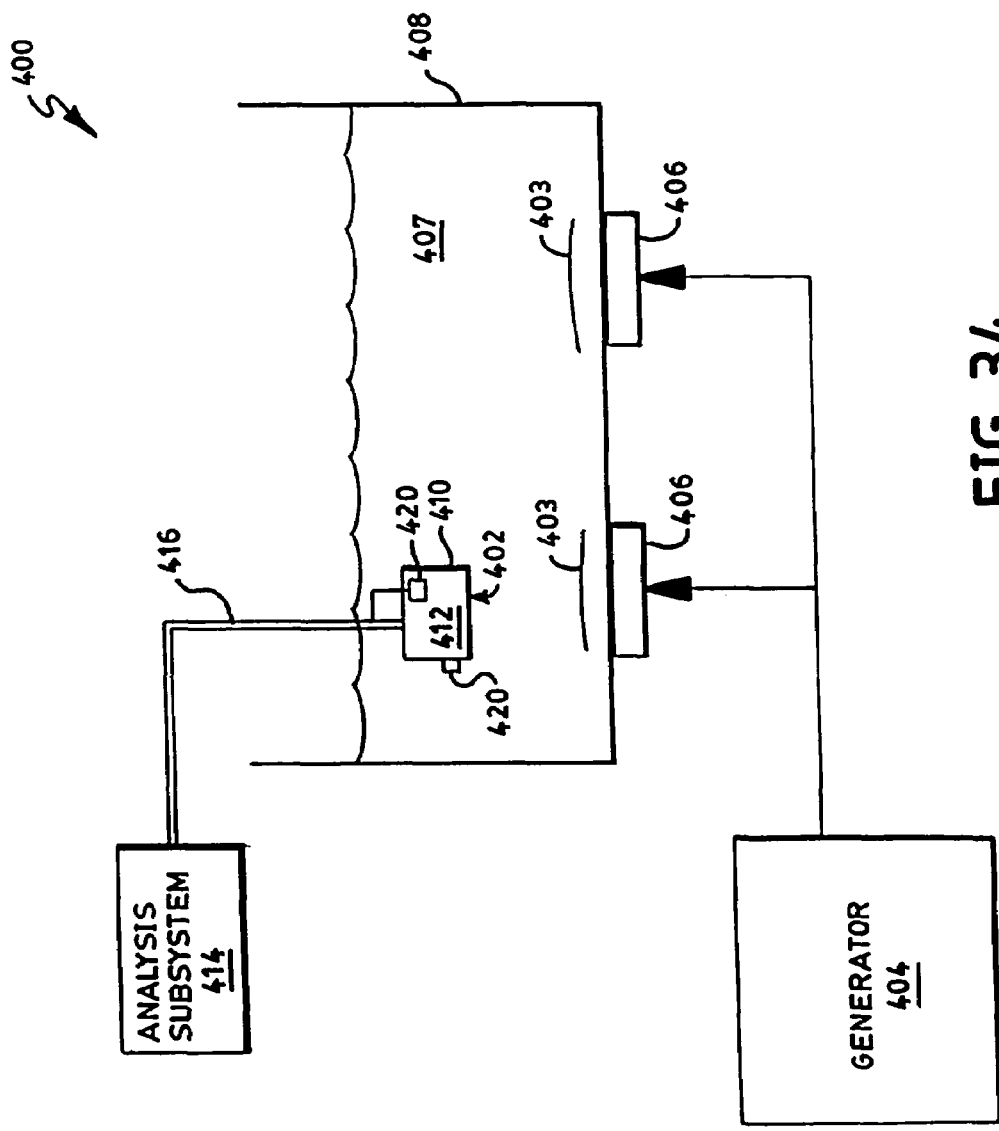
FIG. 34 illustrates a process control system and ultrasound probe constructed according to the invention.

FIG. 34 illustrates a system 400 and process probe 402 constructed according to the invention. A generator 404 connects to transducers 406 to impart ultrasonic energy 403 to the process chemistry 407 within the tank 408. The probe 402 includes an enclosure 410 that houses a liquid 412 that is responsive to ultrasound energy within the liquid 407. The enclosure 410 is made from a material (e.g., polypropylene) that transmits the energy 403 therethrough. In response to the energy 403, changes in or energy created from liquid 412 are sensed by the analysis subsystem 414. By way of example, the liquid 412 can emit spectral energy or free radicals, and these characteristics can be measured by the subsystem 414. Alternatively, the conduit 416 can communicate electrical energy that indicates the conductivity within the enclosure. This conductivity provides an indication as to the number of cavitation implosions per unit volume within the process chemistry 407. The conduit 416 thus provides a means for monitoring the liquid 412. A thermocouple 420 is preferably included within the enclosure 410 and/or on the enclosure 410 (i.e., in contact with the process chemistry 407) so as to monitor temperature changes within the enclosure 410 and/or within the process chemistry 407. Other characteristics within the tank 408 and/or enclosure 410 can be monitored by the subsystem 414 over time so as to create time-varying funtions that provide other useful information about the characteristics of the processes within the tank 408. For example, by monitoring the conductivity and temperature over time, the amount of energy in each cavitation explosion may be deduced within the analysis subsystem 414, which preferably is microprocessor-controlled.

Figure 35:
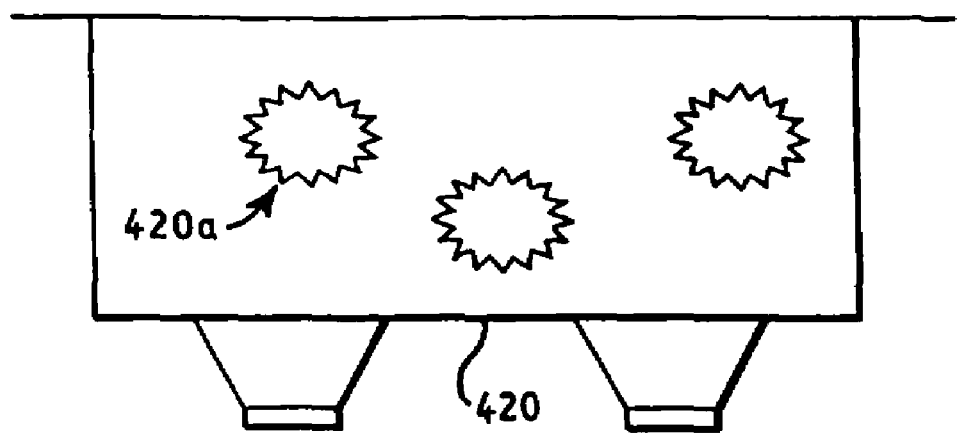
FIGS. 35 and 36 illustrate two process tanks operating with equal input powers but having different cavitation implosion activity.
Figure 36:
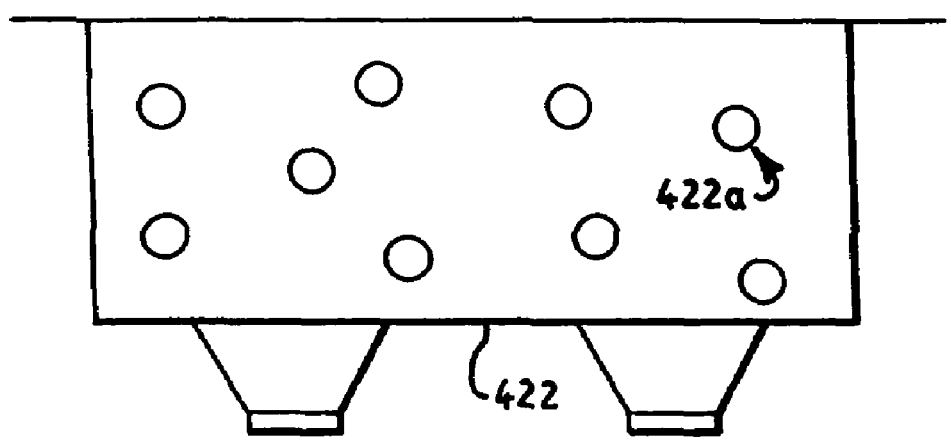

The prior art is familiar with certain meters which measure sound characteristics and cavitations within an ultrasonic tank. Each of the meters gives one number, usually in units of watts per gallon, and sometimes in undefined units such as cavities. However, the activity in a cavitating ultrasonic tank is very complex and no single number adequately describes this activity. For example, as shown in FIGS. 35 and 36, it is possible to have two ultrasonic tanks 420, 422, both having the same input power (i.e. watts per gallon) but each having very different ultrasonic activity characteristics. The first tank 420 might have relatively few high energy cavitation implosions 420a while the second tank 422 has many low energy cavitation implosions 422a (specifically, FIGS. 35 and 36 show cavitation implosions 420a, 422a during a fixed time period in the two tanks 420, 422 having equal input energies). At least two numbers are thus necessary to describe this situation: the energy in each cavitation implosion and the cavitation density. The energy in each cavitation implosion is defined as the total energy released in calories from a single cavitation event; and the cavitation density is defined as the number of cavitation events in one cubic centimeter of volume during a 8.33 millisecond time period. Note, in Europe and other countries with fifty Hz power lines, the cavitation events in one cubic centimeter are counted over a ten millisecond time period and multiplied by 0.833. This technique provides the most accurate measurement for the common ultrasonic systems that have their amplitude modulation pattern synchronized by two times the power line frequency.

In most ultrasonic systems, the cavitation density also varies as a function of time. Accordingly, this is a third characteristic that should be measured when measuring ultrasonic activity in a tank.

Figure 37:
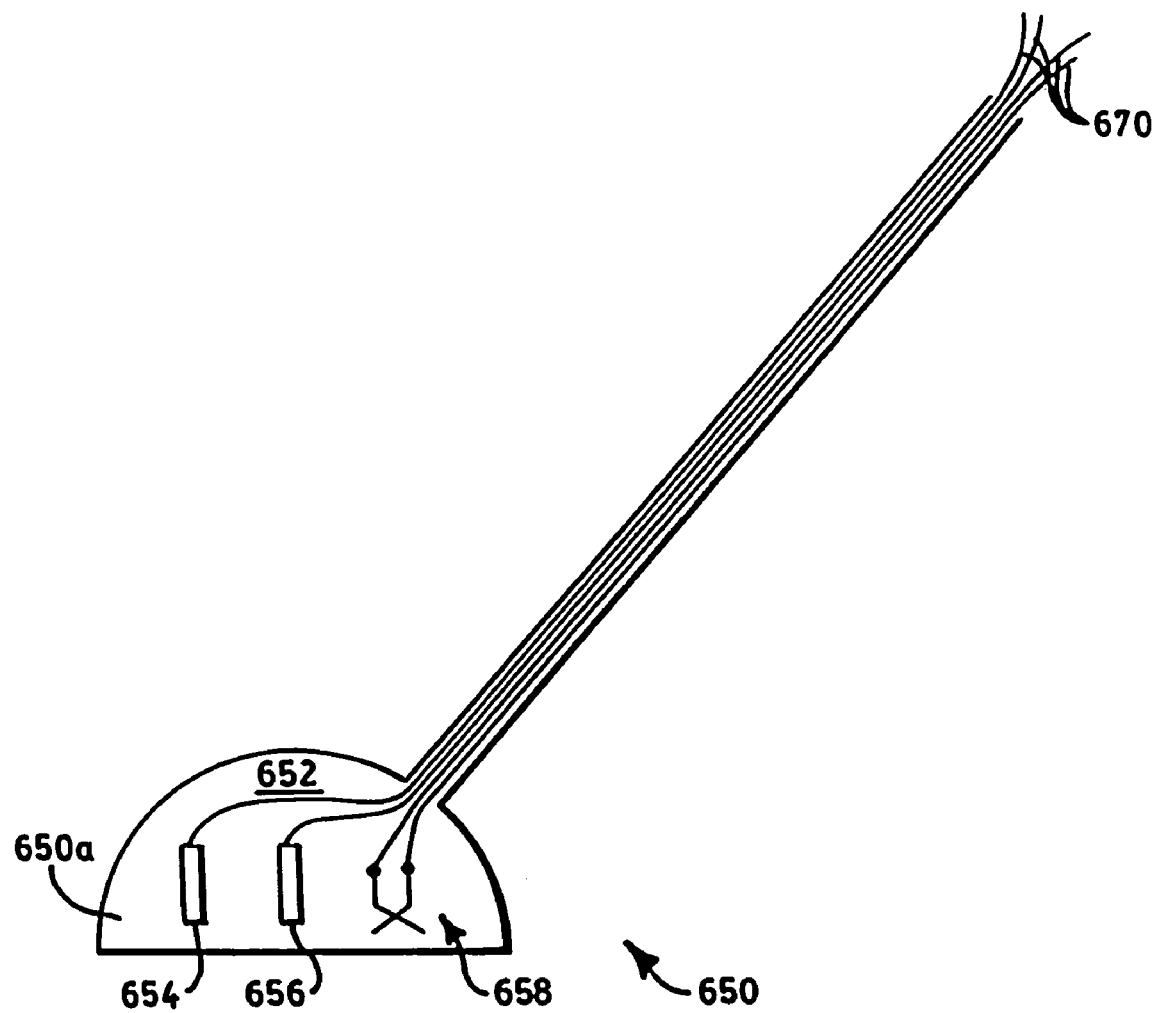
FIG. 37 illustrates a process probe constructed according to the invention and for monitoring process characteristics within a process chemistry such as within an ultrasound tank.

FIG. 37 thus illustrates one probe 650 of the invention which permits the calculation of these important parameters. Specifically, the probe 650 measures average conductivity, conductivity as a function of time, and change in temperature.

A characteristic of ultrasonic cavitation in aqueous solutions is the production of free radicals, ions and super oxides. These by-products of the cavitation increase the conductivity of the aqueous solution. A measure of the conductivity is thus a function of the number of cavitation implosions present in the aqueous sample, and the time variation of this conductivity is a measure of how the cavitation density varies as a function of time.

Another characteristic of cavitation is that it heats the aqueous solution. This is because all the energy released during each cavitation implosion becomes heat energy. By measuring the change in temperature of the aqueous sample, therefore, and by knowing its mass and specific heat, one can calculate the total energy released from the cavitation by the following formula: energy (calories) equals specific heat (no units, i.e., a ratio) times mass (grams) times the change in temperature (° C.). When the amount of energy released is known, as well as the number of cavitation implosions that released this energy, a division of the quantities gives the energy in each cavitation implosion.

The probe 650 is similar in operation to the probe 402 of FIG. 34 and includes a fixed sample volume of a solution 652 (or other chemistry that changes conductivity in an ultrasonic field) contained in the probe tip 650$a$. The probe tip 650$a$ is designed to cause minimal disturbance to the ultrasonic field (e.g., the field 403 of FIG. 34). Accordingly, the probe tip 650$a$ is preferably made of a material that has nearly the same acoustic impedance as the liquid being measured and that has low thermoconductivity. Polypropylene works well since it and water have nearly the same acoustic impedance.

Figure 38:
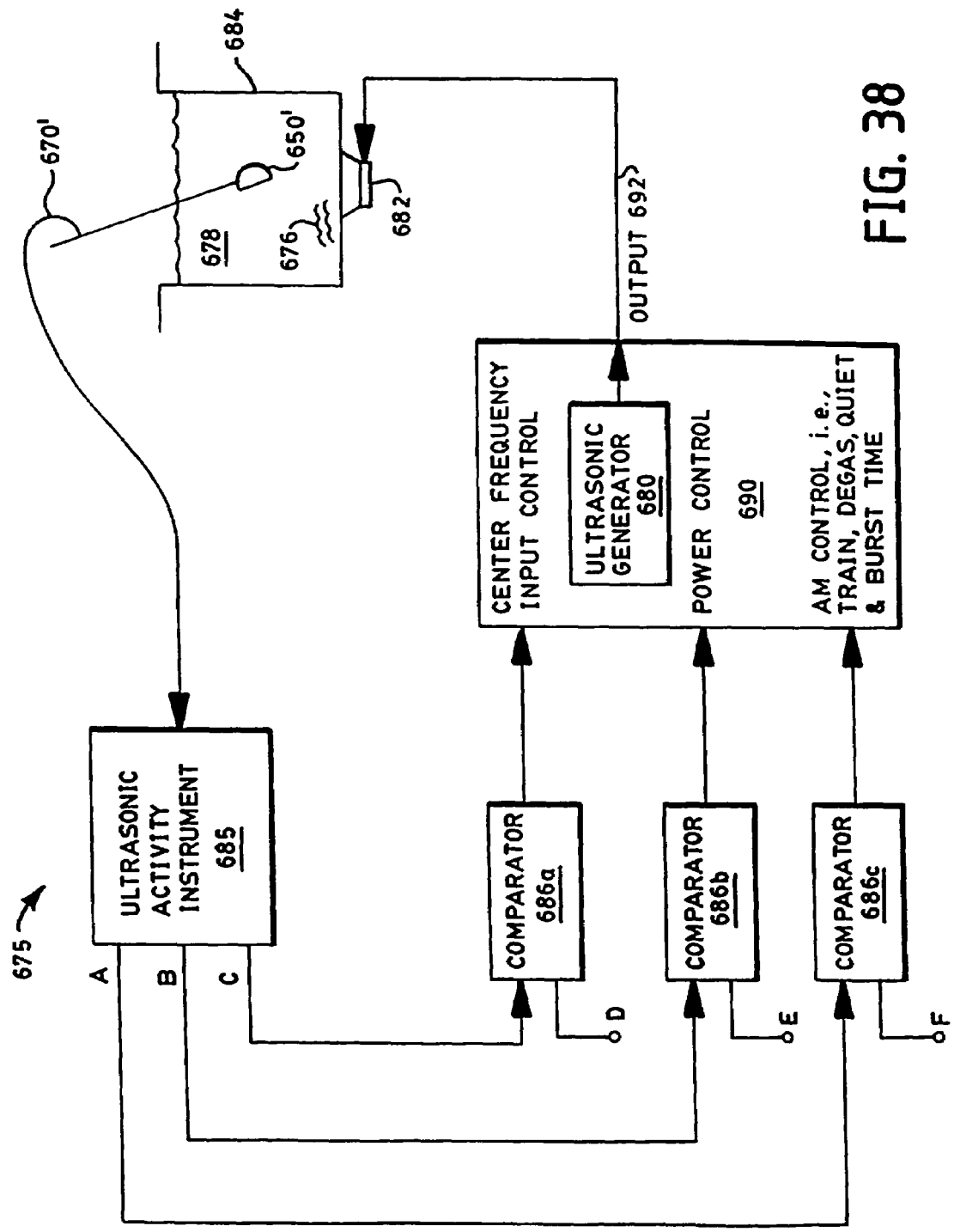
FIG. 38 shows a schematic view of a system incorporating the probe of FIG. 37 and further illustrating active feedback control of energy applied to an ultrasound tank, in accord with the invention.

The probe 650 thus includes, within the probe tip 650$a$, two electrodes 654, 656 to measure conductivity, and a temperature measuring probe (e.g., a thermocouple) 658 to monitor the temperature of the fixed mass of aqueous solution 652. These transducers 654, 656 and 658 are connected to data wires for sampling of the transducer responses. A data collection instrument (e.g., an A/D sensor interface board and a computer) connects to the wires 670 out of the probe 650 to measure temperature rise as a function of time, $\Delta T=g(t)$, and to evaluate this quantity over a specific time period t', in seconds, i.e., $\Delta T=g(t')$. The data collection instrument also measures the initial conductivity, $C_0$, without ultrasonics, and the conductivity as a function of time, $C=h(t)$, within the ultrasonic field. Fixed constants associated with the probe should also be stored, including the specific heat (p) of the liquid 652, the volume (V) of the liquid 652 (in cubic centimeters), the mass (m) of the liquid 652 (in grams), and the functional relationship $n=f(C,C_0)$ between conductivity and the number of cavitation implosions occurring in the probe tip 650$a$ in 8.33 milliseconds determined by counting the sonoluminescence emissions over a 8.33 millisecond period and plotting this versus the conductivity measurement. The instrument then calculates the ultrasonic parameters from this information according to the following formulas:

(a) cavitation density=$D=n/V=f(C,C_0)/V$
(b) energy in each cavitation implosion=$E=(0.00833)(p)(m)(g(t'))/V/f(C,C_0)/t'$
(c) cavitation density as a function of time=$f(h(t))/V$ These three measured parameters are then fed back to the generator to continuously control the output of the generator to optimum conditions. FIG. 38 shows a complete system 675 for monitoring and processing data from such a probe 650' and for modifying applied ultrasound energy 676 applied to the process chemistry 678. Specifically, the system 675 monitors the parameters discussed above and, in real time, controls the generator 680 to adjust its output drive signals to the transducers 682 at the tank 684. The data collection instrument 685 connects to the wiring 670' which couples directly to the transducers within the probe tip 650'. The instrument 685 generates three output signal lines corresponding to measured parameters: the "A" signal line corresponds to the energy in each cavitation implosion, the "B" signal line corresponds to the cavitation density output, and the "C" signal line corresponds to the cavitation density as a function of time. These signal lines A–C are input to separate comparators 686$a$, 686$b$ and 686$c$. The comparators 686$a$–$c$ are coupled to signal lines D–F, respectively, so that the input signal lines A–C are compared to user selected optimum values for each of the parameters. Typically, the user employs empirical experimentation to arrive at the optimum values for a particular tank 684 and chemistry 678. The results from the comparators 686 are input to the control system 690, which controls the generator 680 (those skilled in the art should appreciate that the controller 690 and generator 680 can be, and preferably are, coupled as a single unit).

The energy in each cavitation implosion decreases as the frequency of the ultrasonics 676 increases and as the temperature of the solution 678 increases. The energy in each cavitation implosion is measured and compared to the optimum value (set by signal lines D–F) for the process, and if the measured value has a higher energy value than the optimum value, as determined by the comparators 686, the center frequency of the generator 680 is increased (by the controller 690 receiving data at the "center frequency input control") until the values are equal. If there is not enough range in the center frequency adjustment to reach the optimum value, then the temperature of the solution 678 is increased by the control system 690 until the optimum value is reached. An alternative is to utilize a switchable frequency generator, as described above, so as to change the drive frequency to one where the energy in each cavitation implosion is not greater than the optimum value, and without changing the solution temperature.

The cavitation density increases as the ultrasonic power into the tank 684 increases. Therefore, the cavitation density measurement fed back to the generator 680 is compared against the optimum value of cavitation density for the process; and if the measured value is lower than the optimum value, the generator output power is increased (by the controller 690 receiving data at the "power control") until the two values are equal. If the measured value is greater than the optimum value, the generator output power is decreased until the values are equal.

Cavitation density as a function of time is controlled by the amplitude modulation (AM) pattern of the generator output 692. Therefore the measured cavitation density as a function of time is measured and the generator's AM pattern is adjusted (via the controller 690 receiving data at the "AM Control") until the measured function equals the optimum function.

Figure 39:
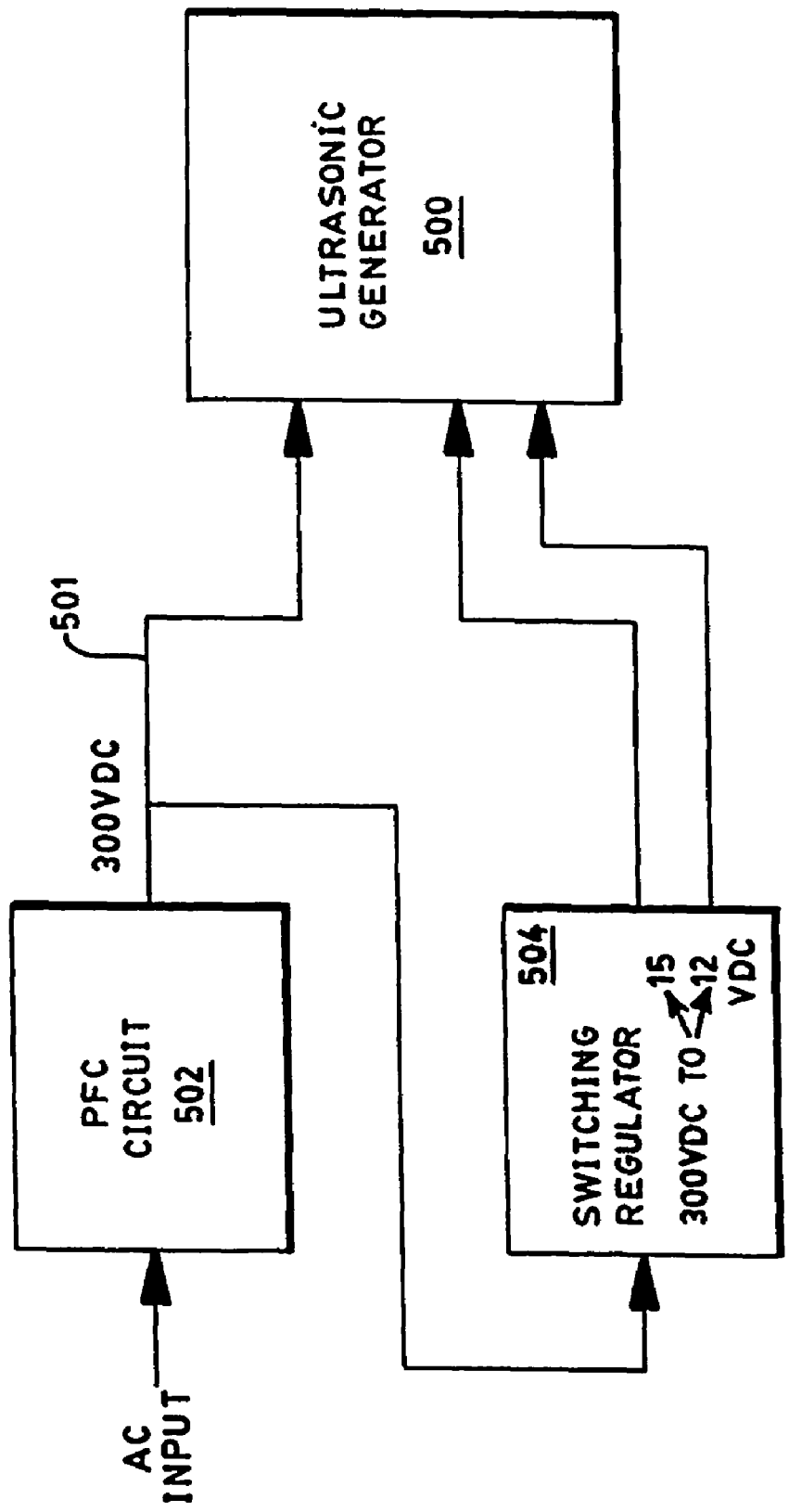
FIGS. 39–41 illustrate alternative embodiments of ultrasonic generators with universal voltage input, in accord with the invention.
Figure 40:
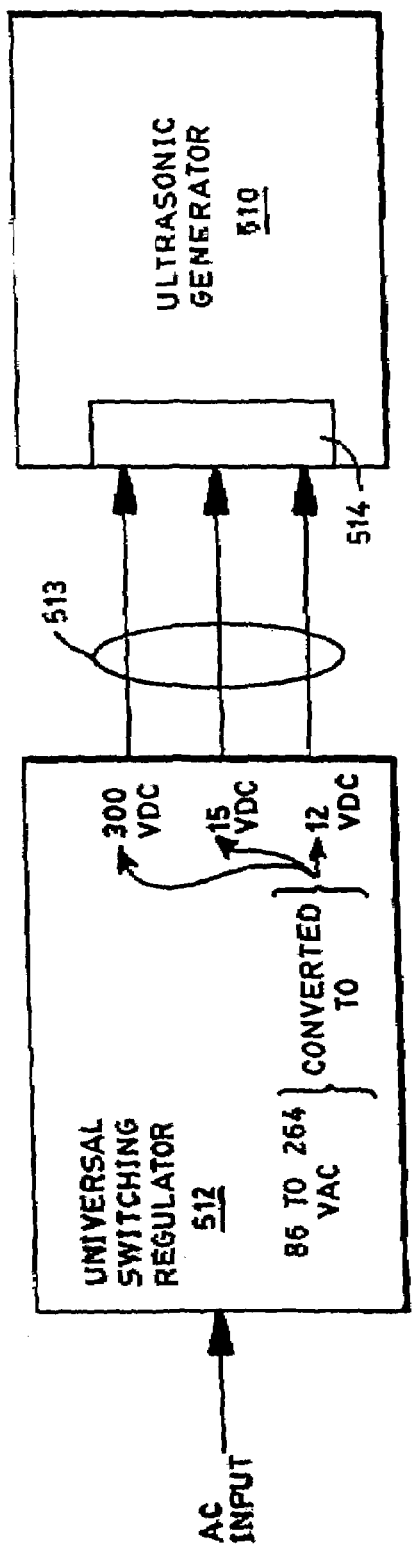
Figure 41:
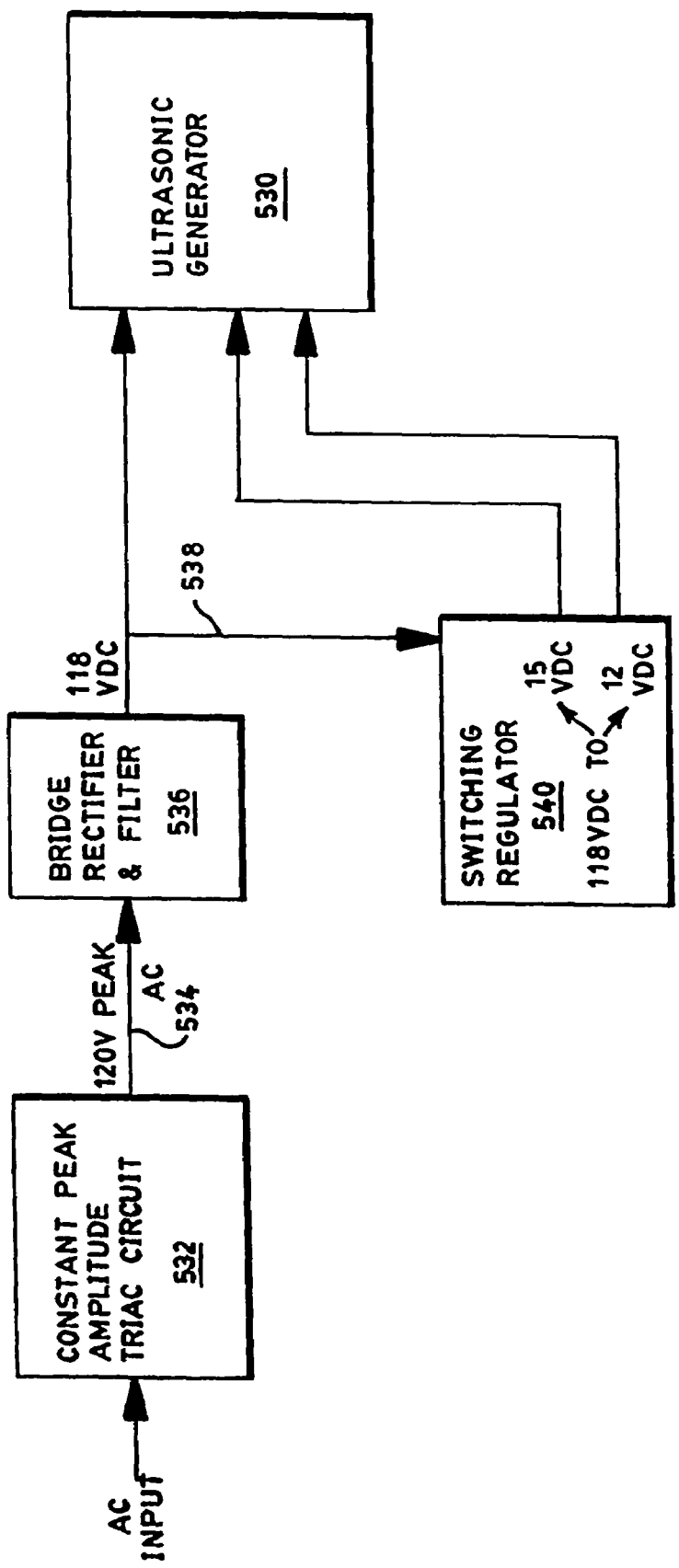

FIGS. 39–41 illustrate separate embodiments of universal voltage input ultrasonic generators, in accord with the invention. These embodiments are made to solve the present day problems associated with separate designs made for countries with differing power requirements (in volts A–C, or "VAC"), such as:

| | |
|---|---|
| 100 VAC | Japan, and intermittently during brown-outs in the U.S. |
| 120 VAC | U.S. |
| 200 VAC | Japan |
| 208 VAC | U.S. |
| 220 VAC | Most of Europe except Scandinavia and U.K. |
| 240 VAC | U.S., U.K., Norway, Sweden and Denmark |
| "Z" VAC | Corresponding to unusual voltages found in France and other world locations |

These voltages are obviously problematic for industry suppliers of ultrasonic generators, who must supply the world markets. The invention of FIGS. 39–41 eliminates the chance that a particular world consumer receives an incorrect generator by providing universal voltage generators that operate, for example, between 86 VAC and 264 VAC.

In FIG. 39, an ultrasonic generator 500 is shown connected to a 300 VDC source 501. A power factor correction (PFC) circuit 502 connects to the front end of the generator 500 to produce a regulated 300 VDC. A switching regulator 504 regulates the 300 VDC to +12V and +15V. The generator 500 can be represented, for example, as the circuit of FIG. 31, except that the "high voltage supply" is replaced by the PFC circuit 502 and the +12V and +15V are replaced with control voltages from the regulator 504.

FIG. 40 illustrates a generator 510 connected to a universal input switching regulator 512. The regulator 512 generates a set 513 of DC voltages for the generator 510. The generator 510 includes circuitry 514 that operates with the set 513. The generator 510 can be represented, for example, as the circuit of FIG. 31, except that the "high voltage supply" and the +12V and +15V are replaced with output voltages from the regulator 512.

Those skilled in the art should appreciate that methods and systems exist for utilizing the power line to acquire amplitude control for ultrasonic generators. By way of example, the inventor of this application describes such systems and methods in connection with FIGS. 3, 4, 5A, 5B and 7 of International Application No. PCT/US97/12853. Specifically, an amplitude control subsystem is achieved by rectifying the AC power line and selecting a portion of the rectified line voltage that ends at the desired amplitude (such as between zero and 90° or between 180° and 270° of the signal). In this manner, amplitude modulation is selectable in a controlled manner as applied to the signal driving the transducers from the generator. For example, by selecting the maximum amplitude of 90° in the first quarter sinusoid, and 270° in the third quarter sinusoid, a maximum amplitude signal is provided. Similarly, a one-half amplitude signal is generated by choosing the 30° and 210° locations of the same sinusoids. By way of a further example, a one-third amplitude signal is generated by choosing 19.5° and 199.5°, respectively, of the same sinusoids.

FIG. 41 illustrates a generator 530 which operates at a DC voltage less than or equal to $(86)(\sqrt{2})$ volts. As in amplitude control, a triac 532 is used to select that portion of the power line voltage with an amplitude equal to the generator DC voltage requirements. The signal 534 is rectified and filtered by the bridge rectifier and filter 536 to obtain the constant DC voltage 538 in the range less than or equal to $(86)(\sqrt{2})$ volts. The generator 530 can be represented, for example, as the circuit of FIG. 31, except that the "high voltage supply" is replaced by the voltage from the bridge rectifier and filter 536 and the +12V and +15V are replaced with output voltages from the regulator 540, as above.

In another embodiment, the selected AC voltage angle can be reduced to lower the DC voltage to reduce the amplitude of the ultrasonic drive signal.

The "power up sweep" features of the invention also apply to amplitude modulation, where an AM pattern of the AM frequency varies according to the power up-sweep techniques discussed above, and preferably at the same time with the techniques of "sweep the sweep rate", as discussed herein. With power up-sweep AM, the AM pattern modulation creates an additional upward force on contamination while eliminating low frequency resonances.

Figure 42:
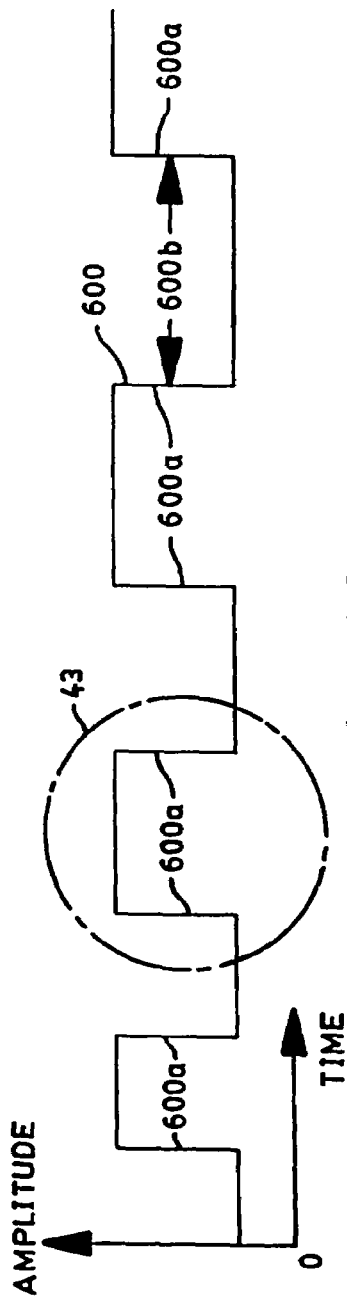
FIG. 42 graphically illustrates an AM burst pattern in accord with the invention.
Figure 43:
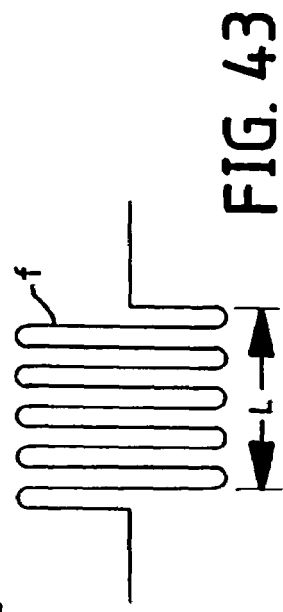
FIG. 43 illustrates one burst of primary frequency ultrasound within one of the non-zero AM periods.

FIG. 42 illustrates an AM (amplitude modulation) pattern 600 of the invention, where the frequency of the AM is constantly decreasing with increasing time t. More particularly, ultrasonic bursts of energy (as shown in FIG. 43, with a frequency f) are contained within each of the non-zero portions 600a of the pattern 600. As time increases, longer and longer bursts of energy are applied to the associated transducers. In the optimum case, the ultrasound frequency within each burst of FIG. 43 varies with a power up sweep, from $f_{upper}$ to $f_{lower}$, as discussed above.

Figure 44:
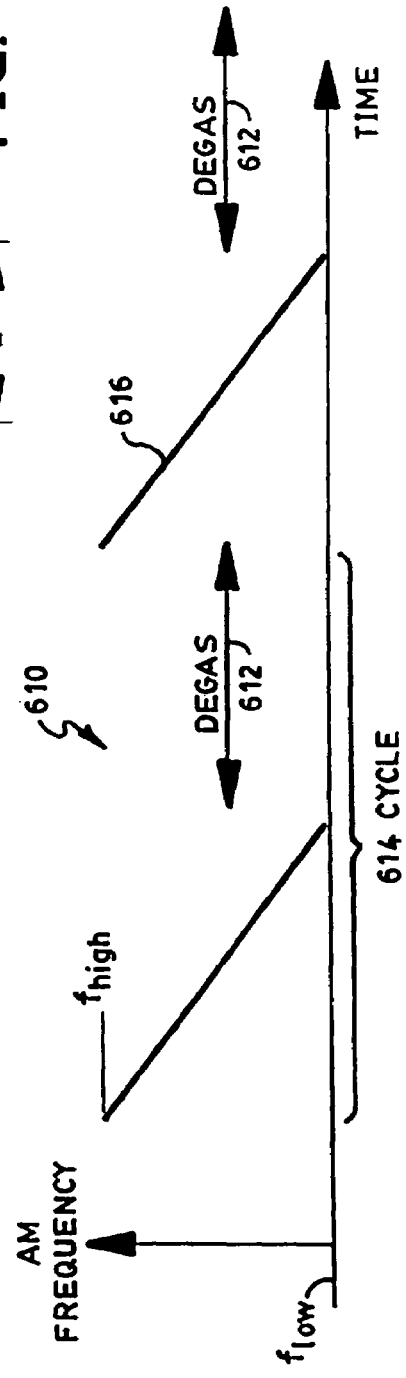
FIG. 44 illustrates an AM sweep pattern, in accord with the invention.

FIG. 44 shows a plot 610 of AM frequency verses time t. As shown, the AM frequency monotonicly changes from a high frequency, $f_{high}$, to a low frequency, $f_{low}$. When $f_{low}$ is reached, a degas or quiet period 612 is typically introduced before the cycle 614 repeats.

Note that the sweep rate of the change of the AM frequency along the slope 616 can and preferably does change at a non constant sweep rate. The rate of AM frequency change can thus be non-constant. The degas period 612 can also be non constant. The degas period 612 can also be substantially "0", so that no time is permitted for degas.

Generally, there are three ways to change the AM frequency. The burst length "L" (FIG. 43) can be changed, the time between bursts can be changed (e.g., the periods 600b, FIG. 42, where the amplitude is zero); or both parameters can be changed simultaneously.

Figure 45A:
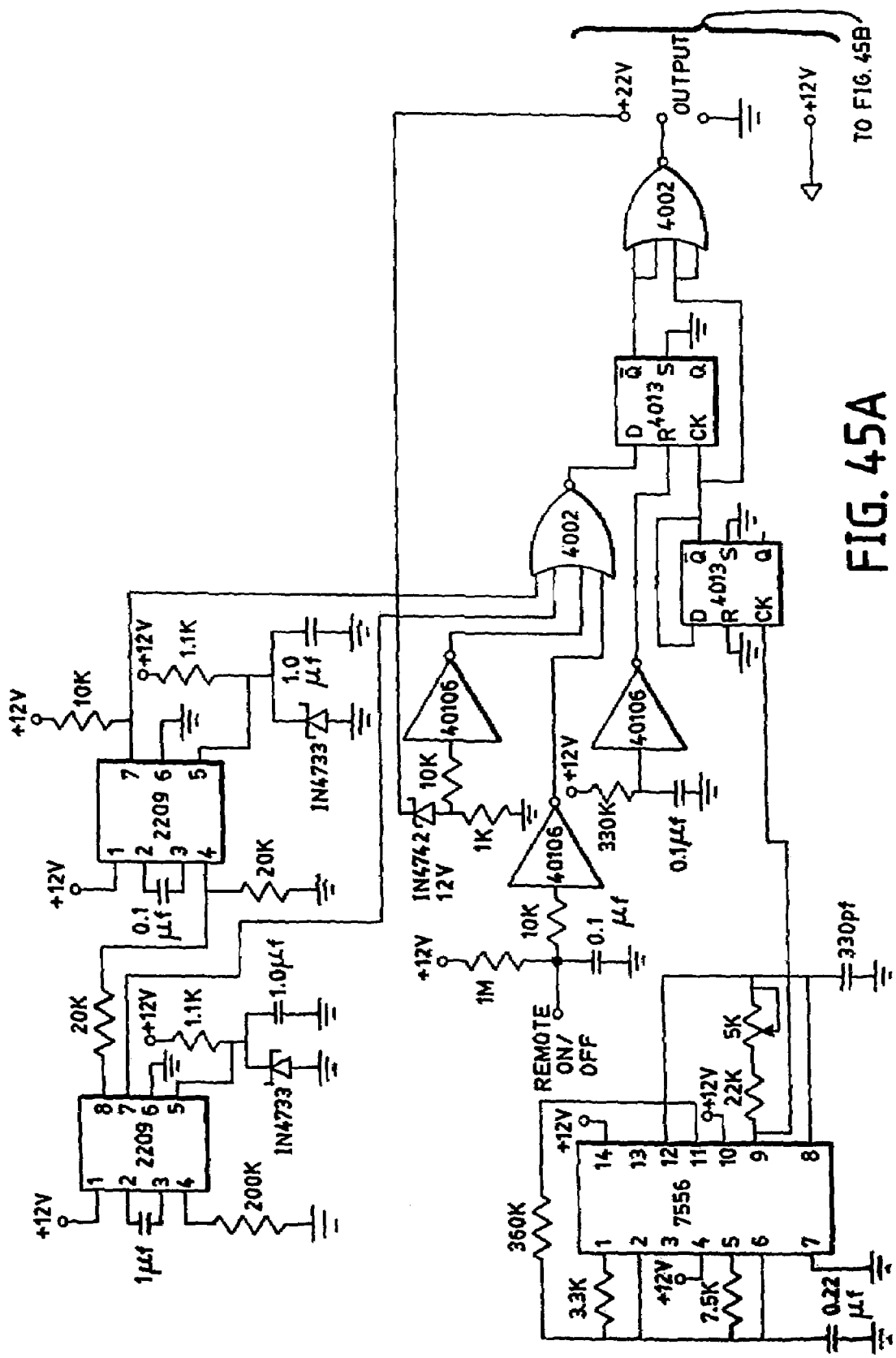
FIGS. 45A–45C schematically show one AM power up-sweep generator circuit constructed according to the invention.
Figure 45B:
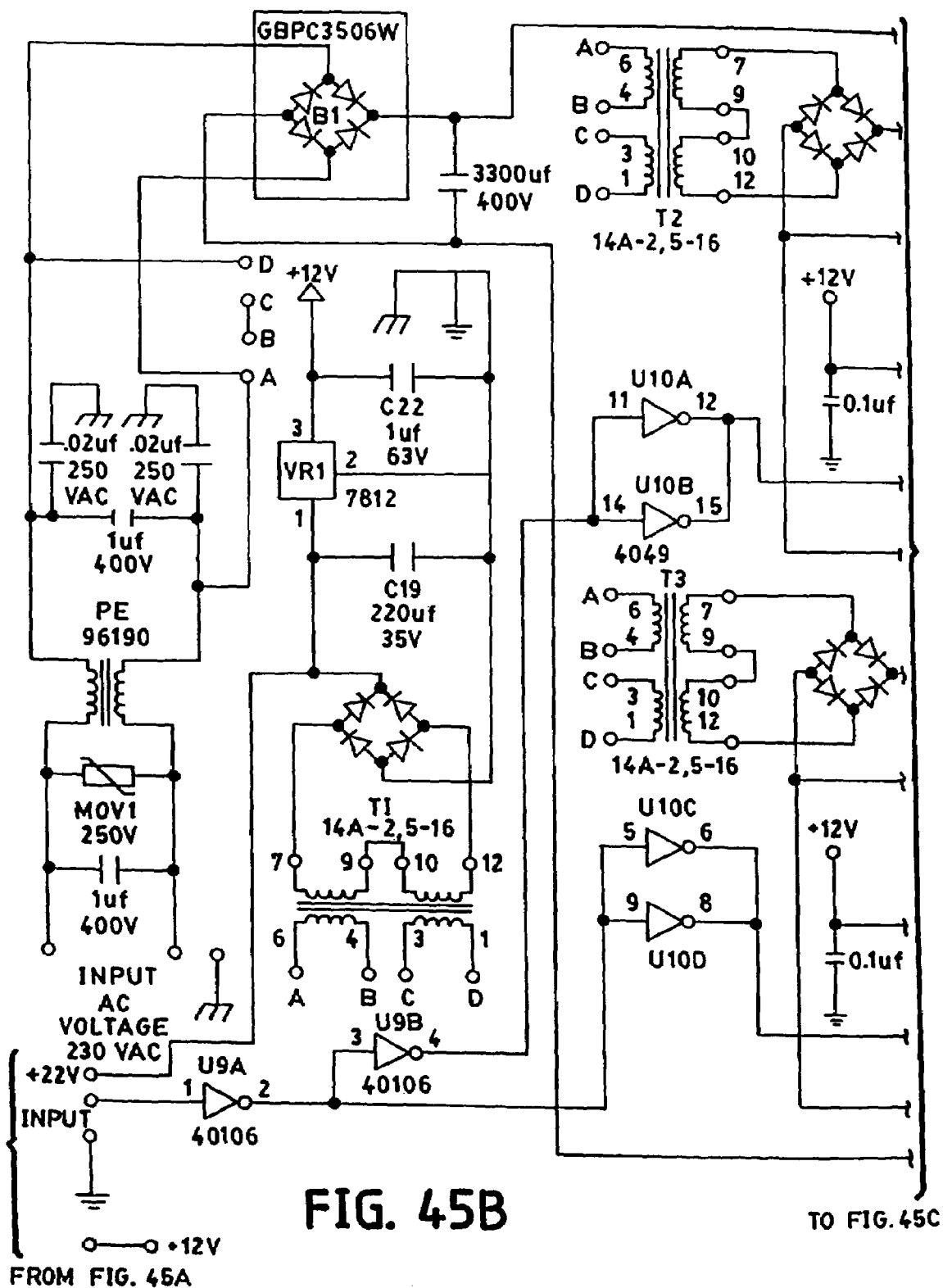
Figure 45C:
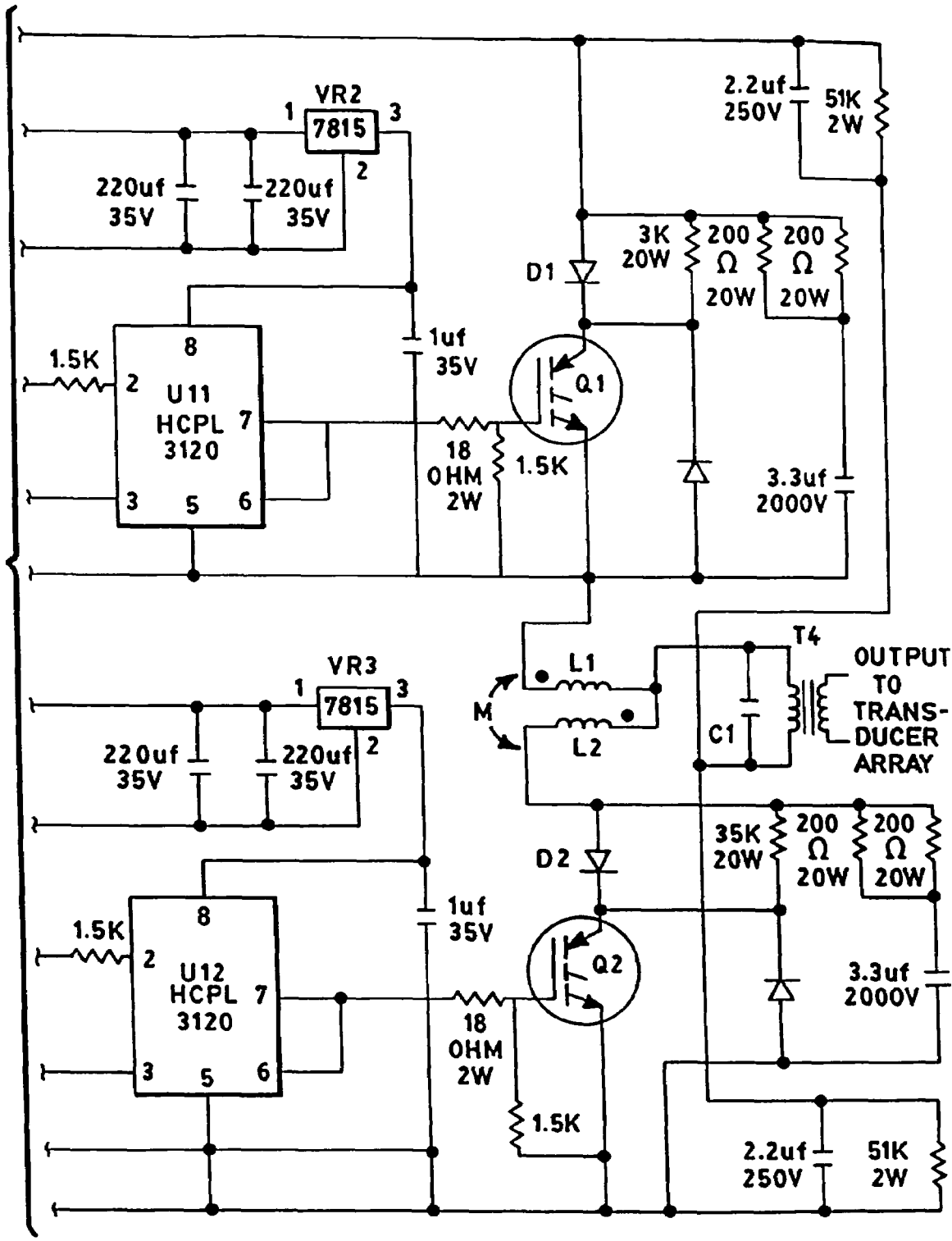

FIGS. 45A–45C schematically illustrate electronics for one ultrasonic generator with AM power up-sweep capability, in accord with the invention.

Figure 46:
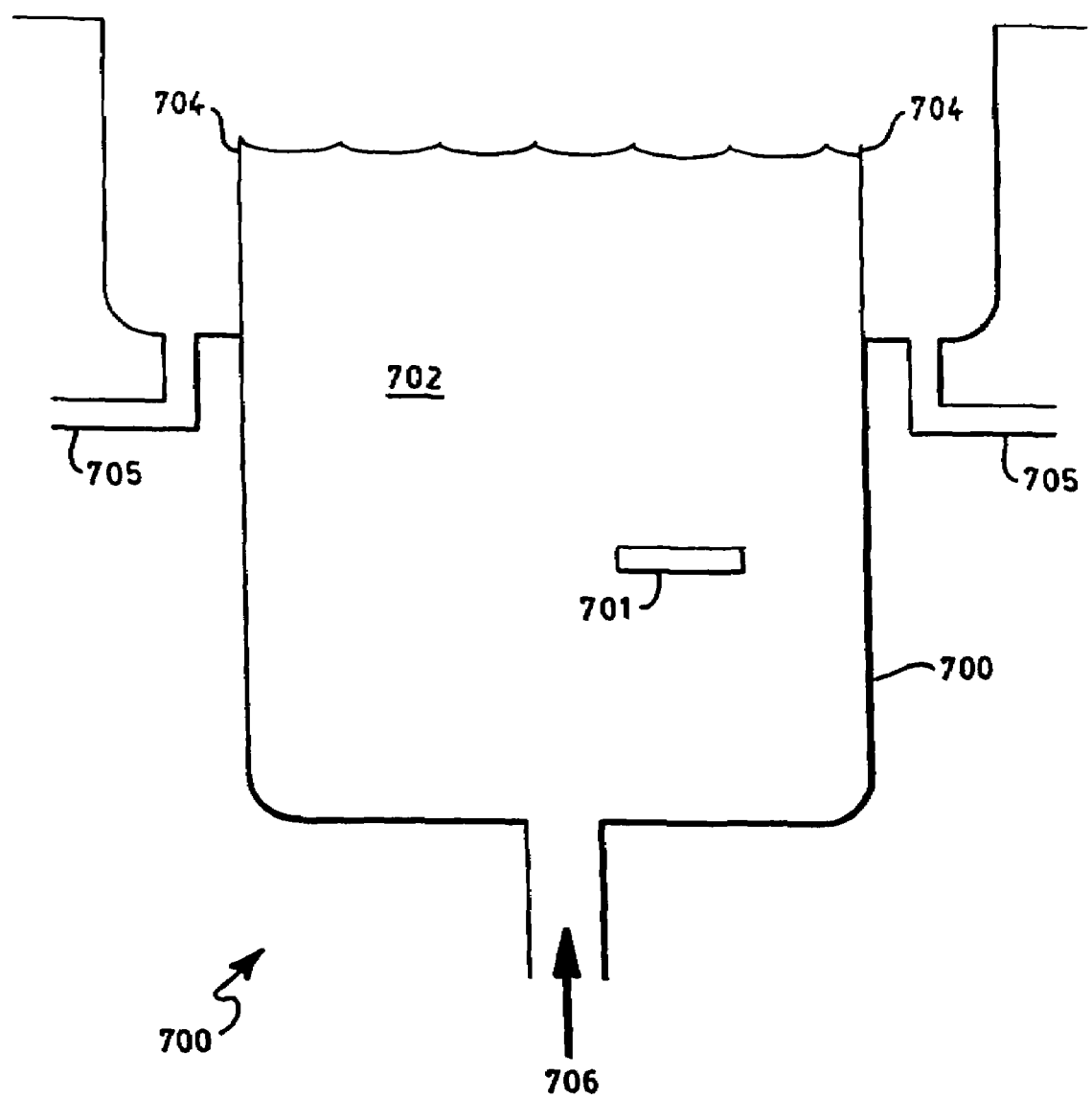
FIG. 46 shows a prior art laminar tank.

FIG. 46 illustrates a prior art laminar tank 700. Contamination within the tank 700 is a problem in critical cleaning operations because the contamination can re-deposit on the part 701 under process. A common way to remove contamination from the cleaning solution 702 of the tank 700 is to build the tank 700 with overflow weirs 704 and to constantly add pure solution, or re-circulate filtered solution, into the bottom of the tank at a solution inlet 706. The solution injected through the inlet 706 travels through the tank volume and out over the overflow weirs 704. Solution which overflows the weirs 704 exits through outlets 705 for disposal or filtering.

The problem with cleaning the solution 702 in this manner is that the cleaning time is excessive because there is mixing of pure or filtered solution with contaminated solution while solution passes through the volume of the tank 700. The mixing causes a dilution of the contaminated solution by the pure or filtered solution. The result is that diluted solution overflows the weirs 704; and the contamination within the tank 700 is eliminated logarithmically rather than linearly. Logarithmic elimination theoretically takes an infinite amount of time to reach zero, whereas linear elimination has a theoretical finite time when the tank becomes contamination free.

Figure 47:
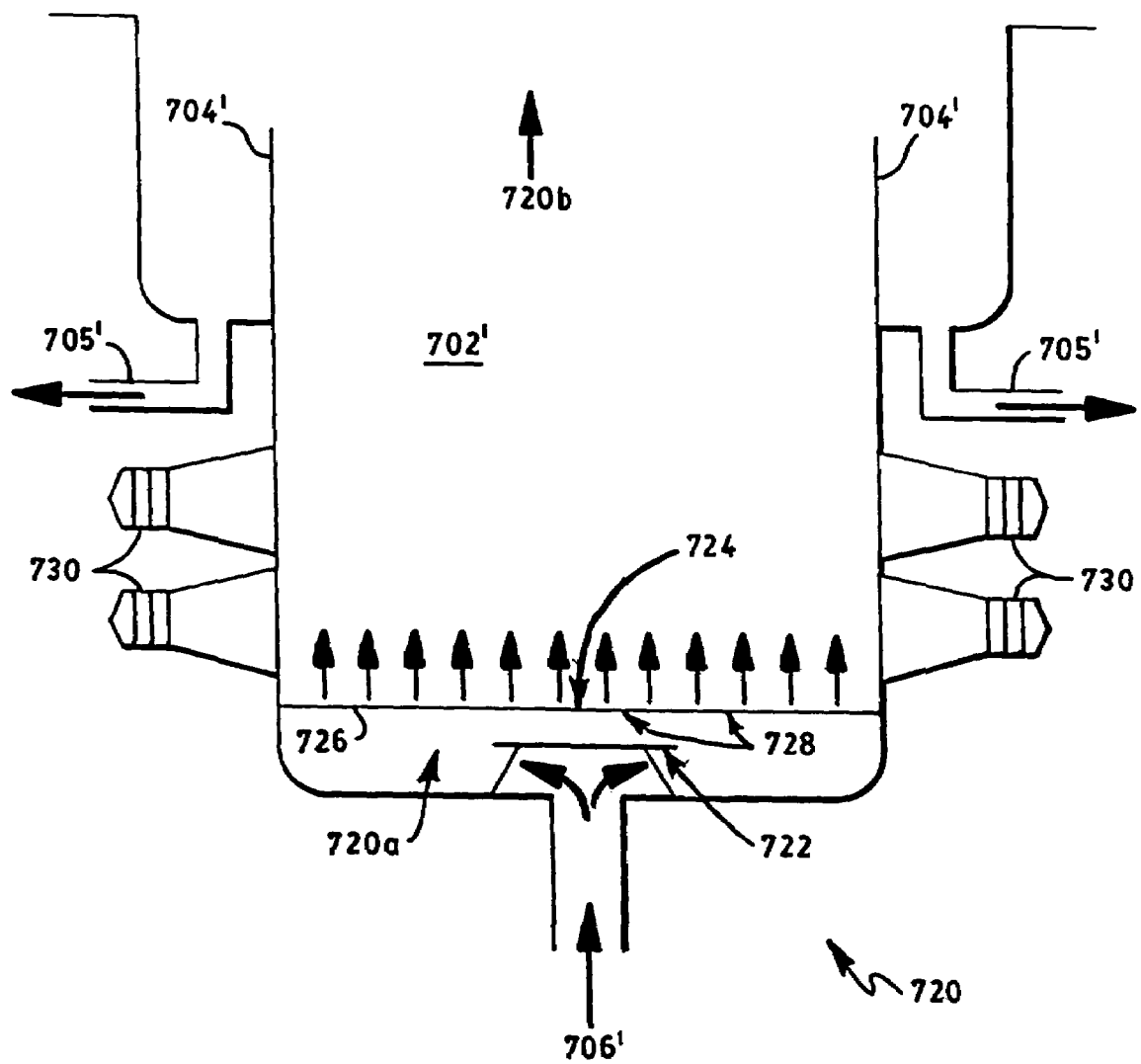
FIG. 47 shows an improved laminar tank, constructed according to the invention.

The tank 720 of FIG. 47, constructed according to the invention, thus includes features which significantly reduce the afore-mentioned problems. Specifically, the tank 720 operates such that the solution 702' in the tank 720 moves in a piston like fashion from the bottom 720a to the top 700b of the tank 700, resulting in little or no mixing of contaminated solution with the new or filtered solution. Near linear removal of the contamination within the tank 700 results, providing for rapid clean up.

The tank 720 has a number of baffles that: reduce the velocity of the clean solution; equalize the pressure of the clean solution; and introduce the solution into the tank 720 with even distribution at the bottom 720a of the tank 720. The first baffle 722 reduces the velocity of the solution injected through the inlet 706'. The second baffle 724 evenly distributes the solution at the bottom of the tank 720a. Baffle 724 has a plate 726 with a large number of small holes 728 cut therethrough to give a minimum of 45% open area so that the pressure across any hole is minimized.

The combination of the baffles 722 and 724 operate to provide smooth movement of contaminated solution upwards and over the wiers 704'. The tank 720 thus augments, or provides an alternative to, the power up-sweep features discussed above.

The design of the tank 720 also benefits from alternative placement of the ultrasonic transducers 730 mounted with the tank. As illustrated, the transducers 730 are mounted to the sides 720s of the tank, decreasing the disruption which might otherwise occur from bottom-mounted transducers interfering with the solution flow through the baffles 722, 724.

A common feature in prior art tanks (ultrasonic and non-ultrasonic) is a quick dump rinse feature (QDR) where a large valve in the bottom of the tank opens to allow the solution in the tank to quickly drain out of the tank. This QDR feature reduces the contamination residing on the parts under process as compared to the contamination that would reside if the liquid were removed more slowly from the tank, or if the parts were pulled out of the tank.

Figure 48:
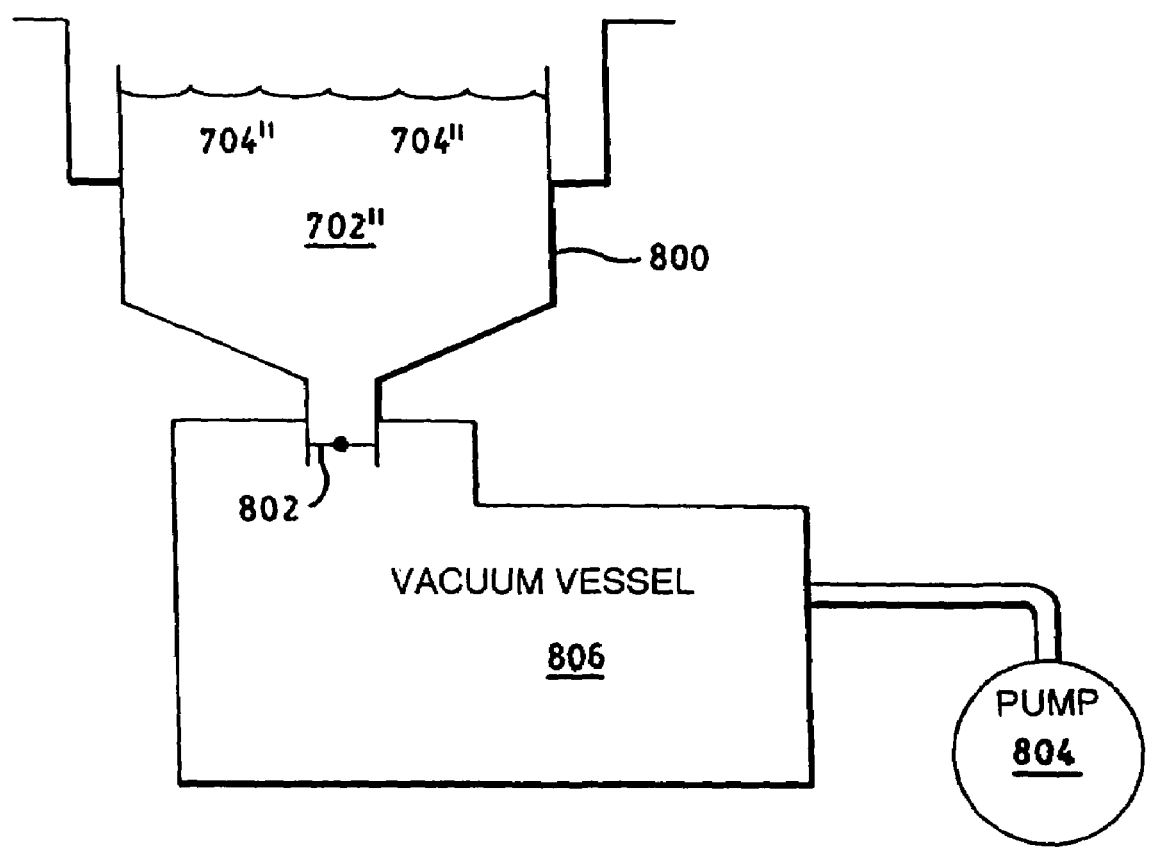
FIG. 48 shows a quick dump rinse (QDR) tank constructed according to the invention.

FIG. 48 illustrates a QDR tank 800 modified in accord with the invention to speed up the rate of liquid removal from the tank. The large valve output 802 is connected to a vacuum reservoir 806 that is evacuated to a pressure below atmospheric pressure during the cleaning cycle. When the valve 802 is opened to dump the liquid 702", the difference between atmospheric pressure and the pressure in the vacuum vessel 806 forces the liquid 702" out of the tank 800, thus shortening the drain time and further reducing the residual contamination.

Figure 49:
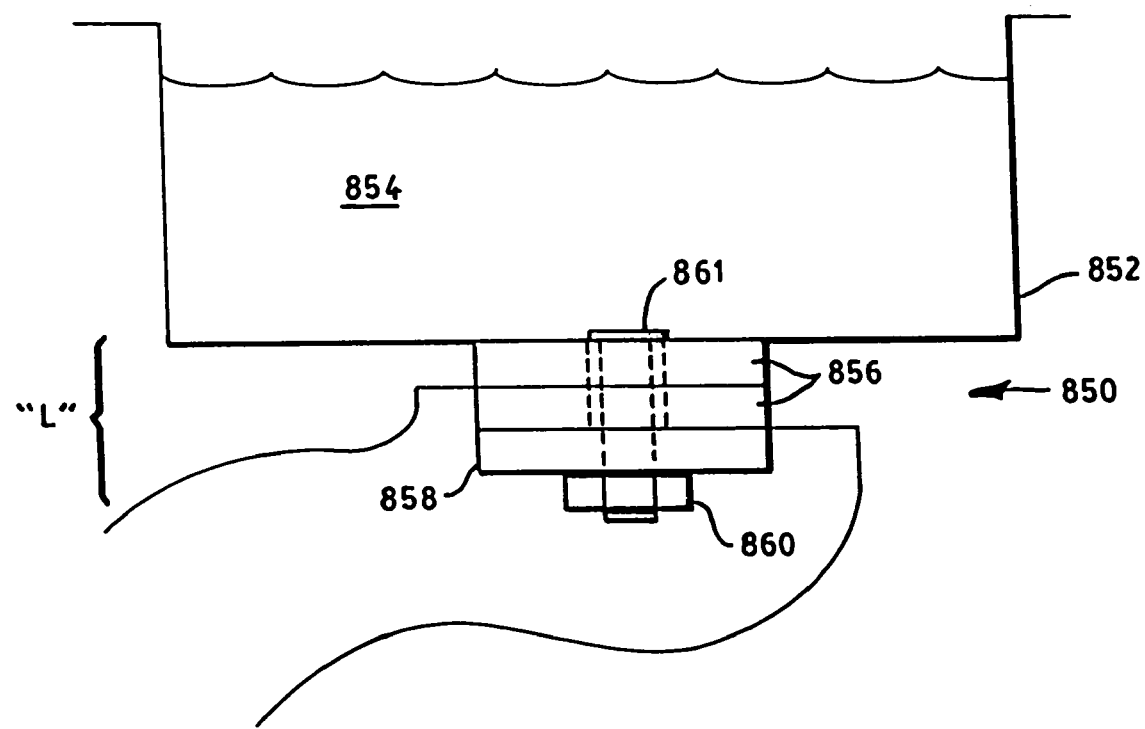
FIG. 49 shows an improved high frequency transducer constructed according to the invention.

The conventional stacked transducer consists of a front driver, active piezoelectric elements and a back mass. The length "L" of the transducer (from front plate to backplate) basically determines the transducer's primary and harmonic frequencies. As the fundamental frequency of the transducer becomes higher, the thickness of each of the transducer elements is reduced until they become impractical. FIG. 49 shows a transducer 850 constructed according to the invention which reduces this impracticality.

In FIG. 49, the transducer 850 is shown connected to an ultrasound processing tank 852, which holds process chemistry 854. The transducer includes two piezoelectric elements 856 that are compressed between the backplate 858 and the tank 852. Specifically, a bias bolt 860 connects through the transducer 850 and connects directly into a weld 861 at the tank 852. Accordingly, there is no front plate; and thus the transducer length "L" can be divided between the piezoelectric elements 856 and the back mass 858. This division makes it possible to make a stacked transducer 850 with a higher fundamental frequency (and higher harmonics too).

Most transducers discussed herein are longitudinal vibrators with elements sandwiched by a center bolt that holds the transducer assembly together and that provides a compressive bias to the active piezoelectric components (i.e., sandwiched between the a front plate and back mass or backplate). Since piezoelectric ceramic is strong under compression, but weak in tension, the constant compressive force provided by the spring constant of the bolt greatly improves the reliability of this transducer over other configurations.

The longitudinal vibrating transducer is normally connected to the tank or other surface that is to receive the sound energy by epoxy or brazing, or by a mechanical stud, or by a combination of these schemes.

Figure 50:
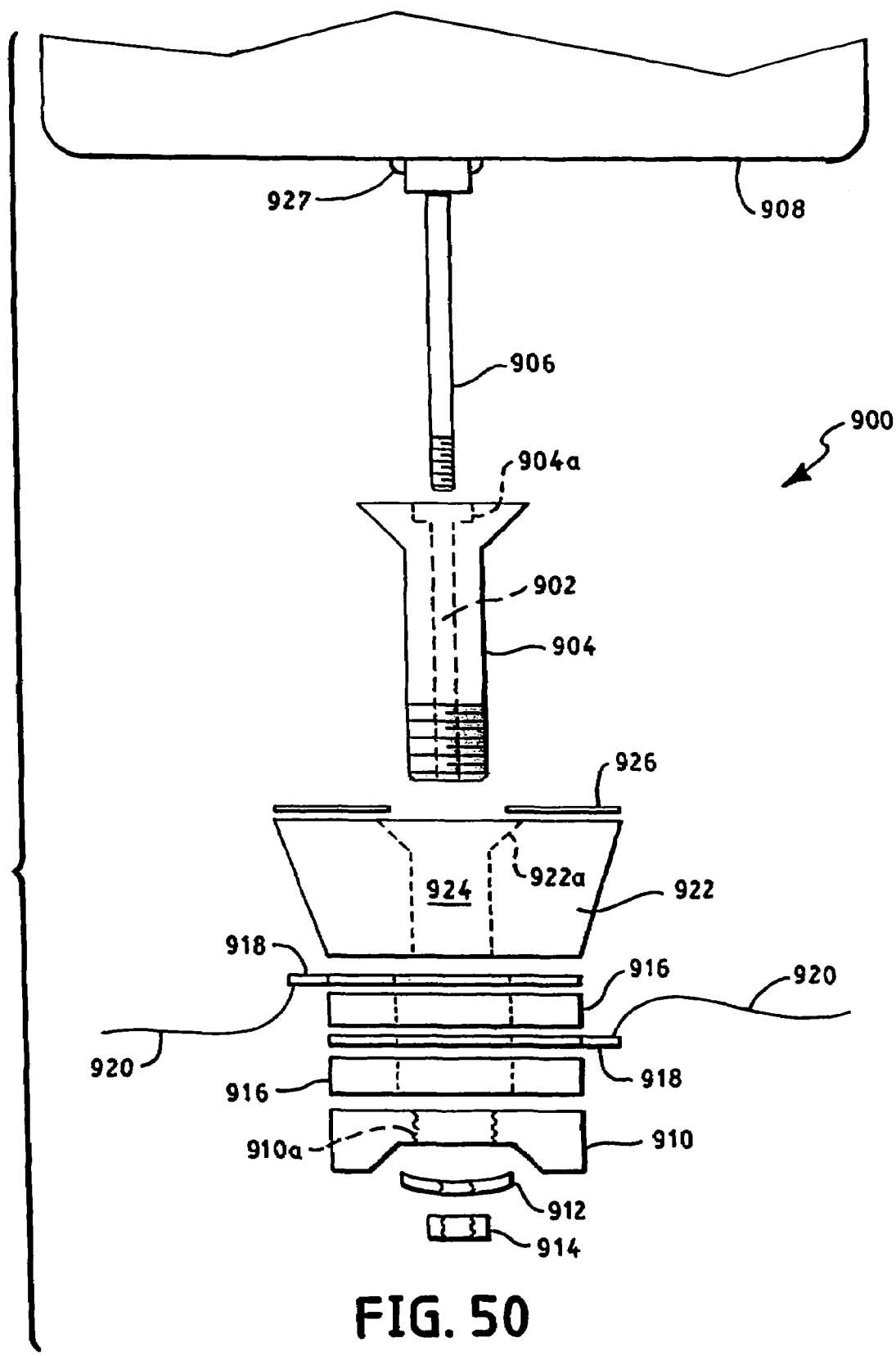
FIG. 50 illustrates, in a side exploded view, a double compression transducer constructed according to the invention.

The invention of FIG. 50 illustrates a transducer 900 constructed according to the invention and shown in an exploded view. The transducer 900 has "double compression", as discussed below, to increase its reliability over the prior art. Specifically, the bias bolt 904 has a through-hole 902 in its center. The center hole 902 receives a second bolt 906 that is welded to the surface of the tank 908 (illustrated by weld joint 927. When integrated, the second bolt 906 protrudes out past the tail mass 910 (i.e., the backplate) of the transducer 900 by way of a Belleville disc spring washer 912 and nut 914, which screws onto bolt 906.

As in other transducers herein, the transducer 900 includes piezoelectric ceramics 916, associated electrodes 918, and lead-outs 920 for the electrodes 918.

The bias bolt 904 thus provides the first compressive force similar to other transducers herein. That is, the bolt 904 slides through the front driver 922 via the through-hole 924, and continues on through the ceramics 916. The back mass 910 has threads 910a which mate with the bolt 904; and thus the bolt 904 screws into the back mass 910. By tightening the bolt 904 into the back mass 910, the bolt 904 firmly seats into the counter-sink 922a of the front plate 922 and compression is applied to the ceramics 916.

As an alternative, the threads in the back mass 910 can be thru-holed; and a nut against the back mass can replace the threads to support compression bias on the piezoceramic 916.

The second compressive force derives from the operation of the second bolt 906, which compresses the epoxy 926 after seating within the counter-sink 904a of the first bolt 904 and after tightening the nut 914 onto the bolt 906. The front driver 922 is then bonded to the tank 908 via an epoxy layer 926. The second compressive force keeps a compressive bias on the epoxy 926 bond between the front driver 922 and the tank surface 908.

As an alternative, it is possible to eliminate the Belleville disc spring washer 912 and rely entirely on the spring tension in the second bolt 906; but the added feature of the Belleville disc spring washer 912 provides a larger displacement before tension goes to zero.

The second compressive bias of transducer 900 provides at least three improvements over the prior art. First, during the epoxy curing process, the bias keeps force on the epoxy bond 926 (even if the epoxy layer thickness changes during a liquid state) resulting in a superior bond. Second, during operation of the transducer 900, the reliability of the bond 926 is enhanced because of the constant mechanical compressive force. That is, epoxy bonds are weakest in shear forces, and reasonably strong in tension but superior in compression. Third, during abnormal conditions (e.g., a mechanical jar to the bonding surface) that might dislodge a conventionally bonded transducer, the second compression force with its spring characteristics absorbs the mechanical shock and protects the epoxy bond.

Those skilled in the art should appreciate that the double compression transducer 900 provides increased reliability when mounted with most any surface, and not simply an ultrasonic tank 908.

Figure 51:
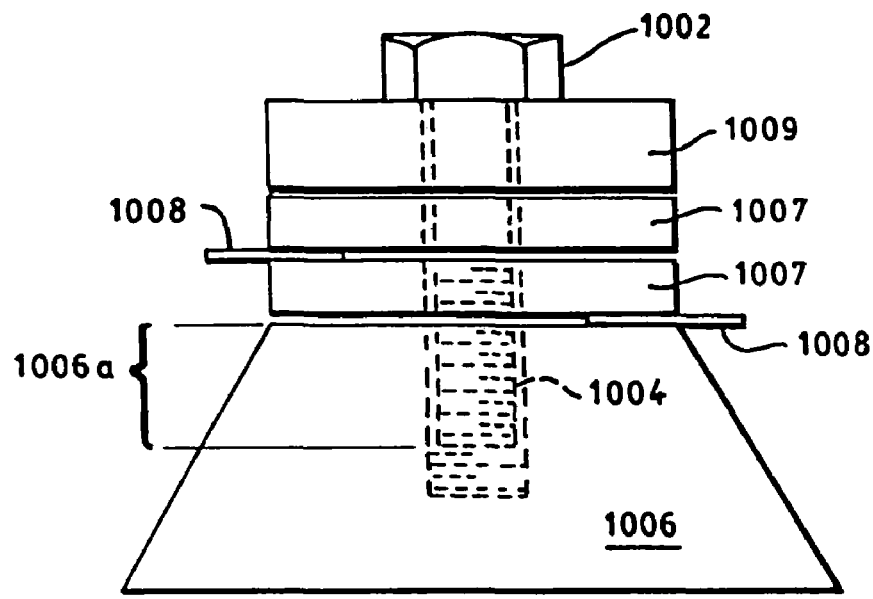
FIG. 51 shows a prior art transducer with a bias bolt threaded into the upper part of the front driver.

FIG. 51 shows a cross-sectional view of a conventional stacked transducer 1000 with a bias bolt 1002 that screws into threads 1004 in the aluminum front driver 1006. The threads 1004 are only within the top portion 1006a of the front driver 1006. The transducer includes the normal piezo-ceramics 1007, electrodes 1008, and rear mass 1009.

Figure 52:
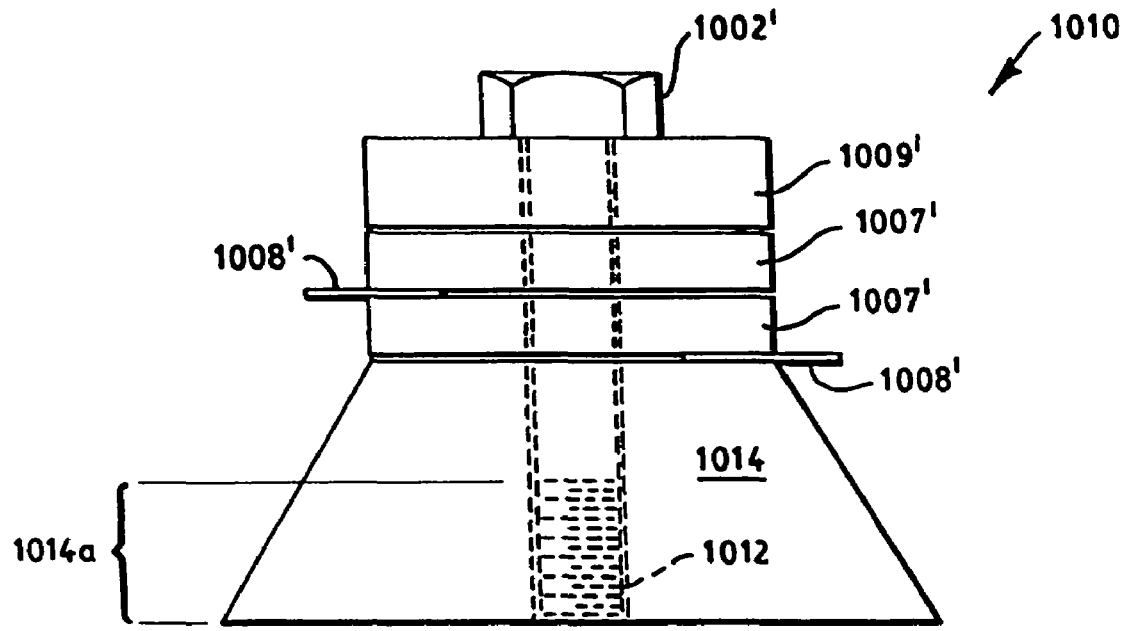
FIG. 52 shows an improved transducer, constructed according to the invention; with a bias bolt threaded into a lower part of the front plate.

FIG. 52 shows an alternative transducer 1010 constructed according to the invention. In transducer 1010, the threads 1012 within the front driver 1014 are at bottom portion 1014a so that bias pressure is not concentrated on the top threads (as in FIG. 51) where the surface of the aluminum can be deformed in operation, decreasing bias pressure. The elements 1002', 1007', 1008' and 1009' have similar function as in FIG. 51; except that they are sized and shaped appropriately to accommodate the thread repositioning at the bottom 1014a of the driver 1014.

Figure 53:
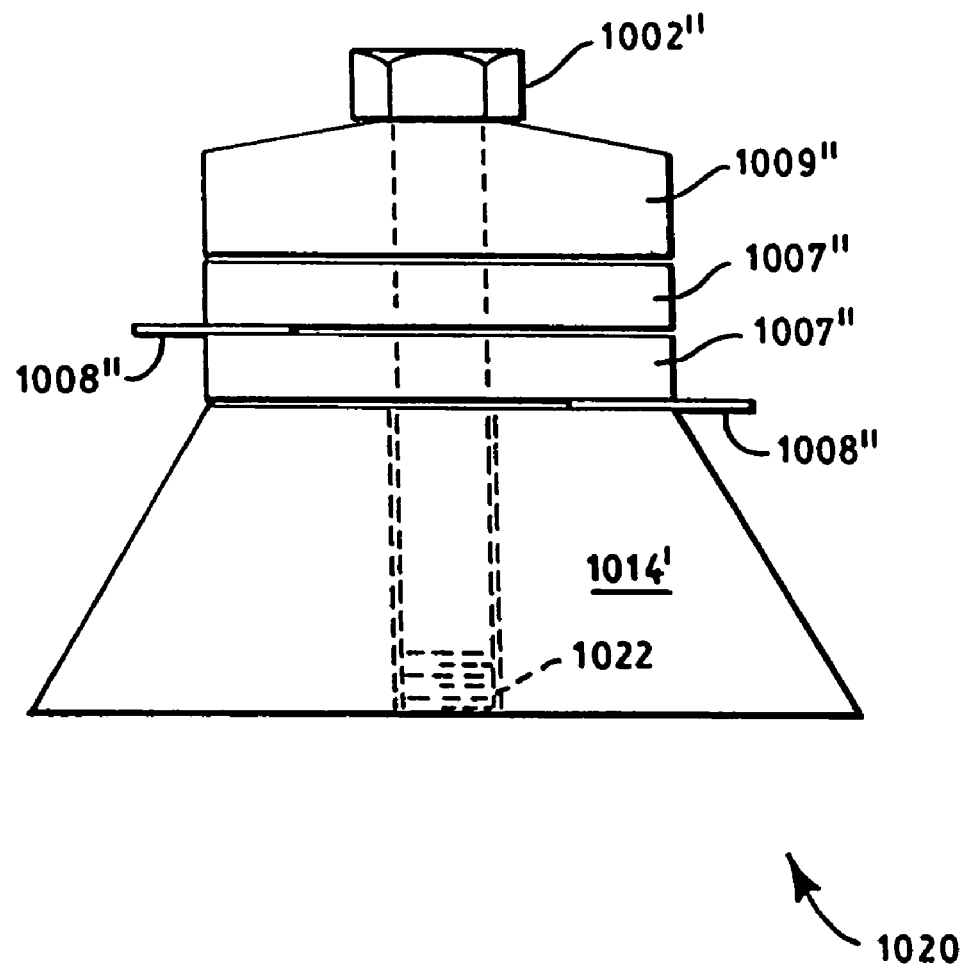
FIG. 53 illustrates one transducer of the invention utilizing a steel threaded insert to reduce stress on the front driver.

FIG. 53 illustrates a transducer 1020 that is similar to the transducer 1010, FIG. 52, except that a helical insert 1022 is used instead of the threads 1012. The helical insert 1022 is preferably made from steel and will not plastically deform under normal transducer stresses. The helical insert 1022 thus prevents distortion of the aluminum driver 1014' under the normal stresses of the transducer 1020. Note that the a helical insert can similarly replace the threads 1004 of the prior art transducer 1000 to provide similar advantages in preventing distortion.

Figure 54:
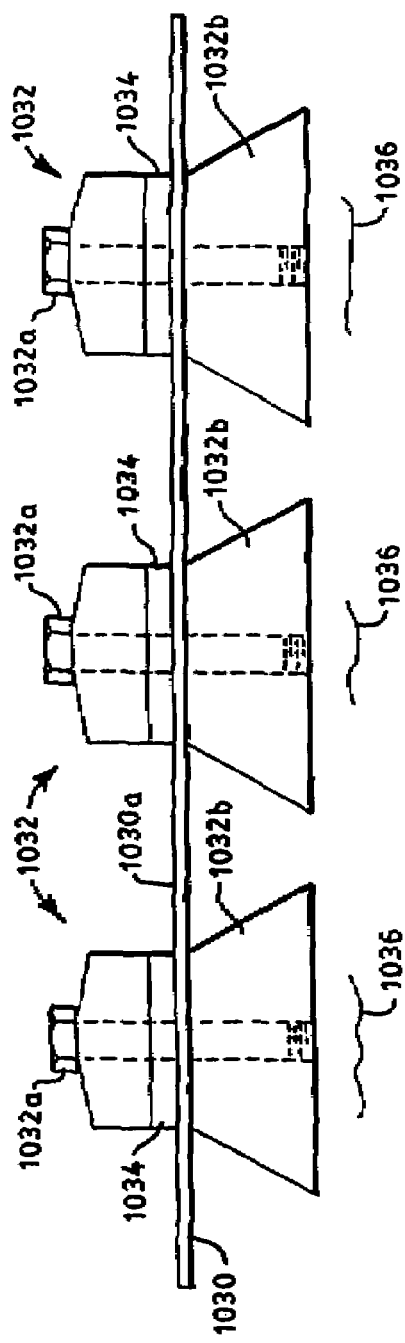
FIG. 54 shows a side view of a printed circuit board coupled with transducers as a single unit, in accord with the invention.

FIG. 54 illustrates a side view of one embodiment of the invention including a printed circuit board (PCB) 1030 connected with ultrasonic transducers 1032 such as described herein (including, for example, piezoelectric ceramics 1034). The PCB 1030 contains circuitry and wiring so as to function as an ultrasonic generator and for the electrodes of the transducers 1032. As such, the PCB 1030 can drive the transducers 1032 to produce ultrasound 1036 when powered. By way of example, the PCB 1030 can include the circuitry of FIG. 31.

The PCB 1030 and transducers 1032 are also substantially "integral" in construction so as to be a single unit. This provides structural integrity, and reduces the cost and size of the system.

Figure 55:
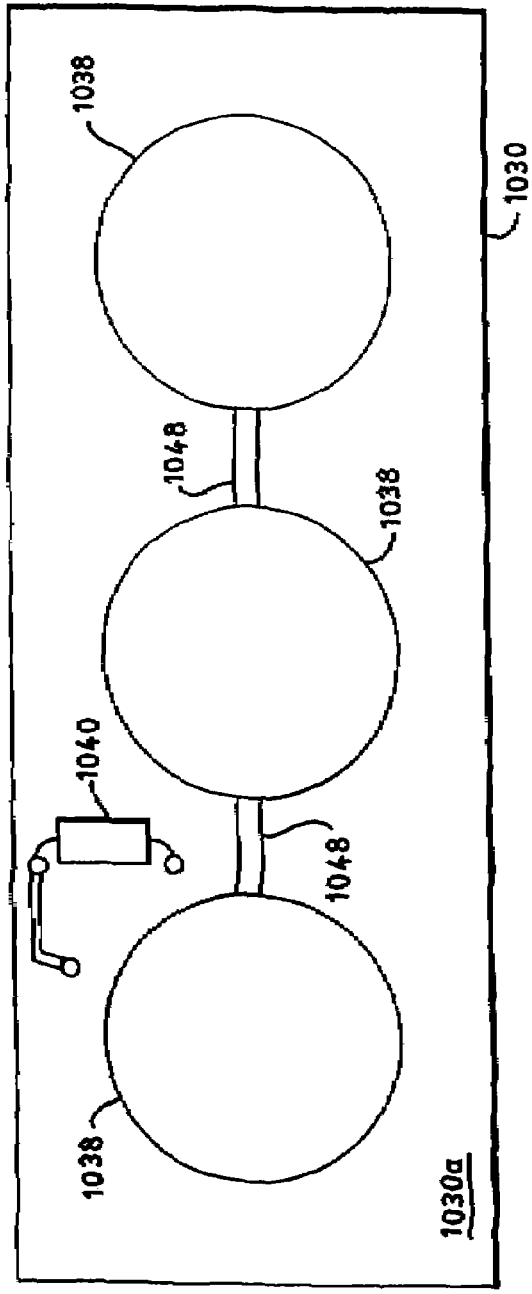
FIG. 55 shows a top view of the unit of FIG. 54.

FIG. 55 shows a top view of the PCB 1030 of FIG. 54. For purposes of illustration, the top surface 1030a of the PCB 1030 is shown with electrodes 1038 for the positive side of the piezoelectric ceramic 1034. The electrodes 1038 are preferably connected by wiring 1048 (e.g., circuit board land patterns) to provide for common voltage input to the transducers 1032. There is a similar electrode pattern on the bottom side (not shown) of the PCB 1030 that makes contact with the transducer's front driver 1032b, which is in electrical contact with the bias bolt 1032a (FIG. 54). The bolt 1032a connects through the transducer 1032 and into the back mass 1032c, providing electrical feedthrough to the negative electrode of the piezoelectric ceramic 1034. The PCB 1030 thus provides two electrodes for each transducer 1032 and all the interconnect wiring for the transducers 1032 such as by etching the PCB pattern. The ultrasonic generator is also provided with the PCB 1030 circuitry (illustrated by circuit board components 1040) with its output connected into the transducer electrodes as part of the PCB artwork.

Figure 56:
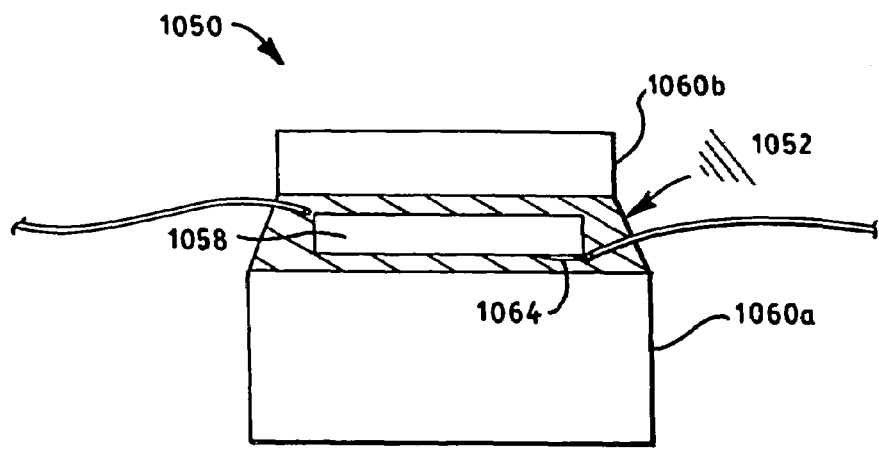
FIG. 56 shows an acid-resistant transducer constructed according to the invention.

FIG. 56 illustrates an acid resistant transducer 1050 with internal piezoelectric compression. By way of background, the above description has described certain transducers that utilize metal masses to lower the resonant frequency of the piezoelectric ceramics and a bolt to keep a compressive bias on the piezoelectric elements. In harsh environments, e.g., sulfuric acid process tanks, the metallic elements of the transducer are prone to acid attack and therefore are a reliability risk. The transducer 1050 of FIG. 56 resolves this problem by eliminating the metal masses and the bolt. The compressive force on the piezoelectric ceramic 1058 is obtained by an epoxy 1052 that contracts upon curing. The metal "back mass" and the metal "front driver" such as described above are replaced by a non-metallic material 1060. In FIG. 56, the front driver 1060a and back mass 1060b are thus both made from a non-metallic material such as quartz.

The internal piezoceramics 1058 connect to wiring to drive the elements 1058 in the normal way. To protect the wiring and ceramics, it can be made from Teflon which is soldered to the ceramic 1058 by known methods, such as illustrated by solder joint 1064.

Figure 57:
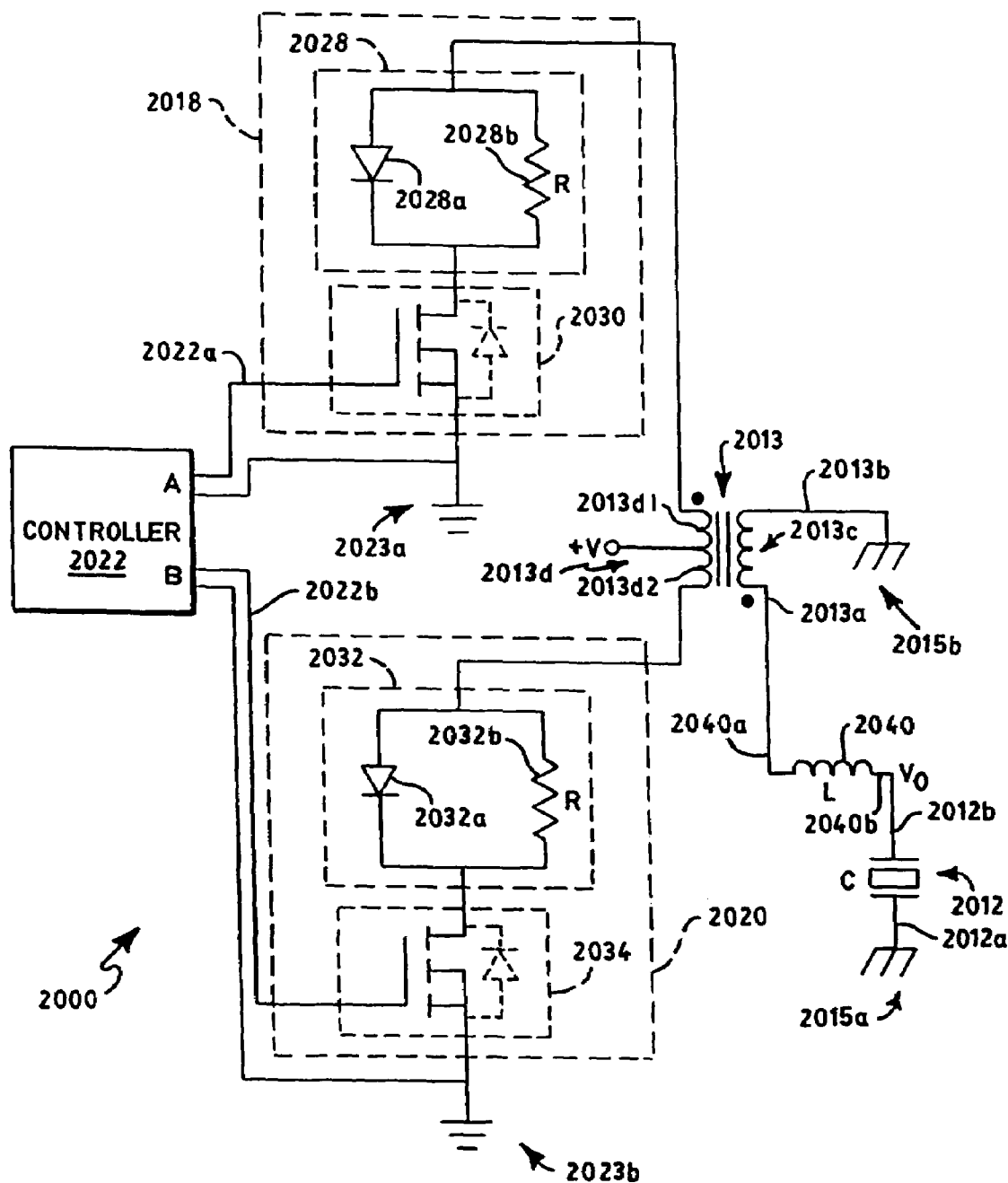
FIG. 57 schematically shows one power up-sweep generator circuit of the invention.

FIG. 57 illustrates a generator circuit 2000 used to implement power up-sweep such as described herein (e.g., such as described in connection with FIG. 31, except that FIG. 31 uses IGBT's as the switching devices and FIG. 57 uses MOSFET's). In FIG. 57, circuit 2000 includes a capacitive element 2012 with terminal 2012a connected to earth ground 2015a. The other terminal 2012b connects to terminal 2040b of inductor 2040. Terminal 2040a of inductor 2040 connects to terminal 2013a of the secondary 2013c of transformer 2013. Terminal 2013b of secondary 2013c connects to earth ground 2015b. The circuit 2000 includes two drive networks 2018 and 2020, and a controller 2022.

Drive network 2018 includes a blocking network 2028 and a multi-state power switch network 2030, which is coupled to the controller 2022 by way of line 2022a. The drive net-work 2020 includes a blocking network 2032 and a multi-state power switch network 2034, which is coupled to the controller 2022 by way of line 2022b.

In drive network 2018, the blocking network 2028 and switch network 2030 provide a unidirectional current flow path characterized by a first impedance from the potential +V through the first primary winding 2013d1 of center-tapped primary winding 2013d of transformer 2013 when the switch network 2030 is in a first (conductive) state. The networks 2028 and 2030 provide an oppositely directed current flow path characterized by a second impedance from circuit ground 2023a through 2013d1 to the potential +V when the switch network 2030 is in a second (non-conductive) state. The first impedance of the flow path established when network 2030 is in its first state is lower than the second impedance of the flow path established when the network 2030 is in its second state.

In drive network 2020, the blocking network 2032 and switch network 2034 provide a unidirectional current flow path characterized by a third impedance from the potential +V through the second primary winding 2013d2 of center-tapped primary winding 2013d of transformer 2013 when the switch network 2032 is in a first (conductive) state. The networks 2032 and 2034 provide an oppositely directed current flow path characterized by a fourth impedance from circuit ground 2023b through 2013d2 to the potential +V when the switch network 2034 is in a second (non-conductive) state. The third impedance of the flow path established when network 2034 is in its first state is lower than the fourth impedance of the flow path established when the network 2030 is in its second state.

The impedance (Z) of drive network 2018 when switch network 2030 is in its second state may be primarily determined by resistor 2028b (of value "R"), in which case Z has a value substantially equal to R for current flow in a direction toward +V, and a "near-infinity" value (i.e. relatively high) for current flow away from +V. In other embodiments, Z may be non-linear, normally lower at the beginning of operation in the second state and higher at times after the second state begins. For example, a metal oxide varistor (MOV) in parallel with a resistor (R) may be the primary determining factor for Z. In this case, at the beginning of operation in the second state when the voltage across Z is high, the low impedance of the on MOV primarily determines Z and later in the second state, as the voltage drops below the MOV's breakdown potential, Z is primarily determined by R.

A similar situation occurs for the impedance of drive network 2020 when switch network 2034 is in its second state.

Where the circuit 2000 is adapted to drive an ultrasonic transducer, the capacitive element 2012 may be an electrostrictive device suitable for use as an ultrasonic transducer. With such a configuration, for example, the controller 2022 may effectively control the circuit 2000 to drive such ultrasonic transducers at a selectively controlled frequency. In various forms of the invention, the controller 2022 may be adaptively controlled so as to track variations in the resonant frequency for the respective ultrasonic transducers, or to frequency modulate the frequency with a function such as a power up-sweep function, described above.

In operation, the controller 2022 cyclically switches the switch network 2030 between its first and second states at a frequency f (f=1/T), where f is less than or equal to $f_r$ ($f_r$=1/$T_r$), where $f_r$ is the resonant frequency of the series LC network formed by 2012 and 2040, approximately equal to $1/(2\pi(LC)^{1/2})$. During each cycle, network 2030 is controlled to be in its first state for a period greater than or equal to $T_r/2$, but less than or equal to T/2, at the beginning of each cycle. Network 2030 is controlled to be in its second state for the remainder of each cycle.

Similarly, the controller 2022 also cyclically switches the switch network 2032 between its first and second states at the frequency f (f=1/T). During each cycle, network 2032 is controlled to be in its first state for a period greater than or equal to $T_r/2$, but less than or equal to T/2, at the beginning of each cycle. Network 2032 is controlled to be in its second state for the remainder of each cycle. In the presently described embodiment, the start time for each cycle of the switching of network 2030 is offset by T/2 from the start time for each cycle of the switching of network 2034. In other forms, the start time for the cycle of the switching network 2030 may be offset by at least $T_r/2$ and less than $T_r/2+D$, where D equals $T-T_r$.

An AC voltage waveform ($V_o$) at frequency f is impressed across the capacitive element 2012. Generally, this voltage waveform $V_0$ passes from low to high and from high to low with a sinusoidal waveshape (at frequency $f_r$). After rising from its low peak level to its high peak level, the voltage waveform stays substantially at its high peak level (except for droop due to resistive losses) for a period ½ (T–$T_r$), or D/2, before passing from that high peak level to its low peak level. Similarly, upon returning to the low peak level, the voltage waveform $V_0$ remains at that level (except for droop due to resistive losses) for a period ½ (T–$T_r$), or D/2, before again passing to the high peak level.

Thus, the voltage impressed across capacitive element 2012 rises and falls at the resonant frequency $f_r$ with the capacitive element 2012 being maintained in its fully charged state for a "dead" time which is adjustably dependent upon the switching frequency f of the controller 2022. Accordingly, the drive frequency to the element 2012 may be adjustably controlled.

Where the element 2012 is an ultrasonic transducer, circuit 2000 is used to drive that transducer at a frequency adjusted to match the optimal drive frequency. In various embodiments, variations in that optimal drive frequency may be detected and the controller may be adjusted in closed loop fashion to adaptively track such variations.

Blocking network 2028 includes a diode 2028a in parallel with a resistor 2028b, and the blocking network 2032 includes a diode 2032a and a resistor 2032b. The single inductor (L) 2040 operates in resonance with the element 2012.

Circuit 2000 is particularly useful with "fast" switching devices (such as bipolar, MOS and IGBT transistors) which do not require an extended turn-off time. In operation, the capacitive element 2012 and transformer 2013 function like the circuit of FIG. 31, except that circuit 2000 utilizes FETs instead of IGBTs (insulated gate bipolar transistors) for the terminal power switching devices. The power devices 2030, 2034 are also connected to circuit ground, eliminating the need for separate isolated power supplies, reducing the cost of the generator.

In another implementation of circuit 2000, FIG. 57, the inductor 2040 is not a separate component, but rather is incorporated into the transformer 2013 by way of leakage inductance. This leakage inductance performs the same function as inductor 2040 and the leakage inductance is controlled by the coupling of transformer 2013, e.g., by setting a gap in the transformer's core as is known in the art.

Figure 60:
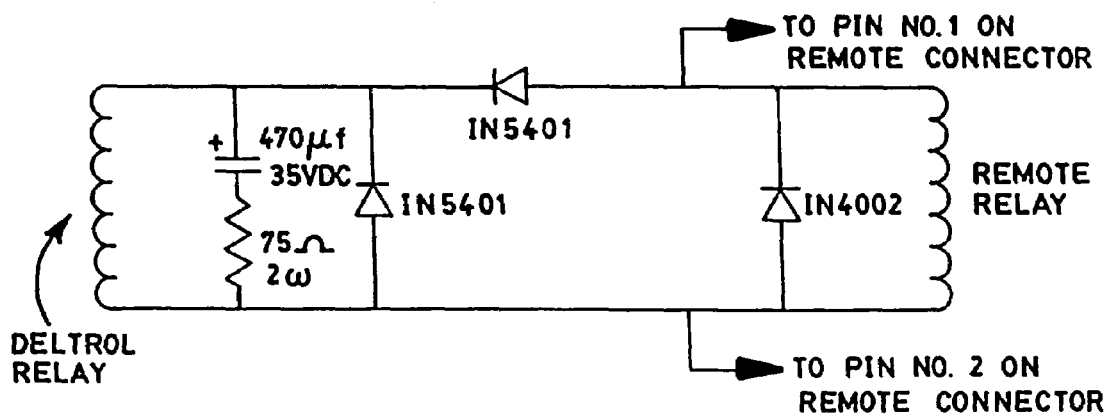
FIG. 60 schematically shows a circuit coupled to the rotary switch of FIG. 58.
Figure 58:
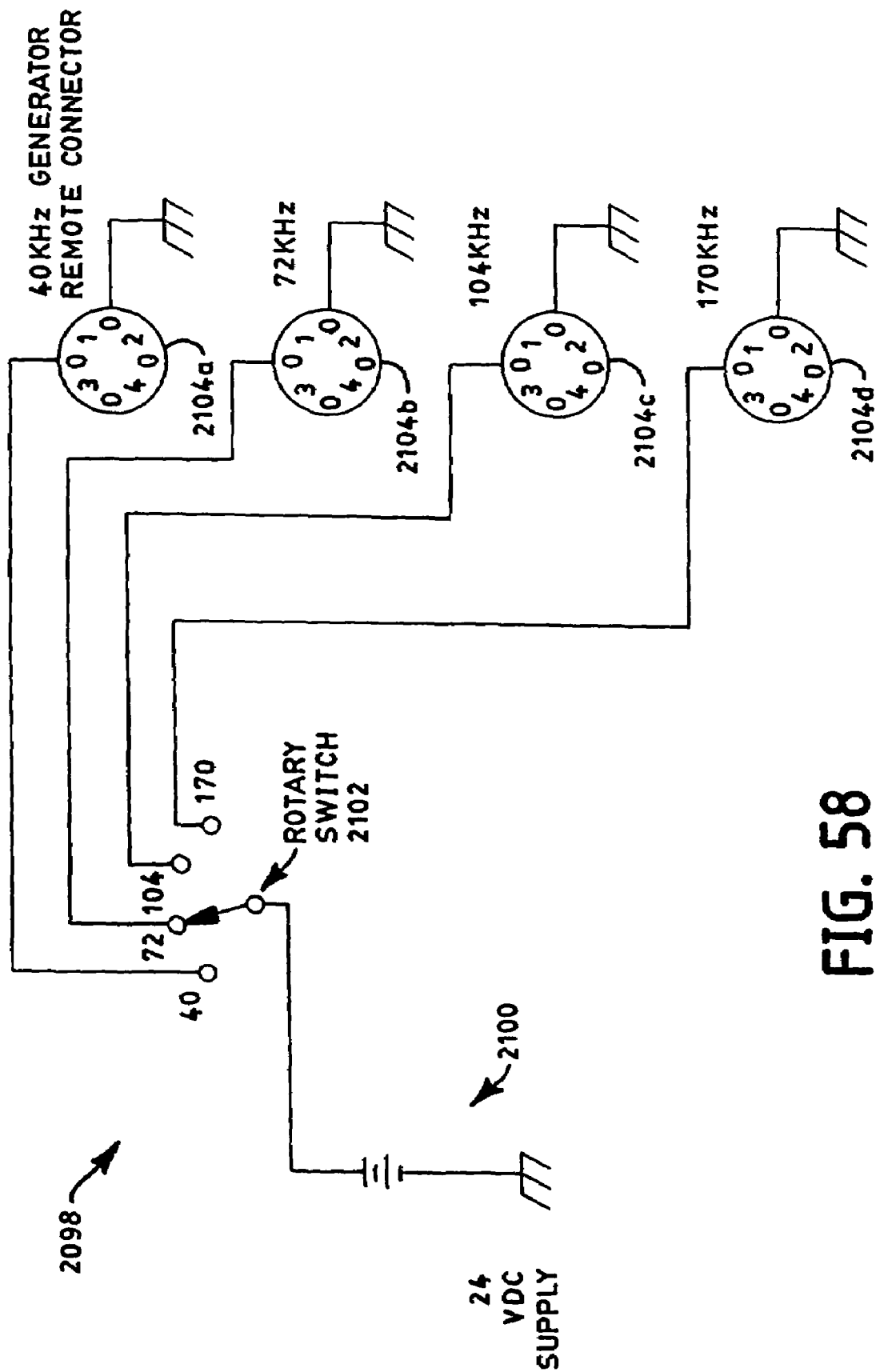
FIG. 58 illustrates a wiring schematic that couples a common voltage supply to one generator of a system that includes multiple generators, in accord with the invention.

With further reference to FIG. 33, one embodiment of the invention couples multiple generator frequencies to a common tank 306' and transducers 304'. FIG. 58 schematically shows additional switch circuitry 2098 compatible with this embodiment. In FIG. 58, a common 24 VDC supply 2100 couples to a user-selectable switch 2102 (e.g., a rotary switch) to provide drive energy to remote connectors 2104a–d (each connector 2104 corresponding and connecting to a different generator frequency, e.g., 2104a for 40 khz, 2104b for 72 khz, 2104c for 104 khz, and 2104d for 170 khz). Which ever generator thus connects to the 24 VDC supply between pins "1" and "2" on its corresponding remote connector 2104 will drive the common process tank, as shown in FIG. 59. The generators can have a remote on/off relay in the form of FIG. 60, which illustrates coupling between a Deltrol relay and the remove relay. The connector-to-tank wiring is further illustrated in FIG. 59. In FIG. 59, each generator within the system connects to each of the plurality of transducers 2106 within the tank; though only one generator actively drives the transducers 2106 depending upon the position of the switch 2102.

In operation, power is applied to one generator (e.g., the 40 khz generator coupled to remote connector 2104a) via the 24 VDC signal from the rotary switch 2102. The following sequence then occurs with respect to FIGS. 58–60:

| Time | Event |
| --- | --- |
| 7 milliseconds | Remote relay #1 energizes starting the ½ sec. timer #1 |
| 10 milliseconds | Deltrol relay #1 connects the tank to the 40 khz generator |
| 0.5 seconds | ½ sec. timer #1 starts the 40 khz generator, the tank runs at 40 khz |

If the rotary switch 2102 is turned to the next position, e.g., to the 72 khz generator position, the following sequence occurs (assuming, worst case, that the rotary switch is moved very fast so there is zero time between the 40 khz position and the 72 khz position):

| Time | Event |
| --- | --- |
| 0 milliseconds | 24 VDC is removed from remote relay #1 |
| 0 milliseconds | 24 VDC is removed from Deltrol relay #1 |
| 5 milliseconds | 40 khz generator turns off |
| 7 milliseconds | 72 khz remote relay #2 energizes starting the ½ sec. timer #2 |
| 10 milliseconds | Deltrol relay #2 connects tank to 72 khz generator |
| 250 milliseconds | Deltrol relay #1 disconnects 40 khz generator from the tank |
| 0.5 seconds | ½ sec. timer #2 starts the 72 khz generator, the tank runs at 72 khz |

To avoid this "worst case" scenario, extra margin is provided by providing an off position between each rotary switch generator position. That is, the rotary switch can be labeled as follows:

OFF-40 khz-OFF-72 khz-OFF-104 khz-OFF-170 khz

Generators connected within this system preferably have a four socket reverse sex square flange AMP CPC receptacle with arrangement 11–4 (AMP part number 206430-1) installed on the rear of the generator. The mating four pin plug (AMP part number 206429-1) has the following pin connections:

| | |
| --- | --- |
| Pin#1 | +24 VDC referenced to Pin #2 connects the generator or power module to the transducers and turns the generator on |
| Pin#2 | return for 24 VDC signal, can be grounded |
| Pin#3 | anode of LED to indicate RF current flow |
| Pin#4 | cathode of LED to indicate RF current flow |

The cable from the AMP plug is for example a Manhattan/Cot PIN M39025 control cable with four #24 AWG wires, with the following color codes: Pin#1 red; Pin#2 green; Pin#3 blue; and Pin#4 white.

Generators within this system can have a nine socket reverse sex square flange AMP CPC receptacle with arrangement 17–9 (AMP part number 211769-1) installed on the rear of the generator according to the following connections.

Socket #1: +RF output
Socket #2: not used
Socket #3: +RF output
Socket #4: −DC test point
Socket #5: −RF output, ground
Socket #6: cable shield, ground
Socket #7: +DC output interlock
Socket #8: +DC input interlock
Socket #9: waveform test point The mating nine pin plug (AMP part number 211768-1) can have the following pin outs and color code when supplied with a three wire RF cable.

Pin #1: +RF output red
Pin #3: +RF output red
Pin #5: −RF output green/yellow

All pin #5s can for example be wired together and connected to the −RF transducer lead. All pin #1's are then connected together and connected to the +RF transducer lead coming from one-half of the transducers. All pin #3's are then connected together to the +RF transducer lead coming from the other one-half of the transducers. The only exception to this is when the generators do not all drive the same number of transducers.

Figure 61:
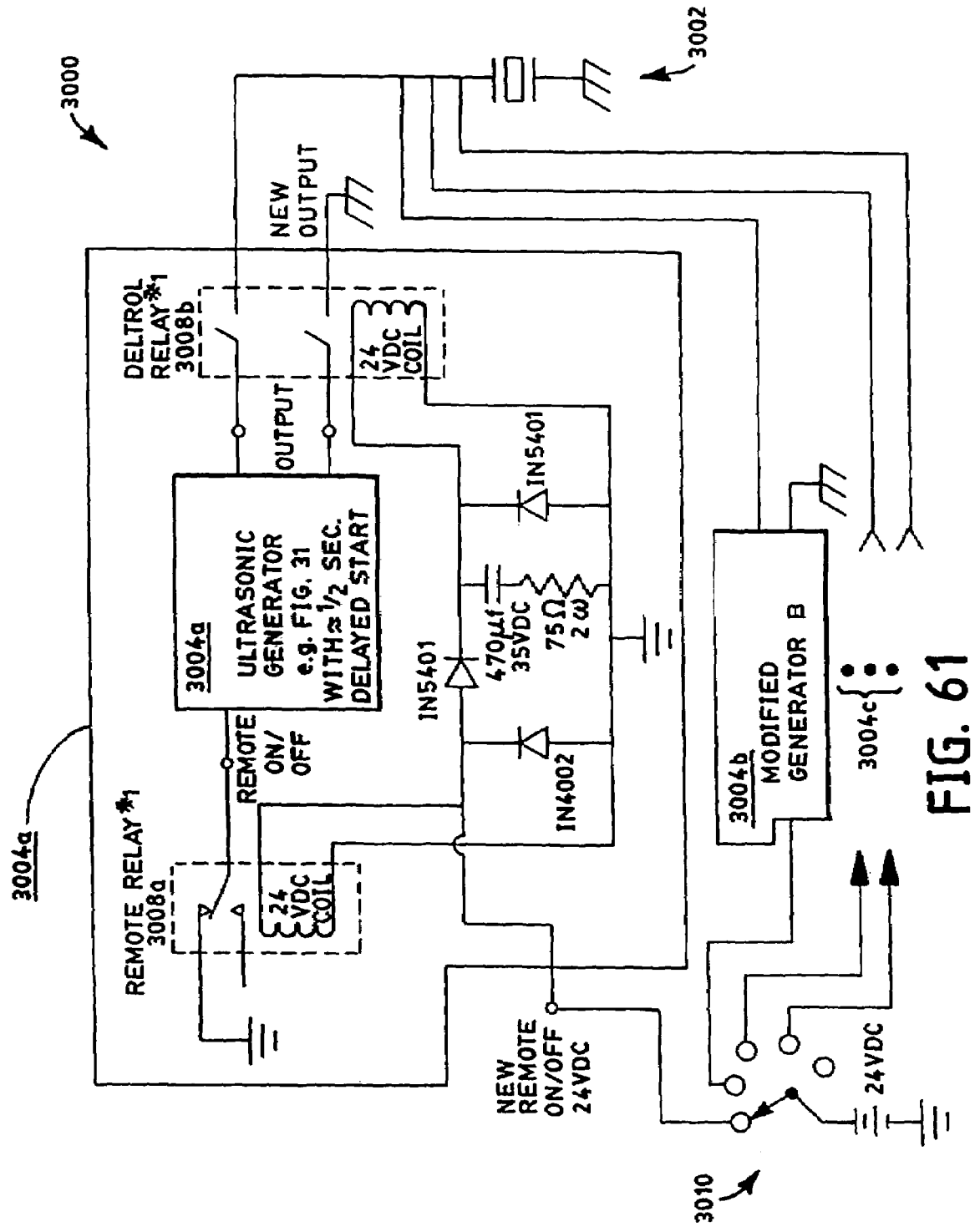
FIG. 61 shows a multi-generator system constructed according to the invention.

FIG. 61 schematically shows a multi-generator system 3000 used to drive common transducers 3002. One advantage of the system 3000 is that multiple generators 3004 can alternatively drive the transducer 3002; and it is assured that no two generators operate simultaneously. Each generator 3004 preferably represents a different drive frequency. Generator 3004a represents, for example, the generator set forth by circuitry of FIG. 31 (except that preferably, a ½ second delay is installed into circuit 250 by adjusting capacitor 3006 to one microfarad instead of $\frac{1}{10}$ microfarad, which provides only 50 ms delay). The relays 3008a, 3008b for example can be implemented similar to the relay schematic of FIG. 60.

The rotary switch 3010 (e.g., similar to the switch 2102, FIG. 58) permits user selection between any of the generators 3004. Generator 3004b can thus be switched in to drive the transducer 3002 with a different frequency. Those skilled in the art should appreciate that additional generators 3004c, 3004d, . . . can be installed into the system 3000 as desired, with additional frequencies. Those skilled in the art should appreciate that the rotary switch 3010 can be replaced by a PLC or computer control to provide similar generator selection.

The invention thus attains the objects set forth above, among those apparent in the preceding description. Since certain changes may be made in the above description without departing from the scope of the invention, it is intended that all matter contained in the above description or shown in the accompanying drawings be interpreted as illustrative and not in a limiting sense. It is also to be understood that the following claims are to cover all generic and specific features of the invention described herein, and all statements of the scope of the invention which, as a matter of language, might be said to fall therebetween.

What is claimed is:

1. A probe system for sensing process conditions within an ultrasonic process tank of the type that includes process liquid, the liquid being subjected to ultrasound produced by transducers coupled to a generator, comprising:

(a) an enclosure for housing a sample liquid, wherein said enclosure is adapted to isolate said sample liquid from said process liquid, the enclosure passing ultrasonic energy from the process liquid to the sample liquid, the sample liquid being responsive to the energy; and (b) one or more sensing transducers within the sample liquid, the transducers generating signals indicative of characteristics of the sample liquid.

2. A probe system of claim 1, wherein the housing comprises polypopylene.

3. A probe system of claim 1, wherein one transducer comprises means for determining the conductivity of the sample liquid and for generating a signal indicative of the conductivity.

4. A probe system of claim 1, wherein one transducer comprises means for determining the temperature of the sample liquid and for generating a signal indicative of the temperature.

5. A probe system of claim 1, further comprising a temperature transducer attached to the outside of the housing for determining a temperature of the process liquid and for generating a signal indicative of the temperature.

6. A probe system of claim 1, further comprising an analysis subsystem for collecting the signals and for evaluating the signals over time.

7. A probe system of claim 6, wherein the subsystem comprises means for generating control signals which control the generator in response to evaluated signals over time.

8. A probe system of claim 6, wherein the subsystem comprises a microprocessor.

9. A probe system for sensing process conditions within an ultrasonic process tank of the type that includes process liquid, the liquid being subjected to ultrasound produced by transducers coupled to a generator, comprising:
  (a) an enclosure for housing a sample liquid, the enclosure passing ultrasonic energy from the process liquid to the sample liquid, the sample liquid being responsive to the energy;
  (b) one or more sensing transducers within the sample liquid, the transducers generating signals indicative of characteristics of the sample liquid;
  (c) an analysis subsystem for collecting the signals and for evaluating the signals over time; and
  (d) means for determining total cavitation energy released based upon signals indicative of temperature of the sample liquid over time.

10. A probe system for sensing process conditions within an ultrasonic process tank of the type that includes process liquid, the liquid being subjected to ultrasound produced by transducers coupled to a generator, comprising:
  (a) an enclosure for housing a sample liquid, the enclosure passing ultrasonic energy from the process liquid to the sample liquid, the sample liquid being responsive to the energy;
  (b) one or more sensing transducers within the sample liquid, the transducers generating signals indicative of characteristics of the sample liquid;
  (c) an analysis subsystem for collecting the signals and for evaluating the signals over time; and
  (d) means for calculating total energy released from cavitation through the following relationship: energy (calories)=specific heat×mass of the sample liquid×change in temperature (° C.).

11. A probe system for sensing process conditions within an ultrasonic process tank of the type that includes process liquid, the liquid being subjected to ultrasound produced by transducers coupled to a generator, comprising:
  (a) an enclosure for housing a sample liquid, the enclosure passing ultrasonic energy from the process liquid to the sample liquid, the sample liquid being responsive to the energy;
  (b) one or more sensing transducers within the sample liquid, the transducers generating signals indicative of characteristics of the sample liquid;
  (c) an analysis subsystem for collecting the signals and for evaluating the signals over time; and
  (d) means for determining cavitation density based upon signals indicative of conductivity of the sample liquid.

12. A probe system of claim 11, further comprising means for determining cavitation density as a function of time.

13. A probe system for sensing process conditions within an ultrasonic process tank of the type that includes process liquid, the liquid being subjected to ultrasound produced by transducers coupled to a generator, comprising:
  (a) an enclosure for housing a sample liquid, the enclosure passing ultrasonic energy from the process liquid to the sample liquid, the sample liquid being responsive to the energy;
  (b) one or more sensing transducers within the sample liquid, the transducers generating signals indicative of characteristics of the sample liquid;
  (c) an analysis subsystem for collecting the signals and for evaluating the signals over time; and
  wherein the subsystem comprises memory for storing at least one of the following parameters: specific heat (p) of the sample liquid, volume (V) of the sample liquid, mass (m) of the sample liquid, and a functional relationship defined as $n=f(C,C_o)$ between conductivity and a number (n) of cavitation implosions.

14. A probe system of claim 13, further comprising means for calculating cavitation density based upon $n/V=f(C,C_o)/V$.

15. A probe system of claim 13, further comprising means for calculating energy in each cavitation implosion based upon $(0.00833)(p)(m)(g(t'))/V/f(C,C_o)/t'$, where t' corresponds to a time of measurement.

16. A probe system of claim 13, further comprising means for calculating cavitation density based upon cavitation density as a function of $time=f(h(t))/V$.

17. A probe system of claim 13, further comprising means connected to the generator for controlling the generator based upon calculations of the subsystem.

18. A probe system of claim 17, further comprising one or more comparators for comparing the calculations to one or more stored parameters.

19. A probe system for sensing process conditions within an ultrasonic process tank of the type that includes process liquid, the liquid being subjected to ultrasound produced by transducers coupled to a generator, comprising:
  (a) an enclosure for housing a sample liquid, the enclosure passing ultrasonic energy from the process liquid to the sample liquid, the sample liquid being responsive to the energy;
  (b) one or more sensing transducers within the sample liquid, the transducers generating signals indicative of characteristics of the sample liquid;
  (c) an analysis subsystem for collecting the signals and for evaluating the signals over time; and p1 wherein the subsystem comprises feedback means for controlling generator frequency in response to the signals.

20. A probe system for sensing process conditions within an ultrasonic process tank of the type that includes process liquid, the liquid being subjected to ultrasound produced by transducers coupled to a generator, comprising:
  (a) an enclosure for housing a sample liquid, the enclosure passing ultrasonic energy from the process liquid to the sample liquid, the sample liquid being responsive to the energy;
  (b) one or more sensing transducers within the sample liquid, the transducers generating signals indicative of characteristics of the sample liquid;
  (c) an analysis subsystem for collecting the signals and for evaluating the signals over time; and
  wherein the subsystem comprises feedback means for controlling generator power output in response to the signals.

21. A probe system for sensing process conditions within an ultrasonic process tank of the type that includes process liquid, the liquid being subjected to ultrasound produced by transducers coupled to a generator, comprising:
- (a) an enclosure for housing a sample liquid, the enclosure passing ultrasonic energy from the process liquid to the sample liquid, the sample liquid being responsive to the energy;
- (b) one or more sensing transducers within the sample liquid, the transducers generating signals indicative of characteristics of the sample liquid;
- (c) an analysis subsystem for collecting the signals and for evaluating the signals over time; and
- wherein the subsystem comprises feedback means for amplitude modulating signals from the generator to control cavitation density as a function of time within the process liquid.

22. A probe system of claim 6, further comprising means for determining total cavitation energy released based upon signals indicative of temperature of the sample liquid over time.

23. A probe system of claim 6, further comprising means for calculating total energy released from cavitation through the following relationship: energy (calories)=specific heat×mass of the sample liquid×change in temperature (° C.).

24. A probe system of claim 6, further comprising means for determining cavitation density based upon signals indicative of conductivity of the sample liquid.

25. A probe system of claim 1, wherein the subsystem comprises memory for storing at least one of the following parameters: specific heat (p) of the sample liquid, volume (V) of the sample liquid, mass (m) of the sample liquid, and a functional relationship defined as $n=f(C,C_o)$ between conductivity and a number (n) of cavitation implosions.

26. A probe system of claim 25, further comprising means for calculating cavitation density based upon $n/V=f(C,C_o)/V$.

27. A probe system of claim 25, further comprising means for calculating energy in each cavitation implosion based upon $(0.00833)(p)(m)(g(t'))/V/f(C,C_o)/t'$, where t' corresponds to a time of measurement.

28. A probe system of claim 25, further comprising means for calculating cavitation density based upon cavitation density as a function of time=$f(h(t))/V$.

29. A probe system of claim 24, further comprising means for determining cavitation density as a function of time.

30. A probe system of claim 26, further comprising means connected to the generator for controlling the generator based upon calculations of the subsystem.

31. A probe system of claim 30, further comprising one or more comparators for comparing the calculations to one or more stored parameters.

32. A probe system of claim 6, wherein the subsystem comprises feedback means for controlling generator frequency in response to the signals.

33. A probe system of claim 6, wherein the subsystem comprises feedback means for controlling generator power output in response to the signals.

34. A probe system of claim 6, wherein the subsystem comprises feedback means for amplitude modulating signals from the generator to control cavitation density as a function of time within the process liquid.

* * * * *

UNITED STATES PATENT AND TRADEMARK OFFICE
CERTIFICATE OF CORRECTION

PATENT NO. : 7,004,016 B1  
APPLICATION NO. : 09/370302  
DATED : February 28, 2006  
INVENTOR(S) : William L. Puskas It is certified that error appears in the above-identified patent and that said Letters Patent is hereby corrected as shown below:

Title page, Page 1, Column 1, after (22) and before (51), should be amended to read:
--Related U.S. Application Data--
--Divisional of U.S. Patent Application Serial No.09/097,374, filed on June 15, 1998, now U.S. Patent No. 6,016,821,which is a continuation of U.S. Provisional Patent Application Serial No. 60/049,717, filed on June 16, 1977 --

--Continuation-in-part of U.S. Patent Application Serial No. 08/718,945, filed on September 24, 1996, now U.S. Patent No. 5,834,871,--

Signed and Sealed this

Fifteenth Day of August, 2006

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,004,016 B1 | Page 1 of 1 |
| APPLICATION NO. | : 09/370302 | |
| DATED | : February 28, 2006 | |
| INVENTOR(S) | : William L. Puskas | |

It is certified that error appears in the above-identified patent and that said Letters Patent is hereby corrected as shown below:

Title page, Page 1, Column 1, after (22) and before (51), should be amended to read:

--Related U.S. Application Data--

--Divisional of U.S. Patent Application Serial No.09/097,374, filed on June 15, 1998, now U.S. Patent No. 6,016,821, which is a continuation of U.S. Provisional Patent Application Serial No. 60/049,717, filed on June 16, 1997 --

--Continuation-in-part of U.S. Patent Application Serial No. 08/718,945, filed on September 24, 1996, now U.S. Patent No. 5,834,871,--

This certificate supersedes Certificate of Correction issued August 15, 2006.

Signed and Sealed this

Twentieth Day of November, 2007

JON W. DUDAS
*Director of the United States Patent and Trademark Office*